US012351810B2

(12) United States Patent
Liu et al.

(10) Patent No.: US 12,351,810 B2
(45) Date of Patent: Jul. 8, 2025

(54) RESISTANCE GENES ASSOCIATED WITH DISEASE RESISTANCE IN SOYBEANS

(71) Applicant: Syngenta Crop Protection AG, Basel (CH)

(72) Inventors: Qingli Liu, Durham, NC (US); Thomas Joseph Curley, Jr., Durham, NC (US); Becky Welsh Breitinger, Durham, NC (US); John Daniel Hipskind, Durham, NC (US); John Luther Dawson, Durham, NC (US); Xiaoping Tan, Durham, NC (US); Andrew David Farmer, Santa Fe, NM (US); Euihwan Chung, Durham, NC (US)

(73) Assignee: SYNGENTA CROP PROTECTION AG, Basel (CH)

( * ) Notice: Subject to any disclaimer, the term of this patent is extended or adjusted under 35 U.S.C. 154(b) by 0 days.

(21) Appl. No.: 17/398,133

(22) Filed: Aug. 10, 2021

(65) Prior Publication Data
US 2022/0162634 A1 May 26, 2022

Related U.S. Application Data

(60) Provisional application No. 63/042,101, filed on Jun. 17, 2021.

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS

2013/0333061 A1* 12/2013 Wu ................... C07K 14/415
800/300
2018/0103600 A1 4/2018 Rairdan et al.
2019/0136250 A1 5/2019 Que et al.
(Continued)

FOREIGN PATENT DOCUMENTS

WO WO-2021154632 A1 * 8/2021 ............... A01H 1/04
WO WO-2021260673 A2 * 12/2021 ........... C07K 14/415
WO WO-2021263249 A2 * 12/2021

OTHER PUBLICATIONS

Ellis et al. "The generation of plant disease resistance gene specificities" 2000 Trends in Plant Sci. 5(9):373-379 (Year: 2000).*
(Continued)

*Primary Examiner* — Matthew R Keogh
*Assistant Examiner* — Rebecca Stephens
(74) *Attorney, Agent, or Firm* — Suparna Kanjilal

(57) ABSTRACT

The present invention relates to methods and compositions for identifying, selecting and/or producing a Disease resistant soybean plant or germplasm using genes derived from wild *Glycine*. A soybean plant or germplasm that has been identified, selected and/or produced by any of the methods of the present invention is also provided. Disease resistant soybean seeds, plants and germplasms are also provided.

18 Claims, 9 Drawing Sheets

Specification includes a Sequence Listing.

(56) References Cited

U.S. PATENT DOCUMENTS

2022/0380796 A1* 12/2022 Shan .................. A01H 1/1255

OTHER PUBLICATIONS

Langenbach et al—"Interspecies gene transfer provides soybean resistance to a fungal pathogen"—Blant Biotechnol Journal 2016 vol. 14(2)—pp. 699 to 708.
Langenbach et al—"Fighting Asian Soybean Rust"—Frontiers in Plant Science 2016 vol. 7 797—pp. 1 to 13.
Mammadov et al—"Wild Relatives of Maize, Rice, Cotton and Soybean. Treasure Troves for Tolerance to Biotic and Abiotic Stresses"—Frontiers in Plant Science 2018, vol. 9, 886—pp. 1 to 21.
Yu et al—"Fine mapping of the Asian soybean rust resistance gene Rpp2 from soybean PI23097"—Theor Appl Genet 2015, vol. 128(3)—pp. 387-396.
ISR for PCT/US21/45320. Date of search Nov. 30, 2021 (mailed Feb. 2, 2022).

\* cited by examiner (Fungal biomass quantification, soy rust disease ratings of GM events across a range of events with copy numbers var (Fungal biomass quantification, soy rust disease ratings of GM events across a range of events with copy numbers varies from 0

(GmUbi promoter Expression Cassette)

(UBQ promoter Expression Cassette)

RESISTANCE GENES ASSOCIATED WITH DISEASE RESISTANCE IN SOYBEANS

RELATED APPLICATIONS

This application claims priority to U.S. Provisional Patent Application No. 63/042,101 filed Jun. 22, 2020.

FIELD OF THE INVENTION

The present disclosure relates to compositions and methods for identifying, selecting and producing enhanced disease and/or pathogen resistant plants using novel resistance genes.

STATEMENT REGARDING SUBMISSION OF A SEQUENCE LISTING

A Sequence Listing in ASCII text format, submitted under 37 C.F.R. § 1.821, entitled "82139_seqlist_ST25" generated on Aug. 9, 2021 that is ~122 kb in size, and filed via EFS-Web, is provided in lieu of a paper copy. This Sequence Listing is hereby incorporated by reference into the specification for its disclosures.

BACKGROUND

Plant pathogens are known to cause considerable damage to important crops, resulting in significant agricultural losses with widespread consequences for both the food supply and other industries that rely on plant materials. As such, applicant desires to reduce the incidence and/or impact of agricultural pathogens on crop production.

Several pathogens have been associated with damage to soybeans, which individually and collectively have the potential to cause significant yield losses in the United States and throughout the world. Exemplary pathogens include, but are not limited to fungi (e.g., genus *Phytophthora* and Asian Soybean rust *Phakopsora pachyrhizi*), nematodes (e.g., genus *Meloidogyen*, particularly, *Meloidogyne javanica*), and soybean stem canker. Given the significant threat to global food supplies that these pathogens present as well as the time and expense associated with treating soybean crops to prevent yield loss, new methods for producing pathogen resistant soybean cultivars are needed. Applicant therefor desires novel resistance genes that can be introduced into commercial soybean plants to control soybean pathogens.

SUMMARY OF THE INVENTION

This summary lists several embodiments of the presently disclosed subject matter, and in many cases lists variations and permutations of these embodiments.

Compositions and methods for identifying, selecting and producing *Glycine* plants (including wild *Glycines*, e.g. *Glycine canescens, Glycine clandestine, Glycine tomentella,* and *Glycine max* lines) with enhanced disease resistance are provided. Disease resistant soybean plants and germplasms are also provided. In some embodiments, methods of producing a disease resistant soybean plant are provided.

In one aspect of the invention there is provided a DNA construct that comprises a promoter that functions in plant cells operably linked to a novel resistance gene or genes chosen from at least one of an RG21 gene and an RG22 gene. In yet another aspect of the invention there is provided a transgenic plant that contains the DNA construct, wherein the transgenic plant is resistant to soybean pathogens, particularly Asian Soybean Rust (ASR). RG21 and RG22 genes may vary from embodiment to embodiment. RG21 genes may include, for example, a gene encoding a protein having at least 70%-100% sequence identity to SEQ ID NO: 1. Similarly, RG22 genes may vary and may include genes encoding a protein having at least 70%-100% sequence identity to SEQ ID NO: 12

In another aspect of the invention is a method of preparing a fertile transgenic plant comprising providing a plant expression cassette comprising at least one of an RG21 gene and an RG22 gene and contacting recipient plant cells with the plant expression cassette under conditions permitting the uptake of the plant expression cassette by the recipient cells; selecting the recipient plant cells that contain the plant expression cassette; regenerating plants from the selected recipient plant cells; and identifying a fertile transgenic plant that is resistant to soybean pathogens, particularly ASR.

In another aspect of the invention there is provided a fertile transgenic plant that comprises a plant expression cassette comprising at least one of an RG21 gene and an RG22 gene and wherein the plant is resistant to soybean pathogens, particularly ASR.

In another aspect of the invention there is provided a method of controlling ASR in a field comprising the step of planting the seed from a plant comprising at least one of an RG21 gene and an RG22 gene.

Thus, it is an object of the presently disclosed subject matter to provide methods for conveying pathogen resistance into non-resistant soybean germplasm or plant lines.

Further the presently disclosed subject matter provides novel *Glycine max* lines comprising in its genome at least one of an RG21 gene and an RG22 gene that is derived from a wild *Glycine* species, e.g. *Glycine canescens* or *Glycine clandestina* or *Glycine tomentella* and further confers ASR resistance in said novel *Glycine max* line. Soybean plants and/or germplasms identified, produced or selected by the methods of this invention are also provided, as are any progeny and/or seeds derived from a soybean plant or germplasm identified, produced or selected by these methods.

As still a further aspect, the invention encompasses transgenic plants comprising a plant cell, plant part, nucleotide sequence, expression cassette, vector and/or at least one of an RG21 gene and an RG22 gene.

As a further aspect are seeds that produce the transgenic plants of the invention and seeds produced by the transgenic plants of the invention.

Also provided are harvested products derived from the transgenic plants of the invention, wherein the harvested product optionally comprises a nucleotide sequence, expression cassette, vector and/or at least one of an RG21 gene and an RG22 gene. Further provided are processed products derived from the harvested products of the invention, wherein the harvested product optionally comprises a nucleotide sequence, expression cassette, vector and/or at least one of an RG21 gene and an RG22 gene.

Still further, the disclosure provides as an additional aspect a method of producing a transgenic plant with increased resistance to a soybean pathogen. In embodiments, the method comprises introducing into a plant a polynucleotide, expression cassette, or vector of the invention, wherein at least one of an RG21 gene and an RG22 gene is expressed in the plant, thereby producing a transgenic plant with increased resistance to a soybean pathogen. Optionally, the introducing step comprises: (i) transforming a plant cell with the polynucleotide, expression cassette or vector and regenerating a transgenic plant; or (ii) crossing a first plant comprising the polynucleotide, expression cassette or vector with a second plant. In some embodiments, introducing may be achieved by manually-introgressing an exogenous gene to produce a non-viable, non-native embryo and chemically rescuing that embryo. In embodiments, the method further comprises producing a seed from the transgenic plant. In embodiments, the method further comprises obtaining a progeny plant from the transgenic plant, wherein the progeny plant comprises the polynucleotide, the expression cassette or the vector, expresses at least one of an RG21 gene and an RG22 gene and has increased resistance to a soybean pathogen.

As yet another aspect, the invention provides a method of producing a transgenic plant with increased resistance to a soybean plant pathogen (e.g., Asian Soybean Rust), the method comprising: (a) planting a seed comprising a polynucleotide, expression cassette or vector of the invention; and (b) growing a transgenic plant from the seed, wherein the transgenic plant comprises the polynucleotide, expression cassette or vector and produces the RG21 gene and has increased resistance to a soybean pathogen. In embodiments, the method further comprises: (c) harvesting a seed from the transgenic plant of (b), wherein the harvested seed comprises the polynucleotide, expression cassette, vector and/or at least one of an RG21 gene and an RG22 gene.

Still further, as another aspect, the invention provides a method of producing a seed. In embodiments, the method comprises: (a) providing a transgenic plant that comprises a polynucleotide, expression cassette or vector of the invention; and (b) harvesting a seed from the transgenic plant of (a), wherein the harvested seed comprises the polynucleotide, expression cassette or vector and/or at least one of an RG21 gene and an RG22 gene.

The invention further contemplates a method of producing a hybrid plant seed. In representative embodiments, the method comprises: (a) crossing a first inbred plant, which is a transgenic plant comprising a polynucleotide, expression cassette or vector of the invention with a different inbred plant, which may or may not comprise a polynucleotide, expression cassette or vector of the invention; and (b) allowing a hybrid seed to form.

The invention is also drawn to methods of using the polynucleotides of the invention, for example, in DNA constructs or expression cassettes or vectors for transformation and expression in organisms, including plants. The nucleotide or amino acid sequences may be native or synthetic sequences that have been designed for expression in an organism such as a plant.

In embodiments, the invention provides a method of using a polynucleotide, expression cassette or vector of the invention to produce a transgenic seed, where the transgenic seed grows a transgenic plant with increased resistance to a soybean pathogen.

The foregoing and other objects and aspects of the present invention are explained in detail in the drawings and specification set forth below.

BRIEF DESCRIPTION OF THE SEQUENCE LISTING

Figure 1:
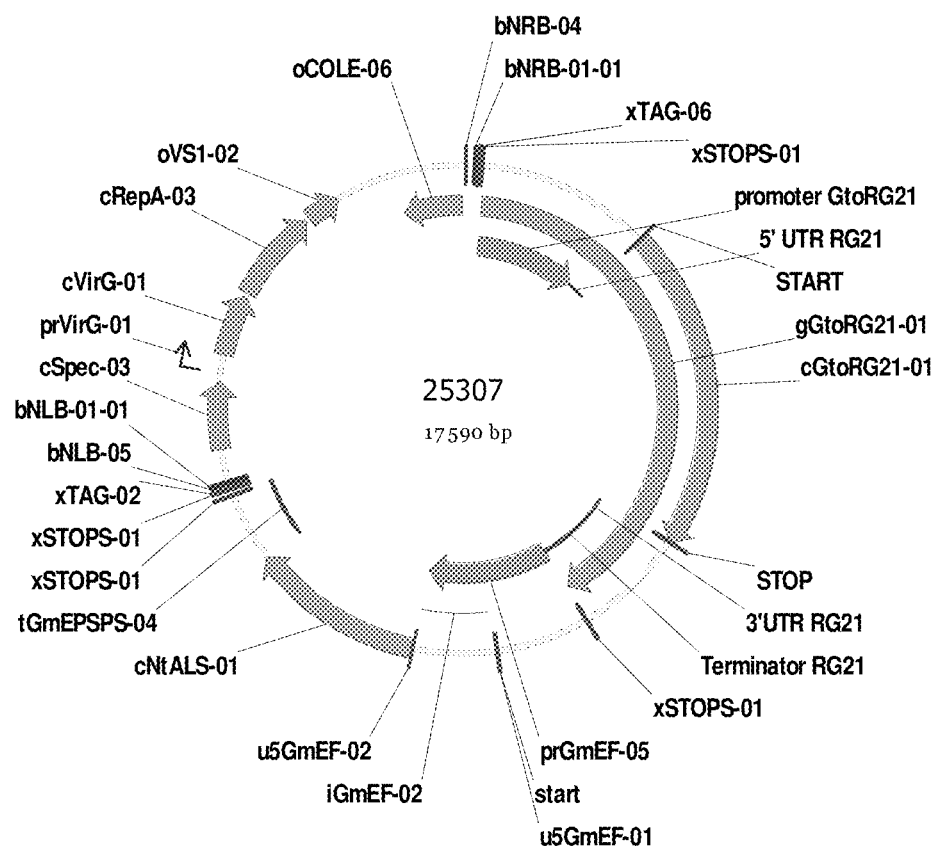
FIG. 1 is an illustration of vector 25307 containing an RG21 gene.

SEQ ID NO: 1 is an amino acid sequence for a RG21 gene.
SEQ ID NO: 2 is a DNA sequence for a RG21 gene.
SEQ ID NOs: 3-4 are exemplary vectors containing an RG21 gene.
SEQ ID NOs: 6-8 are exemplary promoters suitable for driving expression of the RG21 gene.
SEQ ID NOs: 9-11 are assay components for detecting RG21.
SEQ ID NO: 12 is an amino acid sequence for a RG22 gene.
SEQ ID NO: 13 is a DNA sequence for a RG22 gene.
SEQ ID NO: 14 is an exemplary vector containing an RG22 gene.

DETAILED DESCRIPTION OF THE INVENTION

The presently disclosed subject matter relates to compositions and methods for introducing novel resistance genes (RG21 and/or RG22 genes) into commercial soybean plants to control soybean pathogens. In some embodiments, the methods involve transforming organisms with nucleotide sequences encoding the RG21 and/or RG22 genes of the invention. The nucleotide sequences of the invention are useful for preparing plants that show increased resistance to soybean pathogens, particularly Asian Soybean Rust (herein, "ASR"). Thus, transformed plants, plant cells, plant tissues and seeds are provided. Compositions include nucleic acids and proteins relating to soybean pathogen resistant plants as well as transformed plants, plant tissues and seeds. Nucleotide sequences of the RG21 and RG22 genes and the amino acid sequences of the proteins encoded thereby are disclosed. The sequences find use in the construction of expression vectors for subsequent transformation into plants of interest, as probes for the isolation of other RG21 and RG22 genes, and the like.

It is possible to produce soybean pathogen resistant plants by inserting into the plant genome a DNA molecule that provides for resistance (Cook et al, 2012 for SCN resistance; Kawashima et al., 2016 for soy rust resistance from pigeon pea).

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), *Glycine* (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Definitions

Unless defined otherwise, all technical and scientific terms used herein have the same meaning as commonly understood to one of ordinary skill in the art to which the presently disclosed subject matter belongs.

Although the following terms are believed to be well understood by one of ordinary skill in the art, the following definitions are set forth to facilitate understanding of the presently disclosed subject matter.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount. As used herein, phrases such as "between about X and Y" mean "between about X and about Y" and phrases such as "from about X to Y" mean "from about X to about Y."

As used herein, phrases such as "between about X and Y", "between about X and about Y", "from X to Y" and "from about X to about Y" (and similar phrases) should be interpreted to include X and Y, unless the context indicates otherwise.

A "coding sequence" is a nucleic acid sequence that is transcribed into RNA such as mRNA, rRNA, tRNA, snRNA, sense RNA or antisense RNA. In embodiments, the RNA is then translated to produce a protein.

As used herein, a "codon optimized" nucleotide sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, a nucleotide sequence is codon optimized for the cell (e.g., an animal, plant, fungal or bacterial cell) in which the construct is to be expressed. For example, a construct to be expressed in a plant cell can have all or parts of its sequence codon optimized for expression in a plant. See, for example, U.S. Pat. No. 6,121,014. In embodiments, the polynucleotides of the invention are codon-optimized for expression in a plant cell (e.g., a dicot cell or a monocot cell) or bacterial cell.

The term "comprise", "comprises" or "comprising," when used in this specification, indicates the presence of the stated features, integers, steps, operations, elements, or components, but does not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim "and those that do not materially alter the basic and novel characteristic(s)" of the claimed invention. Thus, the term "consisting essentially of" when used in a claim of this invention is not intended to be interpreted to be equivalent to "comprising."

"Expression cassette" as used herein means a nucleic acid molecule capable of directing expression of at least one polynucleotide of interest, such as a RG21 or RG22 gene polynucleotide that encodes protein of the invention, in an appropriate host cell, comprising a promoter operably linked to the polynucleotide of interest which is operably linked to a termination signal. An "expression cassette" also typically comprises additional polynucleotides to facilitate proper translation of the polynucleotide of interest. The expression cassette may also comprise other polynucleotides not related to the expression of a polynucleotide of interest but which are present due to convenient restriction sites for removal of the cassette from an expression vector. In embodiments, at least one of the components in the expression cassette may be heterologous (i.e., foreign) with respect to at least one of the other components (e.g., a heterologous promoter operatively associated with a polynucleotide of interest). The expression cassette may also be one that is naturally occurring but has been obtained in a recombinant form useful for heterologous expression. Typically, however, the expression cassette is heterologous with respect to the host, i.e., the expression cassette (or even the polynucleotide of interest) does not occur naturally in the host cell and has been introduced into the host cell or an ancestor cell thereof by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development (as described in more detail herein). An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

The term "introduced" as used herein, in connection to a plant, means accomplished by any manner including but not limited to; introgression, transgenic, Clustered Regularly Interspaced Short Palindromic Repeats modification (CRISPR), Transcription activator-like effector nucleases (TALENs) (Feng et al. 2013, Joung & Sander 2013), meganucleases, or zinc finger nucleases (ZFNs).

As used herein, the term "wild *Glycine*" refers to a perennial *Glycine* plant, for example any one of *G. canescens, G. argyrea, G. clandestine, G. latrobeana, G. albicans, G. aphyonota, G. arenaria, G. curvata, G. cyrtoloba, G. dolichocarpa, G. falcate, G. gracei, G. hirticaulis, G. lactovirens, G. latifolia, G. microphylla, G. montis-douglas, G. peratosa, G. pescadrensis, G. pindanica, G. pulleni, G. rubiginosa, G. stenophita, G. syndetika,* or *G. tomentella.*

As used herein, the term "allele" refers to one of two or more different nucleotides or nucleotide sequences that occur at a specific locus.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced pathogen resistance" refers to a marker whose presence or absence can be used to predict whether and/or to what extent a plant will display a pathogen resistant phenotype.

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-53 (1994). The initial cross gives rise to the F1 generation. The term "BC1" refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval defined by and including," used in reference to particular loci and/or alleles, refers to a chromosomal interval delimited by and encompassing the stated loci/alleles.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "desired allele", "favorable allele" and "allele of interest" are used interchangeably to refer to an allele associated with a desired trait (e.g. ASR resistance).

As used herein, the terms "enhanced pathogen resistance" or "enhanced disease resistance" refers to an improvement, enhancement, or increase in a plant's ability to endure and/or thrive despite being infected with a disease (e.g. Asian soybean rust) as compared to one or more control plants (e.g., one or both of the parents, or a plant lacking a marker associated with enhanced pathogen resistance to respective pathogen/disease). Enhanced disease resistance includes any mechanism (other than whole-plant immunity or resistance) that reduces the expression of symptoms indicative of infection for a respective disease such as Asian soybean rust, soybean cyst nematode, *Pytophthora*, etc.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

An "elite" plant is any plant from an elite line, such that an elite plant is a representative plant from an elite variety. Non-limiting examples of elite soybean varieties that are commercially available to farmers or soybean breeders include: AG00802, A0868, AG0902, A1923, AG2403, A2824, A3704, A4324, A5404, AG5903, AG6202 AG0934; AG1435; AG2031; AG2035; AG2433; AG2733; AG2933; AG3334; AG3832; AG4135; AG4632; AG4934; AG5831; AG6534; and AG7231 (Asgrow Seeds, Des Moines, Iowa, USA); BPRO144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-K2 (NK Division of Syngenta Seeds, Golden Valley, Minnesota, USA); 90M01, 91M30, 92M33, 93M11, 94M30, 95M30, 97B52, P008T22R2; P16T17R2; P22T69R; P25T51R; P34T07R2; P35T58R; P39T67R; P47T36R; P46T21R; and P56T03R2 (Pioneer Hi-Bred International, Johnston, Iowa, USA); SG4771NRR and SG5161NRR/STS (Soygenetics, LLC, Lafayette, Ind., USA); S00-K5, S11-L2, 528-Y2, S43-B1, S53-A1, 576-L9, S78-G6, S0009-M2; S007-Y4; S04-D3; S14-A6; S20-T6; S21-M7; S26-P3; S28-N6; S30-V6; S35-C3; S36-Y6; S39-C4; S47-K5; S48-D9; 552-Y2; S58-Z4; S67-R6; S73-S8; and S78-G6 (Syngenta Seeds, Henderson, Ky., USA); Richer (Northstar Seed Ltd. Alberta, CA); 14RD62 (Stine Seed Co. Ia., USA); or Armor 4744 (Armor Seed, LLC, Ar., USA).

The terms "agronomically elite" as used herein, means a genotype that has a culmination of many distinguishable traits such as emergence, vigor, vegetative vigor, disease resistance, seed set, standability, yield and threshability which allows a producer to harvest a product of commercial significance.

As used herein, the term "commercially significant yield" or "agronomically acceptable yield" refers to a grain yield of at least 100% of a commercial check variety such as AG2703 or DKB23-51.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism.

The terms "nucleic acid," "nucleic acid molecule," "nucleotide sequence," "oligonucleotide" and "polynucleotide" are used interchangeably herein, unless the context indicates otherwise, and refer to a heteropolymer of nucleotides. These terms include without limitation DNA and RNA molecules, including cDNA, genomic DNA, synthetic (e.g., chemically synthesized) DNA and RNA, plasmid DNA, mRNA, anti-sense RNA, and RNA/DNA hybrids, any of which can be linear or branched, single stranded or double stranded, or a combination thereof. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. In embodiments, the "nucleic acid," "nucleic acid molecule,", "nucleotide sequence,", "oligonucleotide" or "polynucleotide" refer to DNA.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to or "operatively associated" with the nucleotide sequence.

As used herein, the terms "disease tolerance" and "disease resistant" refer to a plant's ability to endure and/or thrive despite being infected with a respective disease. When used in reference to germplasm, the terms refer to the ability of a plant that arises from that germplasm to endure and/or thrive despite being infected with a respective disease. In some embodiments, infected Disease resistant soybean plants may yield as well (or nearly as well) as uninfected soybean plants. In general, a plant or germplasm is labeled as "Disease resistant" if it displays "enhanced pathogen resistance."

As used herein, the term "endogenous" refers to materials originating from within an organism or cell. "Exogenous" refers to materials originating from outside of an organism or cell. This typically applies to nucleic acid molecules used in producing transformed or transgenic host cells and plants.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, a "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the term "genome" as it applies to plant cells encompasses not only chromosomal DNA found within the nucleus, but organelle DNA found within subcellular components of the cell. The term "gene" refers to polynucleic acids that comprise chromosomal DNA, plasmid DNA, cDNA, an artificial DNA polynucleotide, or other DNA that is transcribed into an RNA molecule, wherein the RNA may encode a peptide, polypeptide, or protein, and the genetic elements flanking the coding sequence that are involved in the regulation of expression of the mRNA or polypeptide of the present invention. A "fragment" of a gene is a portion of a full-length polynucleic acid molecule that is of at least a minimum length capable of transcription into a RNA, translation into a peptide, or useful as a probe or primer in a DNA detection method.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm may refer to seeds, cells (including protoplasts and calli) or tissues from which new plants may be grown, as well as plant parts that can be cultured into a whole plant (e.g., stems, buds, roots, leaves, etc.).

As used herein, a "Heterologous DNA" sequence refers to a polynucleotide sequence that originates from a foreign source or species or, if from the same source, is modified from its original form.

As used herein, a "Homologous DNA" refers to DNA from the same source as that of the recipient cell.

As used herein, the term "hybrid" refers to a seed and/or plant produced when at least two genetically dissimilar parents are crossed.

As used herein, the term "Identity" refers to the degree of similarity between two polynucleic acid or protein sequences. An alignment of the two sequences is performed by a suitable algorithm. One widely used and accepted computer program for performing sequence alignments is CLUSTALW v1.6 (Thompson, et al. Nucl. Acids Res., 22: 4673-4680, 1994), although others are commonly used. The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between 200 and 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity. In addition to identity positions, consensus positions are also commonly scored. Consensus amino acids are those known to have similar amino acid properties such as charge, size, polarity, and aromaticity.

As used herein, the term "inbred" refers to a substantially homozygous plant or variety. The term may refer to a plant or variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced ASR tolerance may be introgressed from a donor into a recurrent parent that is not disease resistant. The resulting offspring could then be repeatedly backcrossed and selected until the progeny possess the ASR tolerance allele(s) in the recurrent parent background.

As used herein, an "isolated" nucleic acid molecule is substantially separated away from other nucleic acid sequences with which the nucleic acid is normally associated, such as, from the chromosomal or extrachromosomal DNA of a cell in which the nucleic acid naturally occurs. A nucleic acid molecule is an isolated nucleic acid molecule when it comprises a transgene or part of a transgene present in the genome of another organism. The term also embraces nucleic acids that are biochemically purified so as to substantially remove contaminating nucleic acids and other cellular components. The term "transgene" refers to any polynucleic acid molecule normative to a cell or organism transformed into the cell or organism. "Transgene" also encompasses the component parts of a native plant gene modified by insertion of a normative polynucleotide molecule by directed recombination or site specific mutation.

A polypeptide is "isolated" if it has been separated from the cellular components (nucleic acids, lipids, carbohydrates, and other polypeptides) that naturally accompany it or that is chemically synthesized or recombinant. A polypeptide molecule is an isolated polypeptide molecule when it is expressed from a transgene in another organism. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Proteins can be purified by any of the means known in the art, for example as described in Guide to Protein Purification, ed. Deutscher, Meth. Enzymol. 185, Academic Press, San Diego, 1990; and Scopes, Protein Purification: Principles and Practice, Springer Verlag, N.Y., 1982.

Using well-known methods, the skilled artisan can readily produce nucleotide and amino acid sequence variants of genes and proteins that provide a modified gene product. Chemical synthesis of nucleic acids can be performed, for example, on automated oligonucleotide synthesizers. Such variants preferably do not change the reading frame of the protein-coding region of the nucleic acid. The present invention also encompasses fragments of a protein that lacks at least one residue of a full-length protein, but that substantially maintains activity of the protein.

A "locus" is a position on a chromosome where a gene or marker or allele is located. In some embodiments, a locus may encompass one or more nucleotides.

A "non-naturally occurring variety of soybean" is any variety of soybean that does not naturally exist in nature. A "non-naturally occurring variety of soybean" may be produced by any method known in the art, including, but not limited to, transforming a soybean plant or germplasm, transfecting a soybean plant or germplasm and crossing a naturally occurring variety of soybean with a non-naturally occurring variety of soybean. In some embodiments, a "non-naturally occurring variety of soybean" may comprise one of more heterologous nucleotide sequences. In some embodiments, a "non-naturally occurring variety of soybean" may comprise one or more non-naturally occurring copies of a naturally occurring nucleotide sequence (i.e., extraneous copies of a gene that naturally occurs in soybean). In some embodiments, a "non-naturally occurring variety of soybean" may comprise a non-natural combination of two or more naturally occurring nucleotide sequences (i.e., two or more naturally occurring genes that do not naturally occur in the same soybean, for instance genes not found in *Glyane max* lines).

As used herein, the terms "phenotype," "phenotypic trait" or "trait" refer to one or more traits and/or manifestations of an organism. The phenotype can be a manifestation that is observable to the naked eye, or by any other means of evaluation known in the art, e.g., microscopy, biochemical analysis, or an electromechanical assay. In some cases, a phenotype or trait is directly controlled by a single gene or genetic locus, i.e., a "single gene trait." In other cases, a phenotype or trait is the result of several genes. It is noted that, as used herein, the term "disease resistant phenotype" takes into account environmental conditions that might affect the respective disease such that the effect is real and reproducible.

As used herein, the term "plant" may refer to a whole plant, any part thereof, or a cell or tissue culture derived from a plant. Thus, the term "plant" can refer to any of: whole plants, plant components or organs (e.g., roots, stems, leaves, buds, flowers, pods, etc.), plant tissues, seeds and/or plant cells. A plant cell is a cell of a plant, taken from a plant, or derived through culture from a cell taken from a plant. Thus, the term "soybean plant" may refer to a whole soybean plant, one or more parts of a soybean plant (e.g., roots, root tips, stems, leaves, buds, flowers, pods, seeds, cotyledons, etc.), soybean plant cells, soybean plant protoplasts and/or soybean plant calli.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant. In embodiments, the plant cell is non-propagating and/or cannot regenerate a whole plant.

A "plant cell culture" means a culture of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, the term "plant part" includes but is not limited to embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to a DNA amplification method that uses an enzymatic technique to create multiple copies of one sequence of nucleic acid (amplicon). Copies of a DNA molecule are prepared by shuttling a DNA polymerase between two amplimers. The basis of this amplification method is multiple cycles of temperature changes to denature, then re-anneal amplimers (DNA primer molecules), followed by extension to synthesize new DNA strands in the region located between the flanking amplimers. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method known in the art. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066. Primers can be labeled, if desired, by incorporating detectable moieties by for instance spectroscopic, fluorescence, photochemical, biochemical, immunochemical, or chemical moieties. Primers diagnostic (i.e. able to identify or select based on presence of ASR resistant alleles) for ASR resistance can be created to any favorable SNP as described in any one of Tables 1-5. The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). Molecular Cloning: A Laboratory Manual, Third Edition, Cold Spring Harbor Laboratory Press, Cold Spring Harbor, New York, U.S.A. Generally, lower salt concentration and higher temperature hybridization and/or washes increase the stringency of hybridization conditions.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

The term "promoter" or "promoter region" refers to a polynucleic acid molecule that functions as a regulatory element, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant DNA construct, as demonstrated by its ability to produce mRNA.

A "recombinant" nucleic acid is made by a combination of two otherwise separated segments of nucleic acid sequence, for example, by chemical synthesis or by the manipulation of isolated segments of polynucleic acids by genetic engineering techniques. The term "recombinant DNA construct" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs may be constructed to be capable of expressing antisense RNAs, or stabilized double stranded antisense RNAs.

The phrase "substantially identical," in the context of two nucleic acids or two amino acid sequences, refers to two or more sequences or subsequences that have at least about 50% nucleotide or amino acid residue identity when compared and aligned for maximum correspondence as measured using a sequence comparison algorithm or by visual inspection. In certain embodiments, substantially identical sequences have at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more nucleotide or amino acid residue identity. In certain embodiments, substantial identity exists over a region of the sequences that is at least about 50 amino acid residues, 100 amino acid residues, 150 amino acid residues, 200 amino acid residues, 250 amino acid residues, 300 amino acid residues, 350 amino acid residues, 400 amino acid residues, 450 amino acid residues, 500 amino acid residues, 525 amino acid residues, 526, amino acid residues 527 amino acid residues, 528 amino acid residues, 529 amino acid residues, 530 amino acid residues, 531 amino acid residues, 532 amino acid residues, 533 amino acid residues, 534 amino acid residues, 535 amino acid residues, 536 amino acid residues or more with respect to the protein sequence or the nucleotide sequence encoding the same. In further embodiments, the sequences are substantially identical when they are identical over the entire length of the coding regions.

"Identity" or "percent identity" refers to the degree of identity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215: 403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules. As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

As used herein, "specifically" or "selectively" hybridizing (and similar terms) refers to the binding, duplexing, or hybridizing of a molecule to a particular nucleic acid target sequence under stringent conditions when that sequence is present in a complex mixture (e.g., total cellular DNA or RNA) to the substantial exclusion of non-target nucleic acids, or even with no detectable binding, duplexing or hybridizing to non-target sequences. Specifically or selectively hybridizing sequences typically are at least about 40% complementary and are optionally substantially complementary or even completely complementary (i.e., 100% identical).

For DNA-DNA hybrids, the $T_m$ can be approximated from the equation of Meinkoth and Wahl, Anal. Biochem., 138: 267-84 (1984): $T_m$=81.5° C.+16.6 (log M)+0.41 (% GC)−0.61 (% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired degree of identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, highly stringent conditions can utilize a hybridization and/or wash at the thermal melting point ($T_m$) or 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). If the desired degree of mismatching results in a $T_m$ of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2× SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M NaPO$_4$, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced.

Expression of RG21 and RG22 Gene Coding Sequences in Plants

DNA constructs were made that contain various genetic elements necessary for the expression of the RG21 and RG22 gene coding sequences in plants. "DNA construct" refers to the heterologous genetic elements operably linked to each other making up a recombinant DNA molecule and may comprise elements that provide expression of a DNA polynucleotide molecule in a host cell and elements that provide maintenance of the construct in the host cell. A plant expression cassette comprises the operable linkage of genetic elements that when transferred into a plant cell provides expression of a desirable gene product. "Plant expression cassette" refers to chimeric DNA segments comprising the regulatory elements that are operably linked to provide the expression of a transgene product in plants. Promoters, leaders, introns, transit peptide encoding polynucleic acids, 3' transcriptional termination regions are all genetic elements that may be operably linked by those skilled in the art of plant molecular biology to provide a desirable level of expression or functionality to an RG21 or RG22 gene of the present invention. A DNA construct can contain one or more plant expression cassettes expressing the DNA molecules of the present invention or other DNA molecules useful in the genetic engineering of crop plants.

A variety of promoters specifically active in vegetative tissues, such as leaves, stems, roots and tubers, can be used to express the RG21 and/or RG22 gene polynucleic acid molecules of the present invention.

The translation leader sequence means a DNA molecule located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders, plant virus coat protein leaders, plant rubisco gene leaders among others (Turner and Foster, Molecular Biotechnology 3:225, 1995).

The "3' non-translated sequences" means DNA sequences located downstream of a structural polynucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3'; Fraley et al., Proc. Natl. Acad. Sci. USA 80: 4803-4807, 1983). The use of different 3' non-translated sequences is exemplified by Ingelbrecht et al., Plant Cell 1:671-680, 1989.

The laboratory procedures in recombinant DNA technology used herein are those well-known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al. (1989).

The DNA construct of the present invention may be introduced into the genome of a desired plant host by a variety of conventional transformation techniques that are well known to those skilled in the art. "Transformation" refers to a process of introducing an exogenous polynucleic acid molecule (for example, a DNA construct, a recombinant polynucleic acid molecule) into a cell or protoplast and that exogenous polynucleic acid molecule is incorporated into a host cell genome or an organelle genome (for example, chloroplast or mitochondria) or is capable of autonomous replication. "Transformed" or "transgenic" refers to a cell, tissue, organ, or organism into which a foreign polynucleic acid, such as a DNA vector or recombinant polynucleic acid molecule, has been inserted. A "transgenic" or "transformed" cell or organism also includes progeny of the cell or organism and progeny produced from a breeding program employing such a "transgenic" plant as a parent in a cross and exhibiting an altered phenotype resulting from the presence of the foreign polynucleic acid molecule.

Methods of transformation of plant cells or tissues include, but are not limited to Agrobacterium mediated transformation method and the Biolistics or particle-gun mediated transformation method. Suitable plant transformation vectors for the purpose of Agrobacterium mediated transformation include-those elements derived from a tumor inducing (Ti) plasmid of Agrobacterium tumefaciens, for example, right border (RB) regions and left border (LB) regions, and others disclosed by Herrera-Estrella et al., Nature 303:209 (1983); Bevan, Nucleic Acids Res. 12:8711-8721 (1984); Klee et al., Bio-Technology 3(7):637-642 (1985). In addition to plant transformation vectors derived from the Ti or root-inducing (Ri) plasmids of Agrobacterium, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

DNA constructs can be prepared that incorporate the RG21 gene coding sequences of the present invention for use in directing the expression of the sequences directly from the host plant cell plastid. Examples of such constructs suitable for this purpose and methods that are known in the art and are generally described, for example, in Svab et al., Proc. Natl. Acad. Sci. USA 87:8526-8530, (1990) and Svab et al., Proc. Natl. Acad. Sci. USA 90:913-917 (1993) and in U.S. Pat. No. 5,693,507.

When adequate numbers of cells containing the exogenous polynucleic acid molecule encoding polypeptides from the present invention are obtained, the cells can be cultured, then regenerated into whole plants. "Regeneration" refers to the process of growing a plant from a plant cell (for example, plant protoplast or explant). Such regeneration techniques rely on manipulation of certain phytohormones in a tissue culture growth medium, typically relying on a biocide and/or herbicide marker that has been introduced together with the desired nucleotide sequences. Choice of methodology for the regeneration step is not critical See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Such regeneration techniques are described generally in Klee et al., Ann. Rev. Plant Phys. 38:467-486 (1987).

The development or regeneration of transgenic plants containing the exogenous polynucleic acid molecule that encodes a polypeptide of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants.

Disease Resistant Soybean Plants and Germplasms

The present invention provides disease resistant soybean plants and germplasms. A disease resistant soybean plant or germplasm may be produced by any method whereby at least one of an RG21 gene and an RG22 gene is introduced into the soybean plant or germplasm, including, but not limited to, transformation, protoplast transformation or fusion, a double haploid technique, wide crosses e.g. with embryo rescue, gene editing and/or by any other nucleic acid transfer system.

In some embodiments, the soybean plant or germplasm comprises a non-naturally occurring variety of soybean. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The disease resistant soybean plant or germplasm may be the progeny of a cross between an elite variety of soybean and a variety of soybean that comprises an RG21 and gene encoding a protein having at least 70%-100% sequence identity to SEQ ID NO: 1, or an RG21 gene encoding a protein having at least 70%-100% sequence identity to SEQ ID NO: 12. In many examples, embodiments will have at least one of at least 80% 85%, 90%, 91%, 92%, 93%, 94%, 95%, 96%, 97%, 98%, or 99% identity to any of SEQ ID NO:1 or SEQ ID NO: 12.

The disease resistant soybean plant or germplasm may be the progeny of an introgression wherein the recurrent parent is an elite variety of soybean and the donor comprises an RG21 and/or an RG22 gene associated with enhanced disease tolerance and/or resistance wherein the donor carries a RG21 gene having between 70-100% identity to SEQ ID NO: 2 and/or and RG22 gene having between 70-100% identity to SEQ ID NO: 13.

The disease resistant soybean plant or germplasm may be the progeny of a cross between a first elite variety of soybean (e.g., a tester line) and the progeny of a cross between a second elite variety of soybean (e.g., a recurrent parent) and a variety of soybean that comprises at least one of an RG21 gene and an RG22 gene.

Disease Resistant Soybean Seeds

The present invention provides disease resistant soybean seeds. As discussed above, the methods of the present invention may be utilized to identify, produce and/or select a disease resistant soybean seed. In addition to the methods described above, a disease resistant soybean seed may be produced by any method whereby at least one of an RG21 gene and an RG22 gene is introduced into the soybean seed, including, but not limited to, transformation, protoplast transformation or fusion, a double haploid technique, embryo rescue, genetic editing (e.g. CRISPR or TALEN or MegaNucleases) and/or by any other nucleic acid transfer system.

In some embodiments, the disease resistant soybean seed comprises a non-naturally occurring variety of soybean. In some embodiments, the soybean seed is at least about 50%, 55%, 60%, 65%, 70%, 75%, 80%, 85%, 90%, 95%, 97%, 99% or 100% identical to that of an elite variety of soybean.

The disease resistant soybean seed may be produced by a disease resistant soybean plant identified, produced or selected by the methods of the present invention.

A disease resistant soybean seed of the present invention may comprise, be selected by or produced by use of one or more RG21 or RG21 genes of the present invention.

The current disclosure also includes methods of selecting a *Glycine max* plant comprising at least one of an RG21 gene and an RG22 gene conferring resistance to ASR. In typical embodiments, methods comprise, isolating at least one of nucleic acids or proteins from a *Glycine max* plant; detecting in the nucleic acids or proteins a marker associated with the RG21 gene, and selecting a *Glycine max* plant comprising one or more of the markers, thereby selecting a plant having increased resistance to ASR. Markers can include a PCR based-marker (e.g. Taqman for SNP detection or amplification of the RG21 gene or a portion thereof), when detection occurs in an isolated nucleic acid sample. Markers can also include immunoassay-based markers (e.g. ELISA) when detection occurs in an isolated protein sample. Accordingly, the current disclosure is also directed to compositions for detecting markers associated with the RG21 and RG22 genes. For example, the compositions can include primer pairs (e.g. for detecting based on gene, or a portion thereof, amplification); primer pairs and probes (e.g. for detecting based on SNPs); or anti-RG21 antibodies (e.g. anti-RG21 rabbit or goat antibodies for detecting using an immunoassay based method such as ELISA).

EXAMPLES

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

Example 1: Construction of Vectors Comprising RG21 Genes

Vector 25307 (SEQ ID NO: 3), illustrated in FIG. 1, was constructed containing an RG21 gene (SEQ ID NO: 2) and *G. tomentella* promoter (SEQ ID NO: 7). Features and position are escribed below:

cGtoRG21-01 (Start: 2217 End: 5987) is the CDS sequence of R-gene cGtoRG21 derived from *G. tomentella* PI499939, featuring coiled-coil, nucleotide binding, and leucine rich repeat domains (CNL), syntenic to a gene located on *G. max* chromosome 20. Introns were removed in the CDS.

cNtALS-01 (Start: 9387 End: 11381) fragment encodes an Acetolactate synthase double mutant codon-optimized for soybean expression.

cSpec-03 (Start: 12731 End: 13519) also called aadA, is a gene encoding the enzyme aminoglycoside 3' adenyltransferase that confers resistance to spectinomycin and streptomycin for maintenance of the vector in *E. coli* and *Agrobacterium*.

cVirG-01 (Start: 13819 End: 14544).
cRepA-03 (Start: 14574 End: 15647).

bNRB-04 (Start: 4 End: 143) right border region of T-DNA of *Agrobacterium tumefaciens* nopaline ti-plasmid.

bNRB-01-01 (Start: 101 End: 125) right border repeat.

bNLB-05 (Start: 12322 End: 12451) left border region of T-DNA of *Agrobacterium tumefaciens* nopaline ti-plasmid.

bNLB-01-01 (Start: 12357 End: 12381) 25 bp Left border repeat region of T-DNA of *Agrobacterium tumefaciens* nopaline ti-plasmid.

iGmEF-02 (Start: 8459 End: 9367) the first intron of the soybean elongation factor (EF) gene.

gGtoRG21-01 (Start: 217 End: 7293) genomic fragment harboring RG21 soy rust resistance gene from *G. tomentella* PI499939 featuring coiled-coil, nucleotide binding and leucine rich repeat domains (CNL), syntenic to a gene located on *G. max* chromosome 20, with expression driven by the native promoter and terminator region.

xTAG-06 (Start: 144 End: 183) 40 bp site for plant insert intactness testing and to stop readthrough ORFs.

xSTOPS-01 (Start: 184 End: 195) 6-frame stop to minimize unintended ORF read-through.

START (Start: 2217 End: 2219).

STOP (Start: 5985 End: 5987).

xSTOPS-01 (Start: 7301 End: 7312) 6-frame stop to minimize unintended ORF read-through.

Start (Start: 8396 End: 8396) transcription start site.

xSTOPS-01 (Start: 12186 End: 12197) 6-frame stop to minimize unintended ORF read-through.

xSTOPS-01 (Start: 12262 End: 12273) 6-frame stop to minimize unintended ORF read-through.

xTAG-02 (Start: 12274 End: 12313) 40 bp site for plant insert intactness testing and to stop readthrough ORFs.

promoter_GtoRG21 (Start: 217 End: 1946).

prGmEF-05 (Start: 7313 End: 9378).

prVirG-01 (Start: 13614 End: 13744) virG promoter.

oVS1-02 (Start: 15690 End: 16094) origin of replication and partitioning region from plasmid, serves as origin of replication in *Agrobacterium tumefaciens* host.

oCOLE-06 (Start: 16772 End: 17578) the ColE1 origin of replication functional in *E. coli*.

Terminator_RG21 (Start: 6294 End: 7293).

tGmEPSPS-04 (Start: 11388 End: 12185) modified version of tGMEPS-02; an EPSPS terminator from *Glycine max*.

3'UTR_RG21 (Start: 6025 End: 6293).

5'UTR_RG21 (Start: 1948 End: 2216).

u5GmEF-01 (Start: 8396 End: 8458)

u5GmEF-02 (Start: 9368 End: 9378)

Example 2: Validation of RG21 Genes Against ASR

Numerous soybeans events were created using the vector of Example 1. Leaves from primary events were placed in a petri dish on moist paper towel then inoculated with a spore suspension of 6 different rust races. After 14 days, these leaves were evaluated for resistance.

Figure 2:
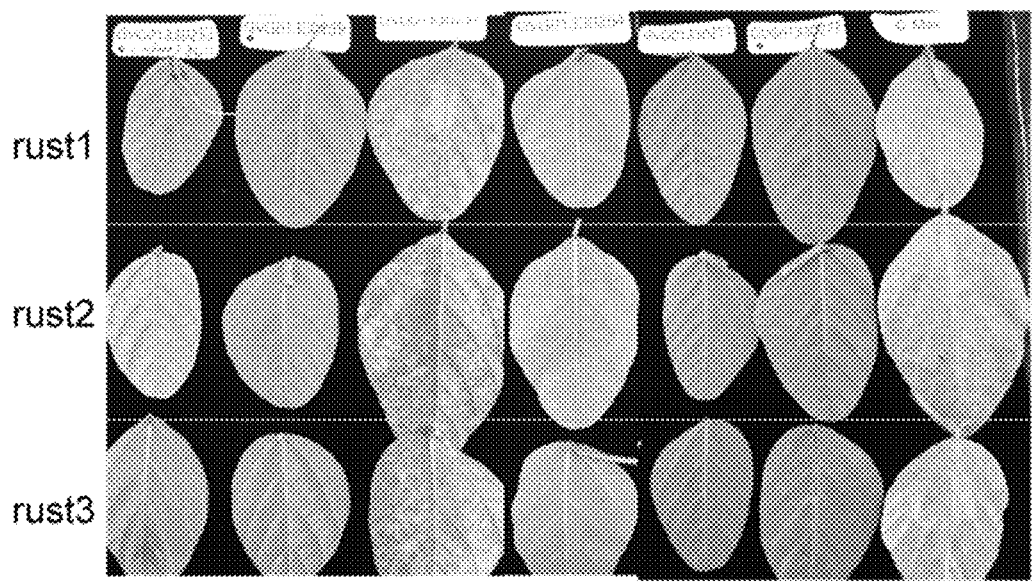
FIG. 2 shows photographs of rust bioassay experiments conducted on leaves collected from primary soybean events generated from vector 25307.

More than half of the events tested provide strong resistance >90% or more protection compared to wild type soybean. Of these events, over half show near complete immune response to 6 out of 6 tested rusts. FIG. 2 is an illustrative photograph, showing results from 3 of the 6 rust races tested. Leaves from wild type soybean plants served as negative controls.

Figure 3:
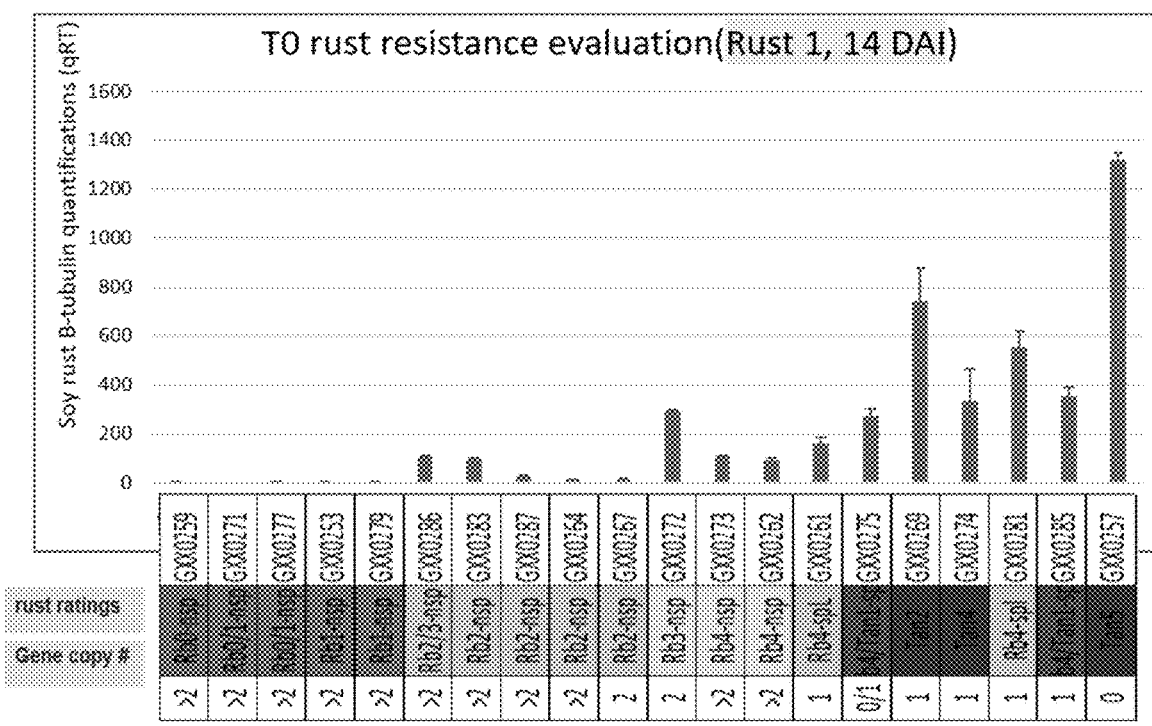
FIG. 3 is a graph showing bioassay fungal biomass quantification results for rust1.
Figure 4:
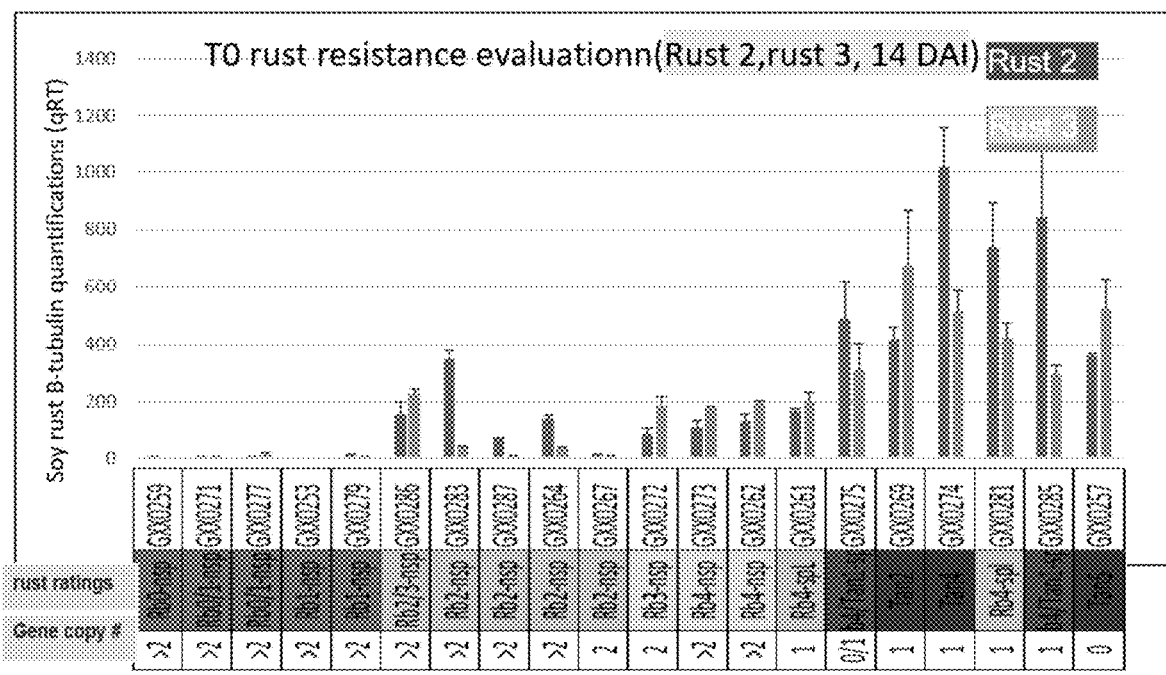
FIG. 4 is a graph showing bioassay fungal biomass quantification results for rust2 and rust3.

In order to quantify the level of disease resistance, these leaves were sampled for qRT-PCR analysis to quantify the relative expression of soybean rust β-tubulin gene. FIG. 3 illustrates the quantification for rust1, including resistance rating and gene copy. FIG. 4 illustrates the quantification for rusts 2 and 3, including resistance rating and gene copy. As seen, there is no or little detectable fungal biomass at 14 days after infection (green events in the graph or the first 10 events from left to right in both FIG. 3 and FIG. 4). This is reproducibly shown by the same set of events and additional TO events. Some TO detached leaf assays were extended to 18 days, and in these we also observed strong resistance throughout the entire experiment.

In this experiment, strong resistance is detected in events with >2 gene copies (green events in the graph) and events with 1 copy are generally partially susceptible. However, qRT of trait gene indicate low expression in majority of the events, so resistance does not appear to require high expression levels.

Example 3: Construction of Additional Vectors

Figure 5:
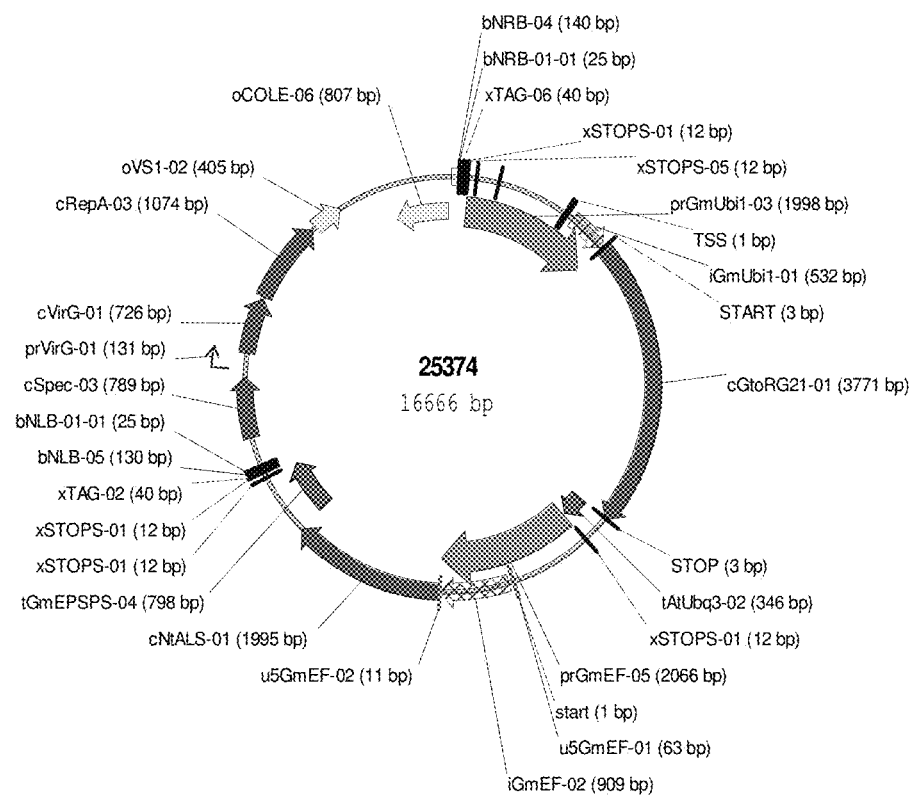
FIG. 5 is an illustration of vector 25374.
Figure 6:
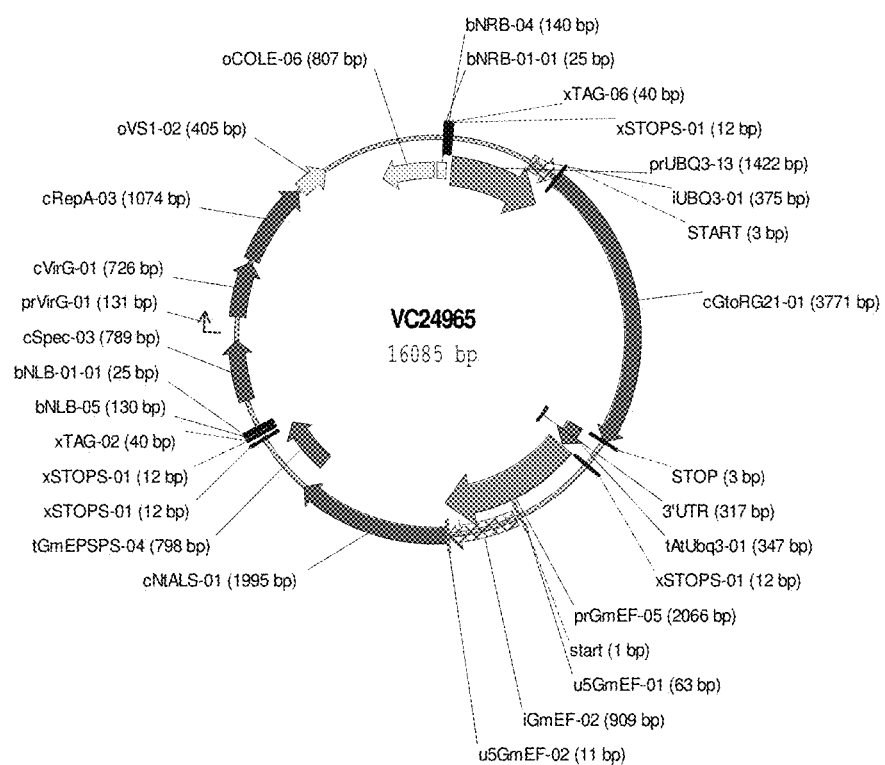
FIG. 6 is an illustration of vector VC24965.
Figure 7:
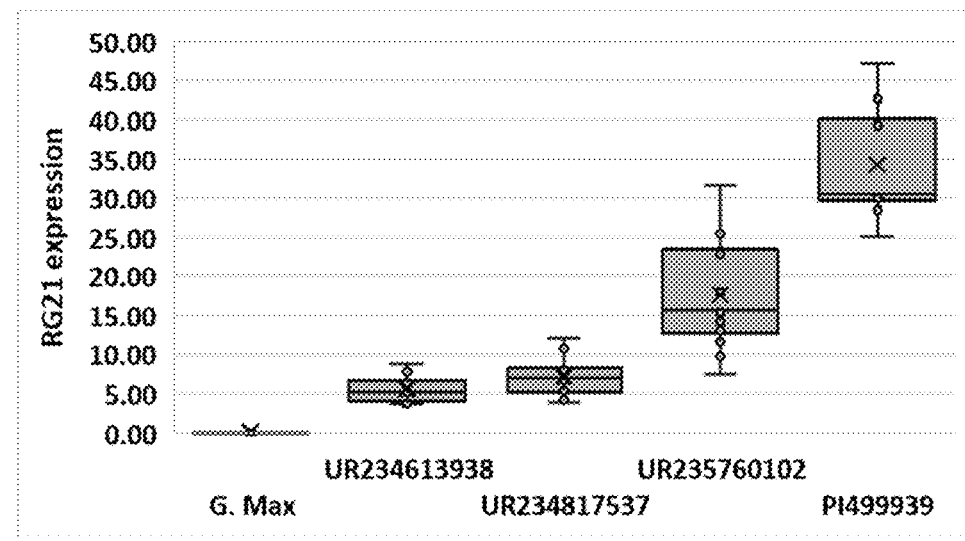
FIG. 7 is a graph showing relative expression (y-axis) of the RG21 gene, including in transgenic *Glycine max* containing the RG21 gene and in *Glycine max* not containing the RG21 gene.
Figure 8:
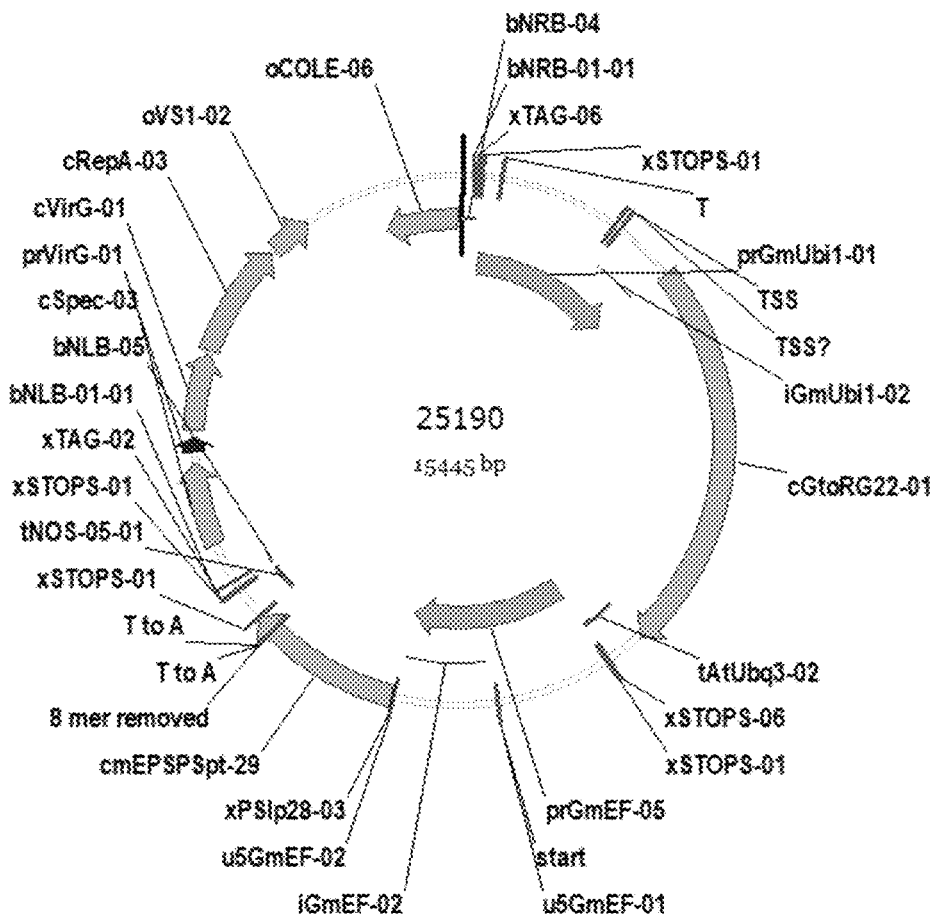
FIG. 8 is an illustration of vector 25190 containing an RG22 gene.
Figure 9:
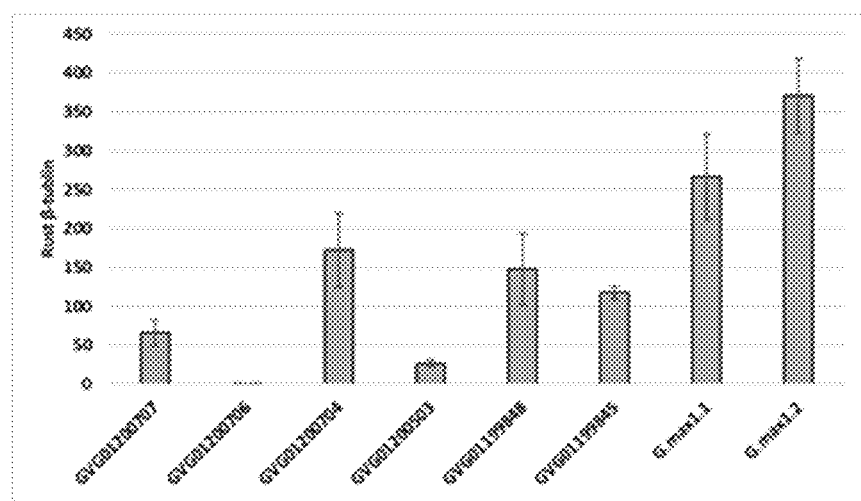
FIG. 9 is a graph showing shows rust quantification obtained from several primary soybean events generated from vector 25190.

Vector 25374 (SEQ ID NO: 4), illustrated in FIG. 5, and Vector 24965 (SEQ ID NO: 5), illustrated in FIG. 6 were also constructed using different promoters (prGmUbi and prUBQ3, respectively). These vectors were created to illustrate increased gene expression.

Features of Vector 25374 are as follows:

cGtoRG21-01 (Start: 2239 End: 6009) CDS sequence of synthetic R-gene cGtoRG21 derived from *G. tomentella* PI499939, featuring coiled-coil, nucleotide binding, and leucine rich repeat domains (CNL), syntenic to a gene located on *G. max* chromosome 20. Introns were removed in the CDS.

cNtALS-01 (Start: 8463 End: 10457) NtALS DNA fragment encodes an Acetolactate synthase double mutant, codon-optimized for soybean expression.

cSpec-03 (Start: 11807 End: 12595) gene encoding the enzyme aminoglycoside 3'adenyltransferase that confers resistance to spectinomycin and streptomycin for maintenance of the vector in *E. coli* and *Agrobacterium*.

cVirG-01 (Start: 12895 End: 13620) virG.

cRepA-03 (Start: 13650 End: 14723).

bNRB-04 (Start: 4 End: 143) right border region of T-DNA of *Agrobacterium tumefaciens* nopaline ti-plasmid.

bNRB-01-01 (Start: 101 End: 125) Right Border Repeat.

bNLB-05 (Start: 11398 End: 11527) Left border region of T-DNA of *Agrobacterium tumefaciens* nopaline ti-plasmid.

bNLB-01-01 (Start: 11433 End: 11457) 25 bp Left border repeat region of T-DNA of *Agrobacterium tumefaciens* nopaline ti-plasmid.

iGmUbi1-01 (Start: 1695 End: 2226) the 5' UTR intron as found in prGmUbi1-02.

iGmEF-02 (Start: 7535 End: 8443) the first intron of the soybean elongation factor (EF) gene with an internal BamHI site and a 3' end unintended ORF removed.

xTAG-06 (Start: 144 End: 183) 40 bp site for plant insert intactness testing and to stop readthrough ORFs.

xSTOPS-01 (Start: 184 End: 195) 6-frame stop to minimize unintended ORF read-through.

xSTOPS-05 (Start: 217 End: 228) 6-frame stop to minimize unintended ORF read-through.

TSS (Start: 1571 End: 1571) Transcription starting site.

START (Start: 2239 End: 2241).

STOP (Start: 6007 End: 6009).

xSTOPS-01 (Start: 6377 End: 6388) 6-frame stop to minimize unintended ORF read-through.

Start (Start: 7472 End: 7472).

xSTOPS-01 (Start: 11262 End: 11273) 6-frame stop to minimize unintended ORF read-through.

xSTOPS-01 (Start: 11338 End: 11349) 6-frame stop to minimize unintended ORF read-through.

xTAG-02 (Start: 11350 End: 11389) 40 bp site for plant insert intactness testing and to stop readthrough ORFs.

prGmUbi1-03 (Start: 229 End: 2226) promoter.

prGmEF-05 (Start: 6389 End: 8454) translation elongation factor EF-1 alpha/Tu promoter, including the first intron and neighboring utr, from soybean (williams 82).

prVirG-01 (Start: 12690 End: 12820) virG promoter composed of two promoter elements, one responsive to acetosyringone and phosphate-starvation (bp 45 to 83) and another to medium acidification (86 to 128).

oVS1-02 (Start: 14766 End: 15170) serves as origin of replication in *Agrobacterium tumefaciens* host.

oCOLE-06 (Start: 15848 End: 16654) the ColE1 origin of replication functional in *E. coli* tAtUbq3-02 (Start: 6016 End: 6361) terminator.

tGmEPSPS-04 (Start: 10464 End: 11261) a terminator derived from *Glycine max*.

u5GmEF-01 (Start: 7472 End: 7534) first 5' UTR of the soybean elongation factor (EF) gene.

u5GmEF-02 (Start: 8444 End: 8454) Second 5' UTR of the soybean elongation factor (EF) gene.

Features of Vector 24965 are as follows:

cGtoRG21-01 (1658 End: 5428) CDS sequence of synthetic R-gene cGtoRG21 derived from *G. tomentella* PI499939, featuring coiled-coil, nucleotide binding, and leucine rich repeat domains (CNL), syntenic to a gene located on *G. max* chromosome 20. Introns were removed in the CDS.

cNtALS-01 (Start7882 End: 9876) NtALS DNA fragment encodes an Acetolactate synthase double mutant, codon-optimized for soybean expression.

cSpec-03 (Start: 11226 End: 12014) gene encoding the enzyme aminoglycoside 3'adenyltransferase that confers resistance to spectinomycin and streptomycin for maintenance of the vector in *E. coli* and *Agrobacterium*.

cVirG-01 (12314 End: 13039) virG.

cRepA-03 (13069 End: 14142).

bNRB-04 (Start: 4 End: 143) right border region of T-DNA of *Agrobacterium tumefaciens* nopaline ti-plasmid.

bNRB-01-01 (Start: 101 End: 125) Right Border Repeat.

bNLB-05 (Start: 10817 End: 10946) Left border region of T-DNA of *Agrobacterium tumefaciens* nopaline ti-plasmid.

bNLB-01-01 (Start: 10852 End: 10876) 25 bp Left border repeat region of T-DNA of *Agrobacterium tumefaciens* nopaline ti-plasmid.

iUBQ3-01 (Start: 1268 End: 1642) UBQ3 intron.

iGmEF-02 (Start: 6954 End: 7862) the first intron of the soybean elongation factor (EF) gene with an internal BamHI site and a 3' end unintended ORF removed.

xTAG-06 (Start: 144 End: 183) 40 bp site for plant insert intactness testing and to stop readthrough ORFs.

xSTOPS-01 (Start: 184 End: 195) 6-frame stop to minimize unintended ORF read-through.

xSTOPS-05 (Start: 217 End: 228) 6-frame stop to minimize unintended ORF read-through.

START (Start: 1658 End: 1660).

STOP (Start: 5426 End: 5428).

xSTOPS-01 (Start: 5796 End: 5807) 6-frame stop to minimize unintended ORF read-through.

Start (Start: 6891 End: 6891).

xSTOPS-01 (Start: 10757 End: 10768) 6-frame stop to minimize unintended ORF read-through.

xSTOPS-01 (Start: 10681 End: 10692) 6-frame stop to minimize unintended ORF read-through.

xTAG-02 (Start: 10769 End: 10808) 40 bp site for plant insert intactness testing and to stop readthrough ORFs.

prUBQ3-13 (Start: 221 End: 1642) promoter derived from Arabidopsis Ubiquitin3.

prGmEF-05 (Start: 5808 End: 7873) translation elongation factor EF-1 alpha/Tu promoter, including the first intron and neighboring utr, from soybean (williams 82).

prVirG-01 (Start: 12109 End: 12239) virG promoter composed of two promoter elements, one responsive to acetosyringone and phosphate-starvation (bp 45 to 83) and another to medium acidification (86 to 128).

oVS1-02 (Start: 14185 End: 14589) serves as origin of replication in *Agrobacterium tumefaciens* host.

oCOLE-06 (Start: 15267 End: 16073) the ColE1 origin of replication functional in *E. coli* tAtUbq3-01 (Start: 5435 End: 5781) terminator.

tGmEPSPS-04 (Start: 9883 End: 10680) a terminator derived from *Glycine* max.

u5GmEF-01 (Start: 6891 End: 6953) first 5' UTR of the soybean elongation factor (EF) gene.

u5GmEF-02 (Start: 7863 End: 7873) Second 5' UTR of the soybean elongation factor (EF) gene.

Example 4: Introgression of RG21 Gene into *Glycine max* Lines through Embryo Rescue Non-naturally occurring mutant soybean lines were created by chemically introgressing the exogenous gene RG21 from *G. tomentella* PI499939 or F2:3 progeny of PI499939. Embryo rescue is performed and chemical treatment is applied in order to generate amphidiploid shoots. If the amphidiploid plants are fertile they will be used to backcross with *G. max*. Backcrossing with *G. max* and subsequent embryo rescue will need to be performed for several generations in order to gradually eliminate the perennial wild *Glycine* chromosomes.

Wide crosses: Elite Syngenta soybean lines (RM 3.7 to 4.8) were used as the females (pollen recipients) and multiple *G. tomentella* was used as the males or pollen donors. Selecting flowers from the *Glycine* plant containing anthers at the proper developmental stage is important. New, fully-opened, brightly colored flowers hold anthers with mature pollen. The pollen should appear as loose, yellow dust. These flowers are removed from the *Glycine* plant and taken to the soybean plant for pollination. Pollen from the *Glycine* plants should be used within 30 minutes of flower removal. It is also important to identify and select soybean flower buds that are ready for pollination. A soybean flower bud is generally ready when it is larger in size when compared to an immature bud. The sepals of the soybean blossoms are lighter in color and the petals are just beginning to appear. First, use a pair of fine-tipped tweezers to carefully detach the sepals from the flower bud to expose the outer set of petals. Then gently grasp and remove the petals (5 in total) from the flower exposing the ring of stamens surrounding the pistil. Since the stigma is receptive to pollen 1 day before the anthers begin shedding pollen it is important to recognize the stage development of "female ready, male not ready". When pollinating soybean flowers at this developmental stage it is not necessary to emasculate the female flower. Locate the stigma on the soybean flower. Then using 1 male flower, carefully peel off the petals to expose the anthers and gently dust the pollen grains onto the stigma of the soybean flower. Care should be taken not to damage the stigma at any time during this process. Starting the day after pollination a hormone mixture is sprayed onto the pollinated flower and eventual developing F1 pod 1× every day until harvest. The pollinated flower or pod is saturated with a light mist of the hormone mixture, taking care not to cause the flower/pod to prematurely detach from the plant. The mixture contains 100 mg GA3, 25 mg NAA and 5 mg kinetin/L distilled water. These hormones aid in the retention of the developing pod and in increased pod growth.

Harvest: Pods from wide crosses are harvested at approximately 14 to 16 days post pollination. (Harvest dates in the literature suggest 19 to 21 days.) Before selecting an individual pod to harvest verify that the sepals were removed (this indicates a wide cross attempt) and that the seed size is as expected for a wide cross. Pods are collected and counted according to wide cross combination to determine crossing success. The wide cross pods can contain 1 to 3 seeds but generally 2 seeds are found in each F1 pod.

Embryo rescue: Harvested pods are collected and brought back to the lab to be sterilized. The pods are first rinsed with 70% EtOH for 2 to 3 minutes and then placed in 10% Clorox bleach for an additional 30 minutes on a platform shaker at approximately 130 RPM. Finally, the pods are rinsed multiple times with sterile water to remove any residual bleach. Embryo isolation can begin immediately following pod sterilization or pods can be stored at 4° C. for up to 24 hours prior to embryo isolation. The sterilized pods are next taken to a laminar flow hood where the embryos can be rescued. Individual pods are placed in a sterile petri dish and opened using a scalpel and forceps. An incision is made along the length of the wide cross pod away from the seed. The pod can then be easily opened to expose the seed. Alternatively, two pair of forceps can be used to separate the pod shell. Carefully remove the seed from the pod and place in a sterile petri dish under the dissection microscope. Very fine forceps are needed to isolate the embryo from the seed. With forceps in one hand, gently hold the side of the seed away from the embryo, with hilum facing up. Use another pair of forceps in the other hand to remove the seed coat from the side of the seed containing the embryo. Peel off the membrane surrounding the embryo and push the embryo up from tis bottom side. Embryos should be past the globular developmental stage and preferably past the early heart developmental stage (middle to late heart stage, cotyledon stage and early maturation stage embryos are desired). Isolated embryos are transferred to embryo rescue medium such as Soy ER1-1. Embryos can be treated to induce chromosome doubling at this time. (See below for chromosome doubling details.) Isolated embryos remain on embryo rescue medium for 21 to 30 days at 24° C. Embryos may remain in the dark for the entire incubation on ER1-1, may begin the incubation in the dark and complete it in the light, or may spend the entire incubation in the light. There is not a callus induction stage in this protocol. Shoots are developed directly from the embryos.

Chromosome doubling treatments: Either colchicine of trifluralin can be used to induce chromosome doubling. Ideally, late heart stage wide cross embryos (or larger) are chemically treated to induce chromosome doubling at any time from immediately following isolation up to 1 week post isolation. The doubling agent can be mixed in either solid or liquid medium and applied for several hours or up to a few days. Trifluralin is used at a concentration of 10-40 uM in either solid or liquid media. Additionally, colchicine is used at a concentration of 0.4-1 mg/ml in either solid or liquid media. Following the chemical treatment the embryos are transferred to fresh embryo rescue medium.

Shoot regeneration: Developing embryos are transferred from rescue medium to germination medium such as Soy ER GSMv2 for approximately 3 to 5 weeks in the light at 24° C.

Alternatively, developing embryos may be transferred from rescue medium to elongation medium such as Soy E1 0 No TCV for approximately 3 to 5 weeks in the light at 24° C. Developing shoots may be transferred from media plates to Phytocons containing either germination or elongation medium for further shoot development. Established shoots are moved to soil. Initial plant care is critical for survival of these shoots.

Ploidy Analysis: Ploidy analysis is conducted using a flow cytometer. Leaf tissue for ploidy analysis is collected from small shoots either in culture or after establishment in soil. Tissue is collected on dry ice and stored at −80° C. until analysis, or collected on wet ice and analyzed the same day. A sample size of 0.5 cm$^2$ is sufficient. Samples are prepared according to the instructions in the Sysmex kit. Each sample set contains an untreated F1 plant (not treated to induce chromosome doubling) as a control. The following are method notes: Wide crosses—Our wide cross success rate is significantly higher than that reported in the literature. No emasculation of female flowers is performed, which saves time and reduces risk of damage to the stigma.

Harvest—Pod harvest at 14 to 16 days after pollination (~5 days earlier than literature, reducing timeline)

Embryo rescue—Our embryo rescue protocol involves direct shoot regeneration from embryos, rather than regeneration through embryogenesis, thus making plant recovery quicker (shoot recovery in approximately 2-3 months, compared to reported up to 1 year timeline). Our protocol does not include culture in the dark following transfer to germination medium. Our protocol does not require a transfer to rooting medium.

Chromosome doubling—Have successfully used trifluralin treatment to produce doubled F1 plant: trifluralin treatment can be done immediately following embryo rescue.

Example 5: ASR Resistance Trait Introgression

Three independent, B2F1 non-naturally occurring mutant soybean lines generated from introgression of RG21 Gene into *Glycine max* through embryo rescue were tested for efficacy against 6 Asian Soy rust races. The expression of the introgressed trait gene was monitored by qRT-PCR analysis with RG21 specific probe (TQ2681)(SEQ ID NO: 9) before ASR infection. Total 12 leaf discs (n=12) were collected from individual introgressed lines by employing soybean as a negative control (n=10) and a donor accession PI499939 (n=8) as a positive control. The expression of the introgressed RG21 gene in three independent lines was determined by comparing to endogenous soybean Cyp2 (GmCyp2) control. The efficacy against 9 NA ASRs was rated 14 days post-infection.

The trait gene RG21 was successfully introgressed in three independent B2F1 lines. Two introgressed lines, UR234613938 and UR234817537 expressed RG21 relatively lower than UR235760102. The expression of RG21 gene in the donor accession PI499949 was higher than all three introgressed lines (FIG. 7).

All three introgressed lines demonstrated near-complete immunity to six tested ASR races as the donor accession PI499939, while wild type *G. max* showed heavy sporulation upon infection with all six ASRs (TAN2/3 to TAN4). Importantly, all three introgressed lines did not allow any sporulation without resistant phenotype such as Red-Brown (RB) symptom (RB0 nsp=RB0 no-sporulation; Table 1).

TABLE 1

| G. max | RTP1 TAN3 | RTP3 TAN4 | RTP6 TAN4 | FLQ11 TAN2/3 | FLQ12 TAN2/3 | LABR13 TAN2/3 |
|---|---|---|---|---|---|---|
| UR234613938 | RB0 nsp | RB0 nsp | RB0 nsp | RB0 nsp | RB0 nsp | RB0 nsp |
| UR234817537 | RB0 nsp | RB0 nsp | RB0 nsp | RB0 nsp | RB0 nsp | RB0 nsp |
| UR235760102 | RB0 nsp | RB0 nsp | RB0 nsp | RB0 nsp | RB0 nsp | RB0 nsp |
| PI499939 | RB0 nsp | RB0 nsp | RB0 nsp | RB0 nsp | RB0 nsp | RB0 nsp |

Example 6: Construction of Vectors Comprising RG22 Genes

Vector 25190 (SEQ ID NO: 4), illustrated in FIG. 8, was constructed containing an RG22 gene (SEQ ID NO: 3). Features are generally similar to the vectors previously described.

Example 7: Validation of RG22 Genes Against ASR

Numerous soybeans events were created using the vector of Example 6. Leaves from primary events were placed in a petri dish on moist paper towel then inoculated with a spore suspension of 6 different rust races. After 14 days, these leaves were evaluated for resistance.

Many events tested provide strong resistance compared to wild type soybean. In order to quantify the level of disease resistance, leaves were sampled for qRT-PCR analysis to quantify the relative expression of soybean rust β-tubulin gene. FIG. 9 illustrates the quantification for an ASR strain at 14 days after infection.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

The invention claimed is:

1. A transgenic *Glycine max* plant comprising, stably integrated into its genome, a heterologous polynucleotide encoding a polypeptide having at least 99% sequence identity to the amino acid sequence of SEQ ID NO: 1 operably linked to a promoter active in the plant, wherein expression of said polypeptide confers the transgenic plant with increased resistance to Asian Soybean Rust when compared to a *Glycine max* plant not expressing the polypeptide.

2. A method of controlling Asian Soybean Rust in a field comprising the step of planting, in the field, a transgenic *Glycine max* plant, or seed thereof, having stably incorporated into its genome a heterologous polynucleotide encoding a polypeptide having at least 99% sequence identity to the amino acid sequence of SEQ ID NO: 1 operably linked to a promoter active in the plant, wherein expression of said polypeptide confers the transgenic plant with increased resistance to Asian Soybean Rust when compared to a *Glycine max* plant not expressing the polypeptide.

3. The transgenic *Glycine max* plant of claim 1, wherein the polypeptide comprises the amino acid sequence of SEQ ID NO: 1.

4. The transgenic *Glycine max* plant of claim 1, wherein said heterologous polynucleotide comprises the nucleotide sequence of SEQ ID NO: 2.

5. The method of claim 2, wherein said heterologous polynucleotide comprises the nucleotide sequence of SEQ ID NO: 2.

6. The method of claim 2, wherein the heterologous polynucleotide encodes a polypeptide comprising the amino acid sequence of SEQ ID NO: 1.

7. The *Glycine max* plant of claim 1, wherein the promoter active in the plant comprises the nucleotide sequence of SEQ ID NO: 7.

8. The method of claim 2, wherein the promoter active in the plant comprises the nucleotide sequence of SEQ ID NO: 7.

9. A transgenic *Glycine max* plant comprising, stably integrated into its genome, a polynucleotide encoding a polypeptide having at least 99% sequence identity to the amino acid sequence of SEQ ID NO: 1 operably linked to a heterologous regulatory element, wherein expression of said polypeptide confers the transgenic plant with increased resistance to Asian Soybean Rust when compared to a *Glycine max* plant not expressing the polypeptide.

10. The transgenic *Glycine max* plant of claim 9, wherein the heterologous regulatory element is a promoter active in the plant.

11. The transgenic *Glycine max* plant of claim 10, wherein the plant active promoter comprises the nucleotide sequence of SEQ ID NO: 7.

12. The transgenic *Glycine max* plant of claim 9, wherein the polynucleotide comprises the nucleotide sequence of SEQ ID NO: 2.

13. The transgenic *Glycine max* plant of claim 9, wherein the polynucleotide encodes a polypeptide comprising the amino acid sequence of SEQ ID NO: 1.

14. A method of controlling Asian Soybean Rust in a field comprising the step of planting, in the field, a transgenic *Glycine max* plant, or seed thereof, having stably incorporated into its genome a polynucleotide encoding a polypeptide having at least 99% sequence identity to the amino acid sequence of SEQ ID NO: 1 operably linked to a heterologous regulatory element, wherein expression of said polypeptide confers the transgenic plant with increased resistance to Asian Soybean Rust when compared to a *Glycine max* plant not expressing the polypeptide.

15. The method of claim 14, wherein the heterologous regulatory element is a promoter active in the plant.

16. The method of claim 15, wherein the plant active promoter comprises the nucleotide sequence of SEQ ID NO: 7.

17. The method of claim 14, wherein the polynucleotide comprises the nucleotide sequence of SEQ ID NO: 2.

18. The method of claim 14, wherein the polynucleotide encodes a polypeptide comprising the amino acid sequence of SEQ ID NO: 1.

\* \* \* \* \*

SEQUENCE LISTING

```
<160> NUMBER OF SEQ ID NOS: 14

<210> SEQ ID NO 1
<211> LENGTH: 1256
<212> TYPE: PRT
<213> ORGANISM: Glycine tomentella
```

<400> SEQUENCE: 1

Met Ala Leu Ala Ile Val Gly Glu Ala Leu Ile Ser Ala Ser Val Glu
1               5                   10                  15

Ile Leu Leu Asp Arg Ile Thr Ser Val Glu Phe Arg Asn Phe Phe Ala
            20                  25                  30

Asn Arg Lys Leu Asn Val Ser Leu Leu Asp Glu Leu Lys Ile Lys Leu
            35                  40                  45

Leu Ala Leu Ser Ala Val Leu Asn Asp Ala Glu Glu Lys Gln Ile Thr
        50                  55                  60

Asn Ser Glu Val Lys Ala Trp Leu Asp Glu Leu Lys Asp Ala Val Leu
65                  70                  75                  80

Asp Ala Glu Asp Leu Leu Asp Gln Ile Asn Thr Asp Ser Leu Arg Cys
                85                  90                  95

Lys Val Glu Glu Gln Tyr Lys Thr Phe Lys Ser Gln Val Trp Ser Ser
                100                 105                 110

Leu Ser Ser Pro Phe Asn Gln Phe Tyr Arg Ser Met Asn Ser Lys Leu
                115                 120                 125

Glu Ala Ile Ser Gly Arg Leu Glu Asn Phe Ile Lys Gln Lys Asp Ile
        130                 135                 140

Leu Gly Leu Lys Ser Val Ala Gly Arg Val Ser Tyr Arg Lys Asp Thr
145                 150                 155                 160

Asp Arg Ser Val Glu Tyr Val Val Ala Arg Asp Asp Lys Lys Lys
                165                 170                 175

Leu Leu Thr Met Leu Leu Ser Asp Glu Asp Glu Asn Asn Asn His Ile
                180                 185                 190

Lys Val Leu Thr Ile Trp Gly Met Gly Leu Gly Lys Thr Thr Leu
                195                 200                 205

Ala Gln Ser Leu Leu Asn Asp Asp Ala Val Gln Asn His Phe Asp Leu
        210                 215                 220

Lys Ala Trp Ala Trp Val Ser Asp Pro Phe Asp Val Phe Lys Ala Thr
225                 230                 235                 240

Lys Ala Ile Val Glu Ser Ala Thr Ser Lys Thr Cys Asp Thr Thr Asn
                245                 250                 255

Phe Asp Ala Leu Arg Val Glu Leu Lys Asn Thr Phe Lys Asp Lys Phe
                260                 265                 270

Phe Leu Leu Val Leu Asp Asp Leu Trp Asn Met Gln Tyr His Asp Trp
                275                 280                 285

Asp Gln Leu Ile Ala Pro Phe Ile Ser Cys Gly Lys Lys Gly Ser Ile
        290                 295                 300

Ile Ile Val Thr Thr Arg Gln His Arg Ile Ala Glu Ile Thr Ser Thr
305                 310                 315                 320

Phe Pro Ile His Glu Leu Lys Ile Leu Thr Asp Asp Asn Cys Trp Cys
                325                 330                 335

Ile Leu Ala Lys His Ala Phe Gly Asn Gln Gly Tyr Asp Lys Tyr Pro
                340                 345                 350

Ile Leu Ala Glu Ile Gly Arg Gln Ile Ala Thr Lys Cys Lys Gly Leu
        355                 360                 365

Pro Leu Ala Ala Lys Thr Leu Gly Gly Leu Leu Arg Ser Asn Val Asp
        370                 375                 380

Ala Glu Tyr Trp Asn Glu Ile Leu Asn Ser Asn Met Trp Ala Asn Asn
385                 390                 395                 400

```
Glu Val Leu Pro Ala Leu Cys Ile Ser Tyr Leu Gln Leu Pro Pro His
                405                 410                 415

Leu Lys Arg Cys Phe Ala Tyr Cys Ser Ile Phe Pro Arg Gln His Leu
            420                 425                 430

Leu Asp Arg Lys Glu Leu Ile Leu Leu Trp Met Ala Glu Gly Phe Leu
        435                 440                 445

Pro Gln Ile His Arg Glu Lys Ala Met Glu Ser Ala Gly Glu Asp Tyr
    450                 455                 460

Phe Asn Glu Leu Leu Ser Arg Ser Leu Ile Glu Lys Asp Lys Asn Glu
465                 470                 475                 480

Gly Lys Glu Gln Phe Arg Met His Asp Leu Ile Tyr Asp Leu Ala Arg
                485                 490                 495

Leu Val Ser Gly Lys Arg Ser Cys Tyr Phe Glu Gly Gly Glu Val Pro
            500                 505                 510

Ile Asn Val Arg His Leu Thr Tyr His Pro Arg Tyr Leu Asp Val Ser
        515                 520                 525

Thr Arg Phe Glu Gly Leu Tyr Gly Leu Lys Leu Leu Arg Ser Phe Leu
    530                 535                 540

Arg Leu Ser Gln Tyr Ser Ser Val Ser Lys Arg Val Thr His Glu
545                 550                 555                 560

Trp Leu Pro Thr Leu Thr Tyr Leu Arg Thr Leu Ser Leu Ile Gln Tyr
                565                 570                 575

Arg Asn Ile Thr Glu Leu Pro Asp Ser Ile Ser Asn Leu Val Leu Leu
            580                 585                 590

Arg Tyr Leu Asp Leu Ser Tyr Thr Ser Ile Lys Ser Leu Pro Asp Ala
        595                 600                 605

Thr Phe Arg Leu Tyr Asn Leu Gln Thr Leu Lys Leu Ser His Cys Glu
    610                 615                 620

His Leu Thr Glu Leu Thr Glu Gln Ile Gly Asp Leu Leu Leu Arg
625                 630                 635                 640

Tyr Leu Asp Leu Ser Tyr Thr Ser Ile Asn Gln Leu Pro Glu Gln Ile
                645                 650                 655

Gly Asn Leu Val Asn Leu Arg His Leu Asp Ile Arg Gly Thr Asn Leu
            660                 665                 670

Thr Glu Met Pro Ala Gln Ile Ser Lys Leu Gln Asp Leu Arg Val Leu
        675                 680                 685

Thr Ser Phe Val Val Gly Arg Glu Asp Gly Val Asn Ile Arg Glu Leu
    690                 695                 700

Arg Lys Phe Pro Tyr Leu Gln Gly Thr Leu Ser Ile Leu Arg Leu Gln
705                 710                 715                 720

Asn Val Val Asp Pro Lys Asp Ala Phe Gln Ala Asp Leu Lys Lys Lys
                725                 730                 735

Glu His Ile Glu Glu Leu Arg Leu Glu Trp Gly Ser Glu Pro Gln Asp
            740                 745                 750

Ser Gln Ile Glu Lys Asp Val Leu Gln Asn Leu Gln Pro Ser Thr Asn
        755                 760                 765

Leu Lys Lys Leu Ser Val Arg Tyr Tyr Ser Gly Thr Ser Phe Pro Lys
    770                 775                 780

Trp Leu Gly Asp Ser Ser Tyr Ser Tyr Val Ile Phe Leu Cys Ile Thr
785                 790                 795                 800

Asn Cys Lys Tyr Cys Phe Ser Leu Pro Pro Phe Gly Gln Leu Pro Ser
                805                 810                 815
```

```
Leu Lys Glu Leu Val Ile Lys Arg Met Lys Met Val Lys Thr Val Gly
            820                 825                 830

Glu Glu Phe Tyr Cys Asn Asn Gly Val Ser Leu Ser Phe Gln Pro Phe
            835                 840                 845

Pro Leu Leu Glu Ser Ile Glu Phe Glu Glu Met Ser Glu Trp Glu Glu
            850                 855                 860

Trp Leu Pro Phe Glu Gly Gly Ser Lys Phe Pro Phe Pro Cys Leu
865                 870                 875                 880

Lys His Leu Ser Leu Ser Lys Cys Pro Lys Leu Arg Gly Asn Leu Pro
                885                 890                 895

Asn His Leu Pro Ser Leu Thr Glu Val Ser Ile Ser Cys Asn Arg
            900                 905                 910

Leu Glu Ala Lys Ser His Asp Leu His Trp Asn Thr Ser Ile Glu Glu
            915                 920                 925

Ile Thr Ile Arg Glu Ala Gly Glu Gln Leu Leu Ser Leu Leu Asp Asn
            930                 935                 940

Phe Ser Tyr Arg Asn Leu Arg Ile Glu Lys Cys Asp Ser Leu Ser Ser
945                 950                 955                 960

Leu Pro Arg Met Ile Leu Ala Ala Asn Cys Leu Gln Arg Leu Thr Leu
                965                 970                 975

Lys Asp Ile Pro Asn Leu Ile Ser Phe Pro Ala Asp Gly Leu Pro Thr
                980                 985                 990

Ser Leu Gln Phe Leu Asp Ile Asp  Asn Cys Glu Asn Leu  Glu Phe Leu
                995                 1000                1005

Ser Pro  Glu Ser Cys His Lys  Tyr Thr Ser Leu Glu  Tyr Leu Ser
    1010                1015                1020

Ile Val  Asn Ser Cys His Ser  Leu Ala Ser Leu Pro  Leu Asp Gly
    1025                1030                1035

Phe Ser  Ser Leu Gln Ser Leu  Gln Ile Leu Glu Cys  Pro Asn Met
    1040                1045                1050

Glu Ala  Ile Thr Thr Gln Gly  Gly Thr Asn Ala Leu  Lys Leu Thr
    1055                1060                1065

Tyr Leu  Tyr Val Tyr Lys Cys  Lys Lys Leu Arg Ser  Leu Pro Glu
    1070                1075                1080

Gln Ile  Asp Leu Pro Ala Leu  Gln Trp Leu Gly Leu  Ser Glu Leu
    1085                1090                1095

Pro Glu  Leu Thr Ser Leu Pro  Pro Arg Cys Leu Pro  Ser Ser Leu
    1100                1105                1110

Glu Thr  Leu Lys Val Glu Val  Gly Met Leu Ser Ser  Met Ser Lys
    1115                1120                1125

His Glu  Leu Gly Phe Leu Phe  Gln Arg Leu Thr Ser  Leu Ser Arg
    1130                1135                1140

Leu Tyr  Ile Ser Gly Phe Gly  Glu Glu Asp Val Val  Asn Thr Leu
    1145                1150                1155

Leu Lys  Glu Cys Leu Leu Pro  Thr Ser Leu Gln His  Leu Ser Leu
    1160                1165                1170

Trp Tyr  Phe Asp Asp Leu Lys  Leu Leu Glu Gly Lys  Gly Leu Gln
    1175                1180                1185

His Leu  Thr Ser Leu Arg Asp  Leu Gly Ile Arg Asn  Cys Lys Ser
    1190                1195                1200

Leu Glu  Ser Leu Pro Glu Asp  Gln Leu Pro Ser Ser  Leu Glu Leu
    1205                1210                1215
```

```
Leu Glu  Ile His Gly Cys Pro  Leu Leu Glu Ala Arg  Tyr Gln Ser
    1220             1225                 1230

Arg Lys  Gly Lys His Trp Ser  Lys Ile Ala His Ile  Pro Ala Ile
    1235             1240                 1245

Lys Ile  Asn Asp Glu Val Ile  Ile
    1250             1255

<210> SEQ ID NO 2
<211> LENGTH: 3771
<212> TYPE: DNA
<213> ORGANISM: Glycine tomentella

<400> SEQUENCE: 2
atggctttgg ctattgtggg agaggcactt atctctgctt ctgtggagat cttgctggat     60
aggataactt ctgtggagtt tcgaaatttc tttgccaata gaaagctgaa tgtttctctc    120
ttggatgagc tgaagataaa gctgttggca ctcagtgctg tgctcaatga tgctgaggag    180
aaacagatca ctaattcaga agtgaaggca tggcttgatg agttgaaaga tgctgtttta    240
gacgcagagg atttgttgga ccaaatcaac acagattctc tgaggtgcaa ggtgaggaa     300 caatacaaaa cctttaaaag ccaggtgtgg tcatcacttt cttctccctt taatcaattc    360
tataggagca tgaattccaa gcttgaagca atatctggaa ggctagaaaa ttttatcaaa    420
caaaaagata ttcttggttt gaaaagtgtt gctggcagag tctcttaccg aaaagataca    480
gatcgatcgg tggaatatgt tgttgcaaga gacgatgaca aaagaagct gttgaccatg     540 cttctctctg atgaagatga gaataataat cacataaaag tgctgacaat atggggcatg    600
ggaggtcttg gaaaacaac ccttgctcag agccttttaa atgacgatgc agtgcagaac     660
cattttgatc tcaaagcttg gcatgggta tctgatcctt tgatgtgtt taaggcaacg      720 aaggcaattg ttgaatctgc cacttcaaaa acttgtgata ctactaattt tgatgctctt    780
cgagttgaat tgaagaacac cttaaagat aaatttttt tgcttgtgct cgatgacctt      840
tggaatatgc agtatcatga ttgggatcaa ctaatagccc cttttattag ctgtgggaag    900
aagggaagta taatcattgt gacaacccga caacacagaa ttgcagaaat cactagtaca    960
tttcccattc acgagctgaa gattcttaca gatgacaact gttggtgtat acttgctaaa   1020
catgcatttg gaaatcaagg atatgacaaa tatcccatcc tagcagaaat ggtagacaa    1080 attgcaacaa aatgcaaggg tctaccatta gcagctaaaa cattgggagg tcttttgcga   1140
tcaaatgttg atgcagagta ttggaatgaa attctgaaca gcaacatgtg gcaaataat    1200 gaagttttac cagctttatg cataagttat cttcaacttc caccacatct gaaaagatgt   1260
tttgcctatt gctcaatttt tcctagacaa catttgttgg ataggaagga attgattctg   1320
ttatggatgg ctgaaggctt tcttccacaa atccacagag agaaagcaat ggaatcagca   1380
ggtgaagact acttcaatga attgttatct agatctttaa ttgaaaaaga caaaaatgag   1440
ggaaaggaac agtttcgaat gcatgacctt atctacgatt tagccagact agtctctggt   1500
aagagatctt gttactttga aggaggagaa gtcccaataa atgttcgcca tctgacatat   1560
catcccagat atcttgatgt ctctacaaga tttgagggct tgtatgggct aaagcttttg   1620
cgcagctttt tacgactatc tcaatattct agtagtgtat ccaaaagggt gacacatgag   1680
tggctgccaa cactaacata tctgcgaaca ttgtccttga ttcagtatag aaatatcact   1740
gagctgcctg attcaataag caatttggta ctgttgcggt atcttgacct ttcctatact   1800
tccatcaaaa gtttgcctga tgcaaccttt aggctttaca atttgcagac tttgaaatta   1860
```

```
tcacattgtg aacatcttac agagttgact gaacagatag gagatttgtt acttttacgg   1920
tatcttgacc tttcctatac ttccatcaat cagctgcctg aacagatagg aaatttggtc   1980
aatctacgcc accttgatat tagaggcaca aatttgacgg agatgccagc acaaataagc   2040
aagctacaag atctccgtgt gttgacttct tttgttgtag gcagagaaga tggagtaaat   2100
atcagagaat taagaaagtt tccttacttg caaggtacgc tttccatttt gaggttacaa   2160
aatgttgttg atcccaagga tgcttttcaa gctgacttaa agaagaaaga gcatattgag   2220
gagcttaggt tggagtgggg cagtgagcca caagattcac aaattgagaa agatgtactt   2280
cagaacctgc aaccatcgac aaatttaaag aaactcagcg taagatacta cagtggcaca   2340
agctttccta aatggttggg tgactcttca tattcttatg ttatattcct ttgcatcact   2400
aattgcaaat attgcttttc acttccacca tttggacaac taccttctct caaggagctt   2460
gtgataaaaa ggatgaaaat ggtgaagaca gttggtgaag aattctactg caacaatggg   2520
gtttcccttt catttcaacc atttccattg ttggagagta tcgagttcga agagatgtca   2580
gagtgggaag agtggctacc atttgaaggt gaaggcagca agtttccttt tccttgcctt   2640
aaacatttga gtttatcaaa atgccccaag ttgagaggaa acttgcccaa ccatctacct   2700

tccttgacag aggttagtat atcagagtgc aaccggctag aggcaaaatc acatgatcta   2760
cattggaaca catcaattga agaaataacg attagagaag caggagaaca attgttgtcc   2820
ttgcttgaca actttttctta caggaatcta cggattgaaa aatgtgacag cttgtcatct   2880
ttgccaagaa tgatactagc tgccaattgt ctccaaaggt tgactcttaa ggatatcccc   2940
aatttgattt ccttcccagc cgatggcttg ccaacgtcat tgcaatttct tgacattgac   3000
aactgtgaga acttagaatt tctgtctccc gaatcatgcc acaaatacac atcacttgaa   3060
tatctgtcaa ttgtcaatag ctgccattcc ctggcatcct taccattaga tggtttctct   3120
tccctacaaa gtcttcaaat cttggaatgt cccaacatgg aagcaattac tactcaaggt   3180
ggaacgaatg ctctcaaatt aacttatctt tatgtttata aatgtaagaa acttaggtca   3240
cttccagaac agattgatct ccctgccctt caatggttag ggctttctga gcttccagag   3300
ctgacatcat tgcccccaag gtgtttgcct tccagtttag aaacactcaa agttgaagtt   3360
ggaatgctat catcaatgtc taaacacgag ttaggtttcc tattccaacg cctcacttct   3420
ctgtctcgtc tttacattag tggttttggg gaggaagatg ttgttaacac cctgttgaag   3480
gagtgcttac tgcccacttc gctgcaacat ctgtccctat ggtattttga tgatttaaag   3540
ttgttggaag gaaaagggct ccaacatctc acttccctca gagatcttgg catcaggaat   3600
tgtaaaagcc tcgagtcctt gcccgaagat cagcttccat cctctcttga attactggag   3660
atacatggtt gtcctttact agaagcaagg tatcaaagtc ggaaagggaa acactggtct   3720
aagattgctc acattcctgc gatcaagata aatgatgaag tgataatatg a            3771
```

<210> SEQ ID NO 3
<211> LENGTH: 17590
<212> TYPE: DNA
<213> ORGANISM: artificial
<220> FEATURE:
<223> OTHER INFORMATION: Vector 25307

<400> SEQUENCE: 3

```
attcctgtgg ttggcatgca catacaaatg gacgaacgga taaacctttt cacgcccttt     60
taaatatccg attattctaa taaacgctct tttctcttag gtttacccgc caatatatcc    120
```

```
tgtcaaacac tgatagttta aactggcact agcctaacgg tgttgactaa ctaggccgct      180
tccctaatta gctaacccgg gggcgcgccg ggaccctaaa tatttaaata tattttgata      240
tgcacacata tttcaaaaaa ttgttatttt gttgtgttct aggtagaatt ttcttcacat      300
taataatgtc ttgcatgctc cttttttact ttcttttaaa caaagttgat ttattttatt      360
ttattttatt ttgtaattgt gttatcagta caaattattt aatggttttg ttcatgatta      420 tttttttgtca aaaataaca cctatatcca cgtaataata cattcttttta taatacatttt     480 taaaattaaa ttaattaaat atgttaaagt tatcaatata tacatttctt aggtcctatg      540
ttatttggga atccgttaga cttgcaaggc tttgattttt attctacagg gatctctaat      600
ttaggctatg ttttgttttg atttaattat atttttttta gttctcactc atattttaat      660
ttatgggaaa ttttatagta ttttaaattt taattcttta tactttattt ttatacaatt      720
taattattaa aattaagttc ctcatttcaa atttcatcca ataacgtatg aataaaagat      780
tgtgaggtga ctttgattta tacaaattgg tgtaagaaag ataaatatat attaagagaa      840
aaaaaataac ttcttgtaag gacacattat cacataatgt attgtaagga cttcaatgta      900
agaaattgtg aatcaaaact atcgaccact cctattacta ctttattgtc attgtataaa      960
tatttattta aggcaactta atcacatcct caaatttgaa aaaagtattt tttttcaatt     1020
tttattctcc atgtccagta tcattgccct taaaaagcta aaaaaaaaac atatatagat     1080
gtgcaatcta aaatacatga tttctttatt aataataatc atttaatatc ttaccaaatt     1140
attatcaatt tgccacagca tgtcaatttt ttttttgttca tagtaatcta ttactttatt     1200
tttatacact ttatacgaat aaataaataa attaaaaatt tgcaacaata aacaattata     1260
tgtaaattat taaaactttt ttgaaggaat aaattatcat aactttaata atataaaatta     1320 ttattttttaa ttaaatataa aaaatgatag ccaaaaaatt atacatgatg aagtttaaac    1380
ttaatatccg tgcaaggcac accggatttt acgctagtaa attttaacta aaattacaca     1440
tgttaaatta aagggatcag aagtgtaatt attttatttt atttttttta aaaatcatct     1500
taaaataata caagtaataa gtaattattc taaaaatttg attcctccga gagtgaaact     1560
ttcaactacc taatgcaaac tttgtcaaag tgaaatttga ctacacccag caaactttgt     1620
aagcaatgtt gcaatgttct aagagttaat ctcatagcta ttcttgtaag gactccgaat     1680
caattaaaga caaagagtag ggaatctaac ttttttcaaca acaaattaat tacatgcacg     1740
atagtgtagg ccgtttaaga aagtttaaga gagtaactga tatgtggcat cttagatata     1800
tactaagcaa ataatattgc ataatagaac atgaaatcat gaatgctgat ttaaaagcat     1860
taaacaaacg aattgaggaa tgagggaggt gtcaagtttt aggaattcag aaaaatgtat     1920
aattaactct tattagtttt ttttttgctg aaattcactg tattattaca cttcgtaggc     1980
agaagatatc aggaaggacc gaagaagtat acattattga aaaagtccaa acgcagagtg     2040
gttggatggt cacattaaag gaaataaact attgtactat tctttgtttt ctcaaagaca     2100
ggcaaataaa acatttattt atgatcatac cctaattcct cactagctaa gatataacct     2160
tcagcgtttg actaaaggtt cagagatctg atactatttg caaaactaga gaagagatgg     2220
ctttggctat tgtgggagag gcacttatct ctgcttctgt ggagatcttg ctggatagga     2280
taacttctgt ggagtttcga aatttctttg ccaatagaaa gctgaatgtt tctctcttgg     2340
atgagctgaa gataaagctg ttggcactca gtgctgtgct caatgatgct gaggagaaac     2400
agatcactaa ttcagaagtg aaggcatggc ttgatgagtt gaaagatgct gttttagacg     2460
cagaggattt gttggaccaa atcaacacag attctctgag gtgcaaggtg gaggaacaat     2520
```

```
acaaaacctt taaaagccag gtgtggtcat cactttcttc tccctttaat caattctata   2580
ggagcatgaa ttccaagctt gaagcaatat ctggaaggct agaaaatttt atcaaacaaa   2640
aagatattct tggtttgaaa agtgttgctg gcagagtctc ttaccgaaaa gatacagatc   2700
gatcggtgga atatgttgtt gcaagagacg atgacaaaaa gaagctgttg accatgcttc   2760
tctctgatga agatgagaat aataatcaca taaaagtgct gacaatatgg ggcatgggag   2820
gtcttggaaa acaacccctt gctcagagcc ttttaaatga cgatgcagtg cagaaccatt   2880
ttgatctcaa agcttgggca tgggtatctg atccttttga tgtgtttaag gcaacgaagg   2940
caattgttga atctgccact tcaaaaactt gtgatactac taattttgat gctcttcgag   3000
ttgaattgaa gaacaccttt aaagataaat ttttttgct tgtgctcgat gacctttgga   3060
atatgcagta tcatgattgg gatcaactaa tagccccttt tattagctgt gggaagaagg   3120
gaagtataat cattgtgaca acccgacaac acagaattgc agaaatcact agtacatttc   3180
ccattcacga gctgaagatt cttacagatg acaactgttg gtgtatactt gctaaacatg   3240
catttggaaa tcaaggatat gacaaatatc ccatcctagc agaaattggt agacaaattg   3300
caacaaaatg caagggtcta ccattagcag ctaaaacatt gggaggtctt ttgcgatcaa   3360
atgttgatgc agagtattgg aatgaaattc tgaacagcaa catgtgggca aataatgaag   3420
ttttaccagc tttatgcata agttatcttc aacttccacc acatctgaaa agatgttttg   3480
cctattgctc aattttttcct agacaacatt tgttggatag gaaggaattg attctgttat   3540
ggatggctga aggctttctt ccacaaatcc acagagagaa agcaatggaa tcagcaggtg   3600
aagactactt caatgaattg ttatctagat ctttaattga aaaagacaaa aatgagggaa   3660
aggaacagtt tcgaatgcat gaccttatct acgatttagc cagactagtc tctggtaaga   3720
gatcttgtta ctttgaagga ggagaagtcc caataaatgt tcgccatctg acatatcatc   3780
ccagatatct tgatgtctct acaagatttg agggcttgta tgggctaaag ctttttgcgca   3840 gcttttttacg actatctcaa tattctagta gtgtatccaa aagggtgaca catgagtggc   3900
tgccaacact aacatatctg cgaacattgt ccttgattca gtatagaaat atcactgagc   3960
tgcctgattc aataagcaat ttggtactgt tgcggtatct tgaccttttcc tatacttcca   4020 tcaaaagttt gcctgatgca acctttttaggc tttacaattt gcagactttg aaattatcac   4080
attgtgaaca tcttacagag ttgactgaac agataggaga tttgttactt ttacggtatc   4140
ttgacctttc ctatacttcc atcaatcagc tgcctgaaca gataggaaat ttggtcaatc   4200
tacgccacct tgatattaga ggcacaaatt tgacggagat gccagcacaa ataagcaagc   4260
tacaagatct ccgtgtgttg acttcttttg ttgtaggcag agaagatgga gtaaatatca   4320
gagaattaag aaagtttcct tacttgcaag gtacgctttc cattttgagg ttacaaaatg   4380
ttgttgatcc caaggatgct tttcaagctg acttaaagaa gaaagagcat attgaggagc   4440
ttaggttgga gtggggcagt gagccacaag attcacaaat tgagaaagat gtacttcaga   4500
acctgcaacc atcgacaaat ttaaagaaac tcagcgtaag atactacagt ggcacaagct   4560
ttcctaaatg gttgggtgac tcttcatatt cttatgttat attcctttgc atcactaatt   4620
gcaaatattg cttttcactt ccaccatttg gacaactacc ttctctcaag gagcttgtga   4680
taaaaaggat gaaaatggtg aagacagttg gtgaagaatt ctactgcaac aatggggttt   4740
ccctttcatt tcaaccattt ccattgttgg agagtatcga gttcgaagag atgtcagagt   4800
gggaagagtg gctaccattt gaaggtgaag gcagcaagtt tccttttcct tgccttaaac   4860
```

```
atttgagttt atcaaaatgc cccaagttga gaggaaactt gcccaaccat ctaccttcct    4920
tgacagaggt tagtatatca gagtgcaacc ggctagaggc aaaatcacat gatctacatt    4980
ggaacacatc aattgaagaa ataacgatta gagaagcagg agaacaattg ttgtccttgc    5040
ttgacaactt ttcttacagg aatctacgga ttgaaaaatg tgcagcttg tcatctttgc     5100 caagaatgat actagctgcc aattgtctcc aaaggttgac tcttaaggat atccccaatt    5160
tgatttcctt cccagccgat ggcttgccaa cgtcattgca atttcttgac attgacaact    5220
gtgagaactt agaatttctg tctcccgaat catgccacaa atacacatca cttgaatatc    5280
tgtcaattgt caatagctgc cattccctgg catccttacc attagatggt ttctcttccc    5340
tacaaagtct tcaaatcttg gaatgtccca acatggaagc aattactact caaggtggaa    5400
cgaatgctct caaattaact tatctttatg tttataaatg taagaaactt aggtcacttc    5460
cagaacagat tgatctccct gcccttcaat ggttagggct ttctgagctt ccagagctga    5520
catcattgcc cccaaggtgt ttgccttcca gtttagaaac actcaaagtt gaagttggaa    5580
tgctatcatc aatgtctaaa cacgagttag gtttcctatt ccaacgcctc acttctctgt    5640 ctcgtctttta cattagtggt tttggggagg aagatgttgt taacaccctg ttgaaggagt    5700
gcttactgcc cacttcgctg caacatctgt ccctatggta ttttgatgat ttaaagttgt    5760
tggaaggaaa agggctccaa catctcactt ccctcagaga tcttggcatc aggaattgta    5820
aaagcctcga gtccttgccc gaagatcagc ttccatcctc tcttgaatta ctggagatac    5880
atggttgtcc tttactagaa gcaaggtatc aaagtcggaa agggaaacac tggtctaaga    5940
ttgctcacat tcctgcgatc aagataaatg atgaagtgat aatatgacct gtggcatgag    6000
taggaagtag gaaccatcca gaagctgaaa ttcactgtat tattacactt cgtaggcaga    6060
agatatcagg aaggaccgaa gaagtataca ttattgaaaa agtccaaacg cagagtggtt    6120
ggatggtcac attaaaggaa ataaactatt gtactattct ttgttttctc aaagacaggc    6180
aaataaaaca tttatttatg atcatacct aattcctcac tagctaagat ataaccttca     6240
gcgtttgact aaaggttcag agatctgata ctatttgcaa aactagagaa gagaagttga    6300
ataattattt taaaatgttc tgattatagt gcaagcttgc aagtgaatga agtgatagat    6360
tgtatgtgta tatgggcatt gttatcaaac ttgatctgga ctggccggtc ggatcgagat    6420
tcgatgacat aatcagatcg gttccacttt cgaatcagtt aaacagttga tccggttaaa    6480
cccggtcagg tcaccagatc ccagttggac ttgtccgact cggttgattt tttttttaaaa    6540 actaatttttt ataattttt aaaatttgaa ttttggaatg tggatgagtt ttcttactc      6600 aaataatgtt agttatatac ttatatgtaa tagatatata tatatatata agtttgaatt    6660
cttaatatat atcgagtcaa atcaggctaa ttactggctc accagttgga ccactaactc    6720
gctgacctat tacctcgatc gggtcaatga ctagactgag tttcacaact atgattacgg    6780
ggaaacaatg tcaataagtt agattataaa atctgatttt tgactataaa aaaaaccaac    6840
taataaaagt gtaacaatt aagaatatat ttatgataca agaaaaaaaa tatgcaaaat      6900
gatagtttgt agctcctttc aaaatcaata tcatctagca acccacgatt ttcggcatta    6960
gaagctttac ttaaacgtgg tatcaaattc ttttaacatt ggccatctaa ttcttttatt    7020
tttatttgat tttttttggt actataatca acttgattac acaaggagta ttctcaaata    7080
ctctttgcac ttcctctccc acactgtgac tcgctcctta atttggtaca acatggcttt    7140
tacaaagaca aacatataa aacaatgttg aataacccaa ctaatttagc acaaaatatt     7200
gtattgaaca aattgttcat agtttcatat tagcatgttg ttaacggaac ctcaataaga    7260
```

```
atgatcttaa atttttttggt tgattttgtg agacggaccc ctaattagct aagagacact    7320
tgtgtgattg agagaaacac taatcttgtg aggactgaag tttggtgatt atttcttgtg    7380
atctgtcgac aaaaatatca aatggggttt cttttacaaa ttatttaccT aaatgaatct    7440
gttttgaaaa tatttactcc attgggtcta ttttttttatt acaaagcgtc tccctgaagg    7500
gcgcgttccc cgtgaaagtg acacgtggca ggacttggga cgtgccctgc gtacaggcgc    7560
gatagttagt gttgttacag caggcgcatc gggtcgtgtt ggggaccaag gtacgacagg    7620
tcgcgctggg tgacccagac acgacccaat tgggtcgcac tttatttaat attttttata    7680
ttttgtatat tgttttttatt taatatattt ttatattatt ttatttaatt tttttatatt    7740
ttatataata gttctatat taaataaatt cttagcatta tgtatgattt taaagtcata    7800
aataattttt tatattgttt ttatttacta tatttttttat atttttattta atatttatat    7860 attaaataaa tccttcatat tagaaaaaat aaagaaaata ttaaataaaa tataaaatat    7920
aaaaaagtaa aaaatattaa ataaaataat ataaaaaata ttataaaaac aatataaaaa    7980
atataaaaat atttaataaa ataataaaaa aaatattatt ttaaataaaa ttatttatga    8040
ctttaaactc taaagttgaa ttttaaaaaa atataatttt tttacgattt tagtaaaaaa    8100
aaaatacaag ccgcacaata caagtcgcct tctcaaaccc ttcctcacga cattctcgga    8160
ccttatgaca ccgtcaccaa aacaatgatc cacgcgatat taggcgcgtg caaatcactc    8220
taatccgaaa ctagtagaca tgggaagcac gagctatacg cgagcgtttc aattgccgcc    8280
acgaaagcag agaaggccag aaacggaacc acggtaaaat ggtaagggta ttttcgtaaa    8340
cagaagaaaa gagttgtagc tataaataaa ccctctaacc cacggcgcac tatttctctt    8400
cactccttcg ttcactcttc ttctcttgcg gctagggttt tagcgcagct tcttctaggt    8460
tcgttctctt ccgccgctct atggatttta aaccttcgaa tcatgtttat tccattgaat    8520
tatgttgctt gcagtttata ttttctgaat ctgtagttgt tgtcttcaat ttatcctatg    8580
ctttatagat caatcttttg tgtgtgtagt acgtaattt tgttcttttt gcttttcgtt    8640
caagttgttg ggaataatcg gggtatcatg ttttgatatt gtttgttttc ttttttgact    8700
gcttaataat ttttaagttg gttttggttt tggggttttta tgtgcttgtt atattcaaat    8760
ctttgtgatc cagatcttac aaaagttttg ggtttaagga tgttttttggc tgatgatgaa    8820 tagatctata aactgttcct tttaatcgat tcaagcttag gattttacta ggcttttgcg    8880
aataaatacg tgacagtaag ctaattatgt cctttttttg tctcaatcat atctgtctgg    8940
gtgtgccata atttgtgata tgtctatctg gtagaatctt gtgttttatg ctttacgatt    9000
tggtatacct gttttttgaac ttgttgtatg atgggtattt agatcaccct atcttttta    9060 tgcttctgga agttttatgt aaatgtcgaa tatcttaatg ttgttgaact tataatgttg    9120
tgttgatgta tgtatgatgg ttttgacaac ttttttcact ggttctgaaa gttttatgta    9180
aattgcaaat atgttaatgt tgttgaactt attttttttc cttcgatgtt gttttgatgt    9240
atgtatgatg gttttcaccg tagtttctat ggctaatatc ttaatgttgt tgagcttatt    9300
tttttcctta tatgttgtgt tgatgtattg tatgatggtt ttgacaactt ttttagtttc    9360
tttgcagatt taaggaagga tcaaaaatgg ctgctgctgc tgcagctcca tctccatcat    9420
tctctaagac cttgtcctct tcatcctcta agtcctctac tcttttgcca aggtctactt    9480
tcccattccc acatcatcca cataagacta ctccaccacc acttcatctt accccaaccc    9540
atattcactc tcagagaaga aggttcacca tctctaacgt tatctccacc acccaaaagg    9600
```

```
tttcagagac tcaaaaggct gagactttcg tttctaggtt cgctccagat gagccaagaa    9660
agggatctga tgttcttgtt gaggctcttg aaagggaagg tgttactgat gttttcgctt    9720
atccaggtgg cgcttctatg gaaattcatc aagctcttac caggtcctcc atcattagaa    9780
acgttttgcc aagacatgag cagggtggtg ttttcgctgc tgaaggatat gctagagcta    9840
ctggattccc tggtgtgtgt attgctactt ctggaccagg tgctaccaac cttgtttctg    9900
gacttgctga tgctctcctt gattctgttc caattgtggc tattaccgga caagttgcta    9960
gaaggatgat tggaaccgat gctttccaag agactccaat tgtggaagtg accagatcta   10020
tcaccaagca caactacctt gtgatggatg ttgaggatat ccaagggtt gtgagagagg    10080 cattcttctt ggctagatct ggtagaccag gaccagttct tattgatgtg ccaaaggata   10140
ttcagcagca gcttgttatc ccagattggg atcaacctat gagacttcca ggttacatgt   10200
ctaggcttcc aaagcttcct aacgagatgc ttcttgagca gattgtgagg cttatttccg   10260
agtctaagaa gccagttctc tacgttggtg gtggatgctc tcaatcttct gaggaactta   10320
gacgtttcgt tgagcttacc ggaattccag ttgcttctac tcttatggga cttggagctt   10380
tcccaactgg tgatgaactt tctctttcca tgcttggaat gcatggaacc gtttatgcta   10440
actacgctgt ggattcctcc gatcttcttc ttgctttcgg tgttaggttc gatgatagag   10500
ttaccggaaa gcttgaggct ttcgcttcta gagctaagat tgtgcacatc gatatcgatt   10560
ccgctgagat tggaaagaac aagcagccac atgtgtccat ttgcgctgat attaagcttg   10620
cacttcaggg actcaactcc attcttgaat ccaagagggg aaagctcaag cttgatttct   10680
ctgcttggag gcaagagctt actgttcaga aggttaagta cccctcaac ttcaagactt    10740 tcggagatgc tattccacca cagtacgcta ttcaagtgct tgatgagctt accaacggct   10800
ctgctattat ttctactggt gttggacagc atcagatgtg ggctgctcaa tattacaagt   10860
acagaaagcc aaggcagtgg cttacttctg gtggacttgg tgctatggga ttcggacttc   10920
cagctgctat tggagctgct gttggtagac cagatgaagt tgttgtggat atcgatggtg   10980
atggctcctt cattatgaac gttcaagagc ttgccaccat caaggttgaa aaccttccag   11040
tgaagatcat gctccttaac aaccagcatc ttggaatggt tgtgcaactt gaggacagat   11100
tctacaaggc taacagggct catacctatc ttggaaaccc atctaacgag ctgagatttt   11160
tcccaaacat gcttaagttc gctgaggctt gcggagttcc tgctgctaga gttactcata   11220
gagatgatct cagggctgct attcagaaga tgcttgatac tccaggacca taccttctcg   11280
atgttattgt gccacatcaa gagcatgtgc tcccaatgat tccatctggt ggtgctttca   11340
aggatgttat tactgagggt gatggaaggt cctcctacta agtgctagca ttttgtacat   11400
tgagtaggga agagagagag atatatataa atactcacaa agcagtgagt atatggcttg   11460
cttttgtttc taaacattcc tttataagga cttgagataa tttgtattgt ttaaaagagc   11520
cattggttct gttgtatcaa agtaatttaa ttttcagtac cgacttggct ctactctat    11580 gtggtggtgt acattgcatc tttgcatttg attccatatc tattgggatg ggaccataca   11640
ttttttgttt attatttaag tcaaacatat cagataatat gtggtgacca gaaaagtgtc   11700
tagcaatcaa atgggtctgt gattgcatgt ttgagttcag gacatttatt aatgagtgac   11760
agaattttaa aaagctcgcc aataggagtt gccacatctg atcgagtctt ctgtaaacac   11820
taactgtaac ttgagtttga taatcagatt cccccgttg gtaggtaata tgtaaatttc   11880
actatagatt cttactgagg atgatggtct tgacttcgaa gtggtgagtg taattctcta   11940
atctaaactt tatatatata taaaaaaaga atgttaaaaa cttgagtgac atacagcaaa   12000
```

```
tagcaatgaa agcatgacca ttggccttgg ggggccaaat ggccatgtac cacttttcca   12060
cctacttgag agccattggt cctgaatgag gtccttttgt ttcattttt ttacaataaa    12120 gaaagttcat attcttggca atagcaaggc aaatcatttg tggaagtcac atgaaattca   12180
ccatactaat tagctaacgg acccgattta atcggtacc actagtaata ttcggaccgc    12240
ctgcaggccc gggggcgcgc cctaattagc taacggccag gatcgccgcg tgagccttta   12300
gcaactagct agattaatta acgcaatctg ttattaagtt gtctaagcgt caatttgttt   12360
acaccacaat atatcctgcc accagccagc caacagctcc ccgaccggca gctcggcaca   12420
aaatcaccac tcgatacagg cagcccatca gaattaattc tcatgtttga cagcttatca   12480
tcgactgcac ggtgcaccaa tgcttctggc gtcaggcagc catcggaagc tgtggtatgg   12540
ctgtgcaggt cgtaaatcac tgcataattc gtgtcgctca aggcgcactc ccgttctgga   12600
taatgttttt tgcgccgaca tcataacggt tctggcaaat attctgaaat gagctgttga   12660
caattaatca tccggctcgt ataatgtgtg gaattgtgag cggataacaa tttcacacag   12720
gaaacagacc atgagggaag cgttgatcgc cgaagtatcg actcaactat cagaggtagt   12780
tggcgtcatc gagcgccatc tcgaaccgac gttgctggcc gtacatttgt acggctccgc   12840
agtggatggc ggcctgaagc cacacagtga tattgatttg ctggttacgg tgaccgtaag   12900
gcttgatgaa acaacgcggc gagctttgat caacgacctt ttggaaactt cggcttcccc   12960
tggagagagc gagattctcc gcgctgtaga agtcaccatt gttgtgcacg acgacatcat   13020
tccgtggcgt tatccagcta agcgcgaact gcaatttgga gaatggcagc gcaatgacat   13080
tcttgcaggt atcttcgagc cagccacgat cgacattgat ctggctatct tgctgacaaa   13140
agcaagagaa catagcgttg ccttggtagg tccagcggcg gaggaactct ttgatccggt   13200
tcctgaacag gatctatttg aggcgctaaa tgaaacctta acgctatgga actcgccgcc   13260
cgactgggct ggcgatgagc gaaatgtagt gcttacgttg tcccgcattt ggtacagcgc   13320
agtaaccggc aaaatcgcgc cgaaggatgt cgctgccgac tgggcaatgg agcgcctgcc   13380
ggcccagtat cagcccgtca tacttgaagc taggcaggct tatcttggac aagaagatcg   13440
cttggcctcg cgcgcagatc agttggaaga atttgttcac tacgtgaaag gcgagatcac   13500
caaagtagtc ggcaaataaa gctctagtgg atctccgtac ccagggatct ggctcgcggc   13560
ggacgcacga cgccggggcg agaccatagg cgatctccta aatcaatagt agctgtaacc   13620
tcgaagcgtt tcacttgtaa caacgattga gaattttgt cataaaattg aaatacttgg    13680
ttcgcatttt tgtcatccgc ggtcagccgc aattctgacg aactgcccat ttagctggag   13740
atgattgtac atccttcacg tgaaaatttc tcaagcgctg tgaacaaggg ttcagatttt   13800
agattgaaag gtgagccgtt gaaacacgtt cttcttgtcg atgacgacgt cgctatgcgg   13860
catcttatta ttgaataccT tacgatccac gccttcaaag tgaccgcggt agccgacagc   13920
acccagttca caagagtact ctcttccgcg acggtcgatg tcgtggttgt tgatctagat   13980
ttaggtcgtg aagatgggct cgagatcgtt cgtaatctgg cggcaaagtc tgatattcca   14040
atcataatta tcagtggcga ccgccttgag gagacggata agttgttgc actcgagcta    14100 ggagcaagtg attttatcgc taagccgttc agtatcagag agtttctagc acgcattcgg   14160
gttgccttgc gcgtgcgccc caacgttgtc cgctccaaag accgacggtc ttttgtttt    14220 actgactgga cacttaatct caggcaacgt cgcttgatgt ccgaagctgg cggtgaggtg   14280
aaacttacgg caggtgagtt caatcttctc ctcgcgtttt tagagaaacc ccgcgacgtt   14340
```

```
ctatcgcgcg agcaacttct cattgccagt cgagtacgcg acgaggaggt ttatgacagg    14400
agtatagatg ttctcatttt gaggctgcgc cgcaaacttg aggcagatcc gtcaagccct    14460
caactgataa aaacagcaag aggtgccggt tatttctttg acgcggacgt gcaggtttcg    14520
cacgggggga cgatggcagc ctgagccaat tcccagatcc ccgaggaatc ggcgtgagcg    14580
gtcgcaaacc atccggcccg gtacaaatcg gcgcggcgct gggtgatgac ctggtggaga    14640
agttgaaggc cgcgcaggcc gcccagcggc aacgcatcga ggcagaagca cgccccggtg    14700
aatcgtggca agcggccgct gatcgaatcc gcaaagaatc ccggcaaccg ccggcagccg    14760
gtgcgccgtc gattaggaag ccgcccaagg gcgacgagca accagatttt ttcgttccga    14820
tgctctatga cgtgggcacc cgcgatagtc gcagcatcat ggacgtggcc gttttccgtc    14880
tgtcgaagcg tgaccgacga gctggcgagg tgatccgcta cgagcttcca gacgggcacg    14940
tagaggtttc cgcagggccg gccggcatgg ccagtgtgtg ggattacgac ctggtactga    15000
tggcggtttc ccatctaacc gaatccatga accgataccg ggaagggaag ggagacaagc    15060
ccggccgcgt gttccgtcca cacgttgcgg acgtactcaa gttctgccgg cgagccgatg    15120
gcggaaagca gaaagacgac ctggtagaaa cctgcattcg gttaaacacc acgcacgttg    15180
ccatgcagcg tacgaagaag gccaagaacg gccgcctggt gacggtatcc gagggtgaag    15240
ccttgattag ccgctacaag atcgtaaaga gcgaaaccgg gcggccggag tacatcgaga    15300
tcgagctggc tgattggatg taccgcgaga tcacagaagg caagaacccg gacgtgctga    15360
cggttcaccc cgattacttt ttgatcgatc ccggcatcgg ccgttttctc taccgcctgg    15420
cacgccgcgc cgcaggcaag gcagaagcca gatggttgtt caagacgatc tacgaacgca    15480
gtggcagcgc cggagagttc aagaagttct gtttcaccgt gcgcaagctg atcgggtcaa    15540
atgacctgcc ggagtacgat ttgaaggagg aggcggggca ggctggcccg atcctagtca    15600
tgcgctaccg caacctgatc gagggcgaag catccgccgg ttcctaatgt acggagcaga    15660
tgctagggca aattgcccta gcaggggaaa aaggtcgaaa aggtctcttt cctgtgggata    15720 gcacgtacat tgggaaccca aagccgtaca ttgggaaccg gaacccgtac attgggaacc    15780
caaagccgta cattgggaac cggtcacaca tgtaagtgac tgatataaaa gagaaaaaag    15840 gcgattttc cgcctaaaac tctttaaaac ttattaaaac tcttaaaacc cgcctggcct    15900
gtgcataact gtctggccag cgcacagccg aagagctgca aaaagcgcct acccttcggt    15960
cgctgcgctc cctacgcccc gccgcttcgc gtcggcctat cgcggccgct ggccgctcaa    16020
aaatggctgg cctacggcca ggcaatctac cagggcgcgg acaagccgcg ccgtcgccac    16080
tcgaccgccg gcgctgaggt ctgcctcgtg aagaaggtgt tgctgactca taccaggcct    16140
gaatcgcccc atcatccagc cagaaagtga gggagccacg gttgatgaga gctttgttgt    16200
aggtggacca gttggtgatt tgaacttttt gctttgccac ggaacggtct gcgttgtcgg    16260
gaagatgcgt gatctgatcc ttcaactcag caaaagttcg atttattcaa caaagccgcc    16320
gtcccgtcaa gtcagcgtaa tgctctgcca gtgttacaac caattaacca attctgatta    16380
gaaaaactca tcgagcatca aatgaaactg caatttattc atatcaggat tatcaatacc    16440 atattttga aaaagccgtt tctgtaatga aggagaaaac tcaccgaggc agttccatag    16500
gatggcaaga tcctggtatc ggtctgcgat tccgactcgt ccaacatcaa tacaacctat    16560
taatttcccc tcgtcaaaaa taaggttatc aagtgagaaa tcaccatgag tgacgactga    16620
atccggtgag aatggcaaaa gctctgcatt aatgaatcgg ccaacgcgcg gggagaggcg    16680
gtttgcgtat tgggcgctct tccgcttcct cgctcactga ctcgctgcgc tcggtcgttc    16740
```

```
ggctgcggcg agcggtatca gctcactcaa aggcggtaat acggttatcc acagaatcag    16800
gggataacgc aggaaagaac atgtgagcaa aaggccagca aaaggccagg aaccgtaaaa    16860
aggccgcgtt gctggcgttt ttccataggc tccgcccccc tgacgagcat cacaaaaatc    16920
gacgctcaag tcagaggtgg cgaaacccga caggactata agataccagg cgtttcccc    16980 ctggaagctc cctcgtgcgc tctcctgttc cgaccctgcc gcttaccgga tacctgtccg    17040
cctttctccc ttcgggaagc gtggcgcttt ctcatagctc acgctgtagg tatctcagtt    17100
cggtgtaggt cgttcgctcc aagctgggct gtgtgcacga accccccgtt cagcccgacc    17160
gctgcgcctt atccggtaac tatcgtcttg agtccaaccc ggtaagacac gacttatcgc    17220
cactggcagc agccactggt aacaggatta gcagagcgag gtatgtaggc ggtgctacag    17280
agttcttgaa gtggtggcct aactacggct acactagaag aacagtattt ggtatctgcg    17340
ctctgctgaa gccagttacc ttcggaaaaa gagttggtag ctcttgatcc ggcaaacaaa    17400
ccaccgctgg tagcggtggt ttttttgttt gcaagcagca gattacgcgc agaaaaaaag    17460
gatctcaaga agatcctttg atcttttcta cggggtctga cgctcagtgg aacgaaaact    17520
cacgttaagg gattttggtc atgagattat caaaaaggat cttcacctag atccttttga    17580
tccggaatta                                                           17590

<210> SEQ ID NO 4
<211> LENGTH: 16666
<212> TYPE: DNA
<213> ORGANISM: artificial
<220> FEATURE:
<223> OTHER INFORMATION: Vector 25374

<400> SEQUENCE: 4
attcctgtgg ttggcatgca catacaaatg gacgaacgga taaaccttt cacgcccttt      60 taaatatccg attattctaa taaacgctct tttctcttag gtttacccgc caatatatcc     120
tgtcaaacac tgatagttta aactggcact agcctaacgg tgttgactaa ctaggccgct     180
tccctaatta gctaacccgg gggcgcgccg ggacccttaa ctagctagat tccaaaattt     240
tcagttagtc cttactaatt attaaattat agtattaatc caatgtgatt gcggttacat     300
catgtacgga aaataattc taatccttgt tttaaatttg atcttgacta tttatttatt     360
ctttatttca ttttgtaaat catttatgt atctcctggc aagcaatttt atccaccttg     420
caccaacacc ttcgggttcc ataatcaaac caccttaact tcacaccatg ctgtaactca     480
caccgcccag catctccaat gtgaaagaag ctaaaattta ataaacaatc atacgaagca     540
gtgacaaaat accagatggt attaatgctt tgataaaatt aattggaaag tataaaatgg     600
tagaaaataa taaattataa ttattttaaa taagataaaa ataattaaa aactaaaatg     660 ttaaaatttt aaaaaaatta ttttaaataa tatttaaaaa cattaaaaat cattttaaaa     720
aattatttta tagaacaatt aaataaatat ttcagctaat aaaaaacaaa agcttaccta     780
gccttagaag acaacttgtc caacaattag atgataccca ttgcccttac gttttctta     840 acatcaatta ttgttttgt caacaagcta tcttttagtt ttattttatt ggtaaaaaat     900
atgtcgcctt caagttgcat catttaacac atctcgtcat tagaaaaata aaactcttcc     960
ctaaacgatt agtagaaaaa atcattcgat aataaataag aaagaaaaat tagaaaaaaa    1020
taacttcatt ttaaaaaaat cattaaggct atatttttta aatgactaat tttatataga    1080
ctgtaactaa aagtatacaa tttattatgc tatgtatctt aaagaattac ttataaaaat    1140
```

-continued

```
ctacggaaga atatcttaca aagtgaaaaa caaatgagaa agaatttagt gggatgatta    1200
tgattttatt tgaaaattga aaaataatt attaaagact ttagtggagt aagaaagctt    1260
tcctattagt cttttcttat ccataaaaaa aaaaaaaaat ctagcgtgac agcttttcca    1320
tagattttaa taatgtaaaa tactggtagc agccgaccgt tcaggtaatg acactgtgg    1380 tcctaacttg caacgggtgc gggcccaatt taataacgcc gtggtaacgg ataaagccaa    1440
gcgtgaagcg gtgaaggtac atctctgact ccgtcaagat tacgaaaccg tcaactacga    1500
aggactcccc gaaatatcat ctgtgtcata acaccaagt cacaccatac atgggcacgc     1560
gtcacaattt gattggagaa cggttccacc gcatatgcta taaattgccc ccacacccct    1620
cgaccctaat cgcacttcaa ttgcaatcaa attagttcat tctctttgcg cagttccta     1680 cctctccttt caaggttcgt agatttcttc tgttttttt tcttcttctt tattgtttgt     1740
tctacatcag catgatgttg atttgattgt gttttctatc gtttcatcga ttataaattt    1800
tcataatcag aagattcagc ttttattaat gcaagaacgt ccttaattga tgattttata   1860
accgtaaatt aggtctaatt agagtttttt tcataaagat tttcagatcc gtttacaaca    1920
agccttaatt gttgattctg tagtcgtaga ttaaggtttt tttcatgaac tacttcagat   1980
ccgttaaaca acagccttat tgttgatac ttcagtcgtt tttcaagaaa ttgttcagat     2040
ccgttgataa aagccttatt cgttgattct gtatggtatt tcaagagata ttgctcaggt    2100
cctttagcaa ctaccttatt tgttgattct gtggccatag attaggattt tttttcacga    2160
aattgcttct tgaaattacg tgatggattt tgattctgat ttatcttgtg attgttgact    2220
ctacagggat cctaaaccat ggctttggct attgtgggag aggcacttat ctctgcttct    2280
gtggagatct tgctggatag gataacttct gtggagtttc gaaatttctt tgccaataga    2340
aagctgaatg tttctctctt ggatgagctg aagataaagc tgttggcact cagtgctgtg    2400
ctcaatgatg ctgaggagaa acagatcact aattcagaag tgaaggcatg gcttgatgag    2460
ttgaaagatg ctgttttaga cgcagaggat ttgttggacc aaatcaacac agattctctg    2520
aggtgcaagg tggaggaaca atacaaaacc tttaaaagcc aggtgtggtc atcactttct    2580 tctccctta atcaattcta taggagcatg aattccaagc ttgaagcaat atctggaagg    2640
ctagaaaatt ttatcaaaca aaaagatatt cttggtttga aaagtgttgc tggcagagtc    2700
tcttaccgaa aagatacaga tcgatcggtg gaatatgttg ttgcaagaga cgatgacaaa    2760
aagaagctgt tgaccatgct tctctctgat gaagatgaga ataataatca cataaaagtg    2820
ctgacaatat ggggcatggg aggtcttgga aaaacaaccc ttgctcagag ccttttaaat    2880
gacgatgcag tgcagaacca ttttgatctc aaagcttggg catgggtatc tgatcctttt    2940
gatgtgttta aggcaacgaa ggcaattgtt gaatctgcca cttcaaaaac ttgtgatact    3000
actaattttg atgctcttcg agttgaattg aagaacacct taaagataa attttttttg     3060 cttgtgctcg atgacctttg gaatatgcag tatcatgatt gggatcaact aatagcccct    3120
tttattagct gtgggaagaa gggaagtata atcattgtga caacccgaca acacagaatt    3180
gcagaaatca ctagtacatt tcccattcac gagctgaaga ttcttacaga tgacaactgt    3240
tggtgtatac ttgctaaaca tgcatttgga aatcaaggat atgacaaata tcccatccta    3300
gcagaaattg gtagacaaat tgcaacaaaa tgcaagggtc taccattagc agctaaaaca    3360
ttgggaggtc ttttgcgatc aaatgttgat gcagagtatt ggaatgaaat tctgaacagc    3420
aacatgtggg caaataatga agttttacca gctttatgca taagttatct tcaacttcca    3480
ccacatctga aaagatgttt tgcctattgc tcaattttc ctagacaaca tttgttggat    3540
```

```
aggaaggaat tgattctgtt atggatggct gaaggctttc ttccacaaat ccacagagag    3600
aaagcaatgg aatcagcagg tgaagactac ttcaatgaat tgttatctag atctttaatt    3660
gaaaaagaca aaaatgaggg aaaggaacag tttcgaatgc atgaccttat ctacgattta    3720
gccagactag tctctggtaa gagatcttgt tactttgaag gaggagaagt cccaataaat    3780
gttcgccatc tgacatatca tcccagatat cttgatgtct ctacaagatt tgagggcttg    3840
tatgggctaa agcttttgcg cagcttttta cgactatctc aatattctag tagtgtatcc    3900
aaaagggtga cacatgagtg gctgccaaca ctaacatatc tgcgaacatt gtccttgatt    3960
cagtatagaa atatcactga gctgcctgat tcaataagca atttggtact gttgcggtat    4020
cttgaccttt cctatacttc catcaaaagt ttgcctgatg caacctttag gctttacaat    4080
ttgcagactt tgaaattatc acattgtgaa catcttacag agttgactga acagatagga    4140
gatttgttac ttttacggta tcttgacctt tcctatactt ccatcaatca gctgcctgaa    4200
cagataggaa atttggtcaa tctacgccac cttgatatta gaggcacaaa tttgacggag    4260
atgccagcac aaataagcaa gctacaagat ctccgtgtgt tgacttcttt tgttgtaggc    4320
agagaagatg gagtaaatat cagagaatta agaaagtttc cttacttgca aggtacgctt    4380
tccattttga ggttacaaaa tgttgttgat cccaaggatg cttttcaagc tgacttaaag    4440
aagaaagagc atattgagga gcttaggttg gagtggggca gtgagccaca agattcacaa    4500
attgagaaag atgtacttca gaacctgcaa ccatcgacaa atttaaagaa actcagcgta    4560
agatactaca gtggcacaag ctttcctaaa tggttgggtg actcttcata ttcttatgtt    4620
atattccttt gcatcactaa ttgcaaatat tgcttttcac ttccaccatt tggacaacta    4680
ccttctctca aggagcttgt gataaaaagg atgaaaatgg tgaagacagt tggtgaagaa    4740
ttctactgca acaatggggt ttcccttca tttcaaccat ttccattgtt ggagagtatc    4800
gagttcgaag agatgtcaga gtgggaagag tggctaccat ttgaaggtga aggcagcaag    4860 tttcctttc cttgccttaa acatttgagt ttatcaaaat gccccaagtt gagaggaaac    4920
ttgcccaacc atctaccttc cttgacagag gttagtatat cagagtgcaa ccggctagag    4980
gcaaaatcac atgatctaca ttggaacaca tcaattgaag aaataacgat tagagaagca    5040
ggagaacaat tgttgtcctt gcttgacaac ttttcttaca ggaatctacg gattgaaaaa    5100
tgtgacagct tgtcatcttt gccaagaatg atactagctg ccaattgtct ccaaaggttg    5160
actcttaagg atatccccaa tttgatttcc ttcccagccg atggcttgcc aacgtcattg    5220
caatttcttg acattgacaa ctgtgagaac ttagaatttc tgtctcccga atcatgccac    5280
aaatacacat cacttgaata tctgtcaatt gtcaatagct gccattccct ggcatcctta    5340
ccattagatg gtttctcttc cctacaaagt cttcaaatct tggaatgtcc caacatggaa    5400
gcaattacta ctcaaggtgg aacgaatgct ctcaaattaa cttatcttta tgtttataaa    5460
tgtaagaaac ttaggtcact tccagaacag attgatctcc ctgcccttca atggttaggg    5520
ctttctgagc ttccagagct gacatcattg cccccaaggt gtttgccttc cagtttagaa    5580
acactcaaag ttgaagttgg aatgctatca tcaatgtcta acacgagtt aggtttccta    5640 ttccaacgcc tcacttctct gtctcgtctt tacattagtg gttttgggga ggaagatgtt    5700
gttaacaccc tgttgaagga gtgcttactg cccacttcgc tgcaacatct gtccctatgg    5760 tatttgatg atttaaagtt gttggaagga aagggctcc aacatctcac ttccctcaga    5820
gatcttggca tcaggaattg taaaagcctc gagtccttgc ccgaagatca gcttccatcc    5880
```

-continued

| | |
|---|---|
| tctcttgaat tactggagat acatggttgt cctttactag aagcaaggta tcaaagtcgg | 5940 |
| aaagggaaac actggtctaa gattgctcac attcctgcga tcaagataaa tgatgaagtg | 6000 |
| ataatatgag agctcagctt tttgtgatct gatgataagt ggttggttcg tgtctcatgc | 6060 |
| acttgggagg tgatctattt cacctggtgt agtttgtgtt tccgtcagtt ggaaaaactt | 6120 |
| atccctatcg atttcgtttt cattttctgc ttttctttta tgtaccttcg tttgggcttg | 6180 |
| taacgggcct ttgtatttca actctcaata taatccaag tgcatgttaa acaatttgtc | 6240 |
| atctgtttcg gctttgatat actactggtg aagatgggcc gtactactgc atcacaacga | 6300 |
| aaaataataa taagatgaaa aacttgaagt ggaaaaaaaa aacttgaatg ttcactacta | 6360 |
| cctagctagc ggacccctaa ttagctaaga gacacttgtg tgattgagag aaacactaat | 6420 |
| cttgtgagga ctgaagtttg gtgattattt cttgtgatct gtcgacaaaa atatcaaatg | 6480 |
| gggtttcttt tacaaattat ttacctaaat gaatctgttt tgaaaatatt tactccattg | 6540 |
| ggtctatttt tttattacaa agcgtctccc tgaagggcgc gttccccgtg aaagtgacac | 6600 |
| gtggcaggac ttgggacgtg ccctgcgtac aggcgcgata gttagtgttg ttacagcagg | 6660 |
| cgcatcgggt cgtgttgggg accaaggtac gacaggtcgc gctgggtgac ccagacacga | 6720 |
| cccaattggg tcgcacttta tttaatattt tttatatttt gtatattgtt tttatttaat | 6780 |
| atatttttat attattttat ttaattttt tatatttat ataatagttt ctatattaaa | 6840 |
| taaattctta gcattatgta tgattttaaa gtcataaata attttttata ttgtttttat | 6900 |
| ttactatatt ttttatattt tatttaatat ttatatatta aataaatcct tcatattaga | 6960 |
| aaaaataaag aaaatattaa ataaaatata aatatataaa aagtaaaaaa tattaaataa | 7020 |
| aataatataa aaaatattat aaaaacaata taaaaaatat aaaaatattt aataaaataa | 7080 |
| taaaaaaaat attattttaa ataaaattat ttatgactt aaactctaaa gttgaatttt | 7140 |
| aaaaaaatat aatttttta cgattttagt aaaaaaaaaa tacaagccgc acaatacaag | 7200 |
| tcgccttctc aaacccttcc tcacgacatt ctcggacctt atgacaccgt caccaaaaca | 7260 |
| atgatccacg cgatattagg cgcgtgcaaa tcactctaat ccgaaactag tagacatggg | 7320 |
| aagcacgagc tatacgcgag cgtttcaatt gccgccacga aagcagagaa ggccagaaac | 7380 |
| ggaaccacgg taaaatggta agggtatttt cgtaaacaga agaaaagagt tgtagctata | 7440 |
| aataaaccct ctaacccacg cgcactatt tctcttcact ccttcgttca ctcttcttct | 7500 |
| cttgcggcta gggtttagc gcagcttctt ctaggttcgt tctcttccgc cgctctatgg | 7560 |
| atttttaaacc ttcgaatcat gtttattcca ttgaattatg ttgcttgcag tttatatttt | 7620 |
| ctgaatctgt agttgttgtc ttcaatttat cctatgcttt atagatcaat cttttgtgtg | 7680 |
| tgtagtacgt aattttttgtt cttttttgctt ttcgttcaag ttgttgggaa taatcggggt | 7740 |
| atcatgtttt gatattgttt gttttctttt ttgactgctt aataattttt aagttggttt | 7800 |
| tggttttggg gttttatgtg cttgttatat tcaaatcttt gtgatccaga tcttacaaaa | 7860 |
| gttttgggtt taaggatgtt tttggctgat gatgaataga tctataaact gttccttta | 7920 |
| atcgattcaa gcttaggatt ttactaggct tttgcgaata aatacgtgac agtaagctaa | 7980 |
| ttatgtcctt tttttgtctc aatcatatct gtctgggtgt gccataattt gtgatatgtc | 8040 |
| tatctggtag aatcttgtgt tttatgcttt acgatttggt atacctgttt ttgaacttgt | 8100 |
| tgtatgatgg gtatttagat caccctatct tttttatgct tctggaagtt ttatgtaaat | 8160 |
| gtcgaatatc ttaatgttgt tgaacttata atgttgtgtt gatgtatgta tgatggtttt | 8220 |
| gacaacttttt ttcactggtt ctgaaagttt tatgtaaatt gcaaatatgt taatgttgtt | 8280 |

```
gaacttattt tttttccttc gatgttgttt tgatgtatgt atgatggttt tcaccgtagt   8340
ttctatggct aatatcttaa tgttgttgag cttattttt tccttatatg ttgtgttgat    8400
gtattgtatg atggttttga caacttttt agtttctttg cagatttaag gaaggatcaa    8460
aaatggctgc tgctgctgca gctccatctc catcattctc taagaccttg tcctcttcat   8520
cctctaagtc ctctactctt ttgccaaggt ctactttccc attcccacat catccacata   8580
agactactcc accaccactt catcttaccc caacccatat tcactctcag agaagaaggt   8640
tcaccatctc taacgttatc tccaccaccc aaaaggtttc agagactcaa aaggctgaga   8700 cttttcgtttc taggttcgct ccagatgagc caagaaaggg atctgatgtt cttgttgagg  8760
ctcttgaaag ggaaggtgtt actgatgttt tcgcttatcc aggtggcgct tctatggaaa   8820
ttcatcaagc tcttaccagg tcctccatca ttagaaacgt tttgccaaga catgagcagg   8880
gtggtgtttt cgctgctgaa ggatatgcta gagctactgg attccctggt gtgtgtattg   8940
ctacttctgg accaggtgct accaaccttg tttctggact tgctgatgct ctccttgatt   9000
ctgttccaat tgtggctatt accggacaag ttgctagaag gatgattgga accgatgctt   9060
tccaagagac tccaattgtg gaagtgacca gatctatcac caagcacaac taccttgtga   9120
tggatgttga ggatattcca agggttgtga gagaggcatt cttcttggct agatctggta   9180
gaccaggacc agttcttatt gatgtgccaa aggatattca gcagcagctt gttatcccag   9240
attgggatca acctatgaga cttccaggtt acatgtctag gcttccaaag cttcctaacg   9300
agatgcttct tgagcagatt gtgaggctta tttccgagtc taagaagcca gttctctacg   9360
ttggtggtgg atgctctcaa tcttctgagg aacttagacg tttcgttgag cttaccggaa   9420
ttccagttgc ttctactctt atgggacttg gagctttccc aactggtgat gaactttctc   9480
tttccatgct tggaatgcat ggaaccgttt atgctaacta cgctgtggat tcctccgatc   9540
ttcttcttgc tttcggtgtt aggttcgatg atagagttac cggaaagctt gaggcttcg    9600 cttctagagc taagattgtg cacatcgata tcgattccgc tgagattgga aagaacaagc   9660
agccacatgt gtccatttgc gctgatatta agcttgcact tcagggactc aactccattc   9720
ttgaatccaa agagggaaag ctcaagcttg atttctctgc ttggaggcaa gagcttactg   9780
ttcagaaggt taagtaccccc ctcaacttca agactttcgg agatgctatt ccaccacagt   9840
acgctattca agtgcttgat gagcttacca acggctctgc tattatttct actggtgttg   9900
gacagcatca gatgtgggct gctcaatatt acaagtacag aaagccaagg cagtggctta   9960
cttctggtgg acttggtgct atgggattcg gacttccagc tgctattgga gctgctgttg   10020
gtagaccaga tgaagttgtt gtggatatcg atggtgatgg ctccttcatt atgaacgttc   10080
aagagcttgc caccatcaag gttgaaaacc ttccagtgaa gatcatgctc cttaacaacc   10140
agcatcttgg aatggttgtg caacttgagg acagattcta caaggctaac agggctcata   10200
cctatcttgg aaacccatct aacgaggctg agattttccc aaacatgctt aagttcgctg   10260
aggcttgcgg agttcctgct gctagagtta ctcatagaga tgatctcagg gctgctattc   10320
agaagatgct tgatactcca ggaccatacc ttctcgatgt tattgtgcca catcaagagc   10380
atgtgctccc aatgattcca tctggtggtg cttttcaagga tgttattact gagggtgatg   10440
gaaggtcctc ctactaagtg ctagcatttt gtacattgag tagggaagag agagagatat   10500
atataaatac tcacaaagca gtgagtatat ggcttgcttt tgtttctaaa cattccttta   10560
taaggacttg agataatttg tattgtttaa aagagccatt ggttctgttg tatcaaagta   10620
```

```
atttaattt   cagtaccgac  ttggctctac  tcatatgtgg  tggtgtacat  tgcatctttg    10680
catttgattc  catatctatt  gggatgggac  catacatttt  ttgtttatta  tttaagtcaa    10740
acatatcaga  taatatgtgg  tgaccagaaa  agtgtctagc  aatcaaatgg  gtctgtgatt    10800
gcatgtttga  gttcaggaca  tttattaatg  agtgacagaa  ttttaaaaag  ctcgccaata    10860
ggagttgcca  catctgatcg  agtcttctgt  aaacactaac  tgtaacttga  gtttgataat    10920
cagattcccc  ccgttggtag  gtaatatgta  aatttcacta  tagattctta  ctgaggatga    10980
tggtcttgac  ttcgaagtgg  tgagtgtaat  tctctaatct  aaactttata  tatatataaa    11040
aaaagaatgt  taaaaacttg  agtgacatac  agcaaatagc  aatgaaagca  tgaccattgg    11100
ccttgggggg  ccaaatggcc  atgtaccact  tttccaccta  cttgagagcc  attggtcctg    11160
aatgaggtcc  ttttgtttca  ttttttttac  aataaagaaa  gttcatattc  ttggcaatag    11220
caaggcaaat  catttgtgga  agtcacatga  aattcaccat  actaattagc  taacggaccc    11280
gatttaaatc  ggtaccacta  gtaatattcg  gaccgcctgc  aggcccgggg  gcgcgcccta    11340
attagctaac  ggccaggatc  gccgcgtgag  cctttagcaa  ctagctagat  taattaacgc    11400
aatctgttat  taagttgtct  aagcgtcaat  ttgtttacac  cacaatatat  cctgccacca    11460
gccagccaac  agctccccga  ccggcagctc  ggcacaaaat  caccactcga  tacaggcagc    11520
ccatcagaat  taattctcat  gtttgacagc  ttatcatcga  ctgcacggtg  caccaatgct    11580
tctggcgtca  ggcagccatc  ggaagctgtg  gtatggctgt  gcaggtcgta  aatcactgca    11640
taattcgtgt  cgctcaaggc  gcactcccgt  tctggataat  gttttttgcg  ccgacatcat    11700
aacggtctg   gcaaatattc  tgaaatgagc  tgttgacaat  taatcatccg  gctcgtataa    11760
tgtgtggaat  tgtgagcgga  taacaatttc  acacaggaaa  cagaccatga  gggaagcgtt    11820
gatcgccgaa  gtatcgactc  aactatcaga  ggtagttggc  gtcatcgagc  gccatctcga    11880
accgacgttg  ctggccgtac  atttgtacgg  ctccgcagtg  gatggcggcc  tgaagccaca    11940
cagtgatatt  gatttgctgg  ttacggtgac  cgtaaggctt  gatgaaacaa  cgcggcgagc    12000
tttgatcaac  gaccttttgg  aaacttcggc  ttcccctgga  gagagcgaga  ttctccgcgc    12060
tgtagaagtc  accattgttg  tgcacgacga  catcattccg  tggcgttatc  cagctaagcg    12120
cgaactgcaa  tttggagaat  ggcagcgcaa  tgacattctt  gcaggtatct  tcgagccagc    12180
cacgatcgac  attgatctgg  ctatcttgct  gacaaaagca  agagaacata  gcgttgcctt    12240
ggtaggtcca  gcggcggagg  aactctttga  tccggttcct  gaacaggatc  tatttgaggc    12300
gctaaatgaa  accttaacgc  tatggaactc  gccgcccgac  tgggctggcg  atgagcgaaa    12360
tgtagtgctt  acgttgtccc  gcatttggta  cagcgcagta  accggcaaaa  tcgcgccgaa    12420
ggatgtcgct  gccgactggg  caatggagcg  cctgccggcc  cagtatcagc  ccgtcatact    12480
tgaagctagg  caggcttatc  ttggacaaga  agatcgcttg  gcctcgcgcg  cagatcagtt    12540
ggaagaattt  gttcactacg  tgaaaggcga  gatcaccaaa  gtagtcggca  aataaagctc    12600
tagtggatct  ccgtacccag  ggatctggct  cgcggcggac  gcacgacgcc  ggggcgagac    12660
cataggcgat  ctcctaaatc  aatagtagct  gtaacctcga  agcgtttcac  ttgtaacaac    12720
gattgagaat  ttttgtcata  aaattgaaat  acttggttcg  cattttgtc   atccgcggtc    12780
agccgcaatt  ctgacgaact  gcccatttag  ctggagatga  ttgtacatcc  ttcacgtgaa    12840
aatttctcaa  gcgctgtgaa  caaggggttca  gatttagat   tgaaggtga   gccgttgaaa    12900
cacgttcttc  ttgtcgatga  cgacgtcgct  atgcggcatc  ttattattga  ataccttacg    12960
atccacgcct  tcaaagtgac  cgcggtagcc  gacagcaccc  agttcacaag  agtactctct    13020
```

```
tccgcgacgg tcgatgtcgt ggttgttgat ctagatttag gtcgtgaaga tgggctcgag    13080
atcgttcgta atctggcggc aaagtctgat attccaatca taattatcag tggcgaccgc    13140
cttgaggaga cggataaagt tgttgcactc gagctaggag caagtgattt tatcgctaag    13200
ccgttcagta tcagagagtt tctagcacgc attcgggttg ccttgcgcgt gcgcccaac    13260 gttgtccgct ccaaagaccg acggtctttt tgttttactg actggacact taatctcagg    13320
caacgtcgct tgatgtccga agctggcggt gaggtgaaac ttacggcagg tgagttcaat    13380
cttctcctcg cgtttttaga gaaaccccgc gacgttctat cgcgcgagca acttctcatt    13440
gccagtcgag tacgcgacga ggaggtttat gacaggagta tagatgttct cattttgagg    13500
ctgcgccgca aacttgaggc agatccgtca agccctcaac tgataaaaac agcaagaggt    13560
gccggttatt tctttgacgc ggacgtgcag gtttcgcacg gggggacgat ggcagcctga    13620
gccaattccc agatccccga ggaatcggcg tgagcggtcg caaaccatcc ggcccggtac    13680
aaatcggcgc ggcgctgggt gatgacctgg tggagaagtt gaaggccgcg caggccgccc    13740
agcggcaacg catcgaggca gaagcacgcc ccggtgaatc gtggcaagcg gccgctgatc    13800
gaatccgcaa agaatcccgg caaccgccgg cagccggtgc gccgtcgatt aggaagccgc    13860
ccaagggcga cgagcaacca gatttttcg ttccgatgct ctatgacgtg gcacccgcg    13920 atagtcgcag catcatggac gtggccgttt ccgtctgtc gaagcgtgac cgacgagctg    13980
gcgaggtgat ccgctacgag cttccagacg ggcacgtaga ggtttccgca gggccggccg    14040
gcatggccag tgtgtgggat tacgacctgg tactgatggc ggtttcccat ctaaccgaat    14100
ccatgaaccg ataccgggaa gggaagggag acaagcccgg ccgcgtgttc cgtccacacg    14160
ttgcggacgt actcaagttc tgccggcgag ccgatggcgg aaagcagaaa gacgacctgg    14220
tagaaacctg cattcggtta aacaccacgc acgttgccat gcagcgtacg aagaaggcca    14280 agaacgccg cctggtgacg gtatccgagg gtgaagcctt gattagccgc tacaagatcg    14340
taaagagcga aaccgggcgg ccggagtaca tcgagatcga gctggctgat tggatgtacc    14400
gcgagatcac agaaggcaag aacccggacg tgctgacggt tcaccccgat tacttttga    14460 tcgatcccgg catcggccgt tttctctacc gcctggcacg ccgcgccgca ggcaaggcag    14520
aagccagatg gttgttcaag acgatctacg aacgcagtgg cagcgccgga gagttcaaga    14580
agttctgttt caccgtgcgc aagctgatcg ggtcaaatga cctgccggag tacgatttga    14640
aggaggaggc ggggcaggct ggcccgatcc tagtcatgcg ctaccgcaac ctgatcgagg    14700
gcgaagcatc cgccggttcc taatgtacgg agcagatgct agggcaaatt gccctagcag    14760
gggaaaaagg tcgaaaaggt ctcttcctg tggatagcac gtacattggg aacccaaagc    14820
cgtacattgg gaaccggaac ccgtacattg ggaacccaaa gccgtacatt gggaaccggt    14880
cacacatgta agtgactgat ataaaagaga aaaaggcga ttttccgcc taaaactctt    14940 taaaacttat taaaactctt aaaacccgcc tggcctgtgc ataactgtct ggccagcgca    15000
cagccgaaga gctgcaaaaa gcgcctaccc ttcggtcgct gcgctcccta cgccccgccg    15060
cttcgcgtcg gcctatcgcg gccgctggcc gctcaaaaat ggctggccta cggcaggca    15120 atctaccagg gcgcggacaa gccgcgccgt cgccactcga ccgccggcgc tgaggtctgc    15180
ctcgtgaaga aggtgttgct gactcatacc aggcctgaat cgccccatca tccagccaga    15240
aagtgaggga gccacggttg atgagagctt tgttgtaggt ggaccagttg gtgatttga    15300 acttttgctt tgccacggaa cggtctgcgt tgtcgggaag atgcgtgatc tgatccttca    15360
```

| | | | | |
|---|---|---|---|---|
| actcagcaaa | agttcgattt | attcaacaaa | gccgccgtcc | cgtcaagtca gcgtaatgct | 15420 |
| ctgccagtgt | tacaaccaat | taaccaattc | tgattagaaa | aactcatcga gcatcaaatg | 15480 |
| aaactgcaat | ttattcatat | caggattatc | aataccatat | ttttgaaaaa gccgtttctg | 15540 |
| taatgaagga | gaaaactcac | cgaggcagtt | ccataggatg | gcaagatcct ggtatcggtc | 15600 |
| tgcgattccg | actcgtccaa | catcaataca | acctattaat | ttccctcgt caaaaataag | 15660 |
| gttatcaagt | gagaaatcac | catgagtgac | gactgaatcc | ggtgagaatg gcaaaagctc | 15720 |
| tgcattaatg | aatcggccaa | cgcgcgggga | gaggcggttt | gcgtattggg cgctcttccg | 15780 |
| cttcctcgct | cactgactcg | ctgcgctcgg | tcgttcggct | gcggcgagcg gtatcagctc | 15840 |
| actcaaaggc | ggtaatacgg | ttatccacag | aatcagggga | taacgcagga agaacatgt | 15900 |
| gagcaaaagg | ccagcaaaag | gccaggaacc | gtaaaaaggc | cgcgttgctg gcgttttcc | 15960 |
| ataggctccg | ccccctgac | gagcatcaca | aaaatcgacg | ctcaagtcag aggtggcgaa | 16020 |
| acccgacagg | actataaaga | taccaggcgt | ttccccctgg | aagctccctc gtgcgctctc | 16080 |
| ctgttccgac | cctgccgctt | accggatacc | tgtccgcctt | tctcccttcg ggaagcgtgg | 16140 |
| cgctttctca | tagctcacgc | tgtaggtatc | tcagttcggt | gtaggtcgtt cgctccaagc | 16200 |
| tgggctgtgt | gcacgaaccc | cccgttcagc | ccgaccgctg | cgccttatcc ggtaactatc | 16260 |
| gtcttgagtc | caacccggta | agacacgact | tatcgccact | ggcagcagcc actggtaaca | 16320 |
| ggattagcag | agcgaggtat | gtaggcggtg | ctacagagtt | cttgaagtgg tggcctaact | 16380 |
| acggctacac | tagaagaaca | gtatttggta | tctgcgctct | gctgaagcca gttaccttcg | 16440 |
| gaaaaagagt | tggtagctct | tgatccggca | aacaaaccac | cgctggtagc ggtggttttt | 16500 |
| ttgtttgcaa | gcagcagatt | acgcgcagaa | aaaaggatc | tcaagaagat cctttgatct | 16560 |
| tttctacggg | gtctgacgct | cagtggaacg | aaaactcacg | ttaagggatt ttggtcatga | 16620 |
| gattatcaaa | aaggatcttc | acctagatcc | ttttgatccg | gaatta | 16666 |

```
<210> SEQ ID NO 5
<211> LENGTH: 16085
<212> TYPE: DNA
<213> ORGANISM: Artificial
<220> FEATURE:
<223> OTHER INFORMATION: VC24965

<400> SEQUENCE: 5
```

| | | | | | |
|---|---|---|---|---|---|
| attcctgtgg | ttggcatgca | catacaaatg | gacgaacgga | taaacctttt cacgcccttt | 60 |
| taaatatccg | attattctaa | taaacgctct | tttctcttag | gtttaccgc caatatatcc | 120 |
| tgtcaaacac | tgatagttta | aactggcact | agcctaacgg | tgttgactaa ctaggccgct | 180 |
| tccctaatta | gctaacccgg | gggcgcgccg | ggacccctagg | ccggttcaac attttttttg | 240 |
| ttttgagtta | ttatctgggc | ttaataacgc | aggcctgaaa | taaattcaag gcccaactgt | 300 |
| tttttttttt | aagaagttgc | tgttaaaaaa | aaaaaaggg | aattaacaac aacaacaaaa | 360 |
| aaagataaag | aaaataataa | caattacttt | aattgtagac | taaaaaaaca tagattttat | 420 |
| catgaaaaaa | agagaaaaga | aataaaaaact | tggatcaaaa | aaaaaacata cagatcttct | 480 |
| aattattaac | ttttcttaaa | aattaggtcc | ttttcccaa | caattaggtt tagagttttg | 540 |
| gaattaaacc | aaaaagattg | ttctaaaaaa | tactcaaatt | tggtagataa gtttccttat | 600 |
| tttaattagt | caatggtaga | tactttttt | tcttttcttt | attagagtag attagaatct | 660 |
| tttatgccaa | gtattgataa | attaaatcaa | gaagataaac | tatcataatc aacatgaaat | 720 |
| taaaagaaaa | atctcatata | tagtattagt | attctctata | tatattatga ttgcttattc | 780 |

```
ttaatgggtt gggttaacca agacatagtc ttaatggaaa gaatcttttt tgaacttttt    840
ccttattgat taaattcttc tatagaaaag aaagaaatta tttgaggaaa agtatataca    900
aaaagaaaaa tagaaaaatg tcagtgaagc agatgtaatg gatgacctaa tccaaccacc    960
accataggat gtttctactt gagtcggtct tttaaaaacg cacggtggaa aatatgacac   1020
gtatcatatg attccttcct ttagtttcgt gataataatc ctcaactgat atcttccttt   1080
ttttgttttg gctaaagata ttttattctc attaatagaa aagacggttt tgggcttttg   1140
gtttgcgata taaagaagac cttcgtgtgg aagataataa ttcatccttt cgtctttttc   1200
tgactcttca atctctccca aagcctaaag cgatctctgc aaatctctcg cgactctctc   1260
tttcaaggta tattttctga ttcttttttgt ttttgattcg tatctgatct ccaattttg   1320
ttatgtggat tattgaatct tttgtataaa ttgcttttga caatattgtt cgtttcgtca   1380
atccagcttc taaattttgt cctgattact aagatatcga ttcgtagtgt ttacatctgt   1440
gtaatttctt gcttgattgt gaaattagga ttttcaagga cgatctattc aattttgtg    1500
ttttctttgt tcgattctct ctgttttagg tttcttatgt ttagatccgt ttctctttgg   1560
tgttgttttg atttctctta cggcttttga tttggtatat gttcgctgat tggtttctac   1620
ttgttctatt gttttatttc aggtaggatc ctaaaccatg gctttggcta ttgtgggaga   1680
ggcacttatc tctgcttctg tggagatctt gctggatagg ataacttctg tggagtttcg   1740
aaatttcttt gccaatagaa agctgaatgt ttctctcttg gatgagctga agataaagct   1800
gttggcactc agtgctgtgc tcaatgatgc tgaggagaaa cagatcacta attcagaagt   1860
gaaggcatgg cttgatgagt tgaaagatgc tgttttagac gcagaggatt tgttggacca   1920
aatcaacaca gattctctga ggtgcaaggt ggaggaacaa tacaaaacct ttaaaagcca   1980
ggtgtggtca tcactttctt ctcccttttaa tcaattctat aggagcatga attccaagct   2040
tgaagcaata tctggaaggc tagaaaattt tatcaaacaa aaagatattc ttggtttgaa   2100
aagtgttgct ggcagagtct cttaccgaaa agatacagat cgatcggtgg aatatgttgt   2160
tgcaagagac gatgacaaaa agaagctgtt gaccatgctt ctctctgatg aagatgagaa   2220
taataatcac ataaaagtgc tgacaatatg gggcatggga ggtcttggaa aaacaaccct   2280
tgctcagagc cttttaaatg acgatgcagt gcagaaccat tttgatctca agcttgggc   2340
atgggtatct gatccttttg atgtgtttaa ggcaacgaag gcaattgttg aatctgccac   2400
ttcaaaaact tgtgatacta ctaattttga tgctcttcga gttgaattga agaacacctt   2460
taaagataaa ttttttttgc ttgtgctcga tgaccttttgg aatatgcagt atcatgattg   2520
ggatcaacta atagccccctt ttattagctg tgggaagaag ggaagtataa tcattgtgac   2580
aacccgacaa cacagaattg cagaaatcac tagtacattt cccattcacg agctgaagat   2640
tcttacagat gacaactgtt ggtgtatact tgctaaacat gcatttggaa atcaaggata   2700
tgacaaatat cccatcctag cagaaattgg tagacaaatt gcaacaaaat gcaagggtct   2760
accattagca gctaaaacat ggggaggtct tttgcgatca aatgttgatg cagagtattg   2820
gaatgaaatt ctgaacagca acatgtgggc aaataatgaa gttttaccag ctttatgcat   2880
aagttatctt caacttccac cacatctgaa aagatgtttt gcctattgct caattttttcc   2940
tagacaacat tgttggata ggaaggaatt gattctgtta tggatggctg aaggctttct   3000
tccacaaatc cacagagaga aagcaatgga atcagcaggt gaagactact tcaatgaatt   3060
gttatctaga tctttaattg aaaaagacaa aaatgaggga aaggaacagt ttcgaatgca   3120
```

```
tgaccttatc tacgatttag ccagactagt ctctggtaag agatcttgtt actttgaagg   3180
aggagaagtc ccaataaatg ttcgccatct gacatatcat cccagatatc ttgatgtctc   3240
tacaagattt gagggcttgt atgggctaaa gcttttgcgc agcttttac gactatctca    3300 atattctagt agtgtatcca aaagggtgac acatgagtgg ctgccaacac taacatatct   3360
gcgaacattg tccttgattc agtatagaaa tatcactgag ctgcctgatt caataagcaa   3420
tttggtactg ttgcggtatc ttgacctttc ctatacttcc atcaaaagtt tgcctgatgc   3480
aacctttagg ctttacaatt tgcagacttt gaaattatca cattgtgaac atcttacaga   3540
gttgactgaa cagataggag atttgttact tttacggtat cttgaccttt cctatacttc   3600
catcaatcag ctgcctgaac agataggaaa tttggtcaat ctacgccacc ttgatattag   3660
aggcacaaat ttgacggaga tgccagcaca aataagcaag ctacaagatc tccgtgtgtt   3720
gacttctttt gttgtaggca gagaagatgg agtaaatatc agagaattaa gaaagtttcc   3780
ttacttgcaa ggtacgcttt ccattttgag gttacaaaat gttgttgatc ccaaggatgc   3840
ttttcaagct gacttaaaga agaaagagca tattgaggag cttaggttgg agtggggcag   3900
tgagccacaa gattcacaaa ttgagaagaa tgtacttcag aacctgcaac catcgacaaa   3960
tttaaagaaa ctcagcgtaa gatactacag tggcacaagc tttcctaaat ggttgggtga   4020
ctcttcatat tcttatgtta tattcctttg catcactaat tgcaaatatt gcttttcact   4080
tccaccattt ggacaactac cttctctcaa ggagcttgtg ataaaaagga tgaaaatggt   4140
gaagacagtt ggtgaagaat tctactgcaa caatgggtt tcccttcat ttcaaccatt      4200 tccattgttg gagagtatcg agttcgaaga gatgtcagag tgggaagagt ggctaccatt   4260
tgaaggtgaa ggcagcaagt ttcctttcc ttgccttaaa catttgagtt tatcaaaatg     4320
ccccaagttg agaggaaact tgcccaacca tctaccttcc ttgacagagg ttagtatatc   4380
agagtgcaac cggctagagg caaaatcaca tgatctacat tggaacacat caattgaaga   4440
aataacgatt agagaagcag gagaacaatt gttgtccttg cttgacaact tttcttacag   4500
gaatctacgg attgaaaaat gtgacagctt gtcatctttg ccaagaatga tactagctgc   4560
caattgtctc caaggttga ctcttaagga tatccccaat ttgatttcct tcccagccga    4620
tggcttgcca acgtcattgc aatttcttga cattgacaac tgtgagaact tagaatttct   4680
gtctcccgaa tcatgccaca aatacacatc acttgaatat ctgtcaattg tcaatagctg   4740
ccattccctg gcatccttac cattagatgg tttctcttcc ctacaaagtc ttcaaatctt   4800
ggaatgtccc aacatggaag caattactac tcaaggtgga acgaatgctc tcaaattaac   4860
ttatctttat gtttataaat gtaagaaact taggtcactt ccagaacaga ttgatctccc   4920
tgcccttcaa tggttagggc tttctgagct tccagagctg acatcattgc ccccaaggtg   4980
tttgccttcc agtttagaaa cactcaaagt tgaagttgga atgctatcat caatgtctaa   5040
acacgagtta ggtttcctat tccaacgcct cacttctctg tctcgtcttt acattagtgg   5100
ttttggggag gaagatgttg ttaacaccct gttgaaggag tgcttactgc ccacttcgct   5160
gcaacatctg tccctatggt attttgatga tttaaagttg ttggaaggaa aagggctcca   5220
acatctcact tccctcagag atcttggcat caggaattgt aaaagcctcg agtccttgcc   5280
cgaagatcag cttccatcct ctcttgaatt actggagata catggttgtc ctttactaga   5340
agcaaggtat caaagtcgga aagggaaaca ctggtctaag attgctcaca ttcctgcgat   5400
caagataaat gatgaagtga taatatgaga gctcagcttt ttgtgatctg atgataagtg   5460
gttggttcgt gtctcatgca cttgggaggt gatctatttc acctggtgta gtttgtgttt   5520
```

```
ccgtcagttg gaaaaactta tccctatcga tttcgttttc attttctgct tttcttttat    5580
gtaccttcgt ttgggcttgt aacgggcctt tgtatttcaa ctctcaataa taatccaagt    5640
gcatgttaaa caatttgtca tctgtttcgg ctttgatata ctactggtga agatgggccg    5700
tactactgca tcacaacgaa aaataataat aagatgaaaa acttgaagtg gaaaaaaaaa    5760
aacttgaatg ttcactacta ctaattgacg gaccgctaat tagctaagag acacttgtgt    5820
gattgagaga aacactaatc ttgtgaggac tgaagtttgg tgattattc ttgtgatctg      5880
tcgacaaaaa tatcaaatgg ggtttctttt acaaattatt tacctaaatg aatctgttt      5940
gaaaatattt actccattgg gtctatttt ttattacaaa gcgtctccct gaagggcgcg      6000
ttccccgtga agtgacacg tggcaggact tgggacgtgc cctgcgtaca ggcgcgatag      6060
ttagtgttgt tacagcaggc gcatcgggtc gtgttgggga ccaaggtacg acaggtcgcg     6120
ctgggtgacc cagacacgac ccaattgggt cgcactttat ttaatatttt ttatattttg    6180
tatattgttt ttatttaata tattttata ttattttatt taattttttt atattttata     6240
taatagtttc tatattaaat aaattcttag cattatgtat gattttaaag tcataaataa    6300
ttttttatat tgtttttatt tactatattt tttatatttt atttaatatt tatatattaa    6360
ataaatcctt catattagaa aaataaaga aatattaaa taaaatataa aatataaaaa       6420
agtaaaaaat attaaataaa ataatataaa aaatatttata aaacaatat aaaaaatata    6480
aaatatttta ataaaataat aaaaaaata ttatttaaa taaaattatt tatgacttta      6540
aactctaaag ttgaatttta aaaaaatata atttttttac gattttagta aaaaaaaaat    6600
acaagccgca caatacaagt cgccttctca aacccttcct cacgacattc tcggaccta      6660
tgacaccgtc accaaaacaa tgatccacgc gatattaggc gcgtgcaaat cactctaatc    6720
cgaaactagt agacatggga agcacgagct atacgcgagc gtttcaattg ccgccacgaa    6780
agcagagaag gccagaaacg gaaccacggt aaaatggtaa gggtattttc gtaaacagaa    6840
gaaaagagtt gtagctataa ataaaccctc taacccacgg cgcactattt ctcttcactc    6900
cttcgttcac tcttcttctc ttgcggctag ggttttagcg cagcttcttc taggttcgtt    6960
ctcttccgcc gctctatgga ttttaaacct tcgaatcatg tttattccat tgaattatgt    7020
tgcttgcagt ttatattttc tgaatctgta gttgttgtct tcaatttatc ctatgcttta    7080
tagatcaatc ttttgtgtgt gtagtacgta attttgttc tttttgcttt tcgttcaagt     7140
tgttgggaat aatcggggta tcatgttttg atattgtttg ttttctttt tgactgctta     7200
ataattttta agttggtttt ggttttgggg ttttatgtgc ttgttatatt caaatctttg    7260
tgatccagat cttacaaaag ttgggtttt aaggatgttt ttggctgatg atgaatagat     7320
ctataaactg ttcccttta tcgattcaag cttaggattt tactaggctt ttgcgaataa    7380
atacgtgaca gtaagctaat tatgtccttt ttttgtctca atcatatctg tctgggtgtg    7440
ccataaattg tgatatgtct atctggtaga atcttgtgtt ttatgcttta cgatttggta    7500
tacctgtttt tgaacttgtt gtatgatggg tatttagatc accctatctt ttttatgctt    7560
ctggaagttt tatgtaaatg tcgaatatct taatgttgtt gaacttataa tgttgtgttg    7620
atgtatgtat gatggttttg acaacttttt tcactggttc tgaaagtttt atgtaaattg    7680
caaatatgtt aatgttgttg aacttatttt ttttccttcg atgttgtttt gatgtatgta    7740
tgatggtttt caccgtagtt tctatggcta atatcttaat gttgttgagc ttattttttt    7800
ccttatatgt tgtgttgatg tattgtatga tggttttgac aacttttta gtttctttgc     7860
```

```
agatttaagg aaggatcaaa aatggctgct gctgctgcag ctccatctcc atcattctct   7920
aagaccttgt cctcttcatc ctctaagtcc tctactcttt tgccaaggtc tactttccca   7980
ttcccacatc atccacataa gactactcca ccaccacttc atcttacccc aacccatatt   8040
cactctcaga gaagaaggtt caccatctct aacgttatct ccaccaccca aaaggtttca   8100
gagactcaaa aggctgagac tttcgtttct aggttcgctc cagatgagcc aagaaaggga   8160
tctgatgttc ttgttgaggc tcttgaaagg gaaggtgtta ctgatgtttt cgcttatcca   8220
ggtggcgctt ctatggaaat tcatcaagct cttaccaggt cctccatcat tagaaacgtt   8280
ttgccaagac atgagcaggg tggtgttttc gctgctgaag atatgctag agctactgga    8340 ttccctggtg tgtgtattgc tacttctgga ccaggtgcta ccaaccttgt ttctggactt   8400
gctgatgctc tccttgattc tgttccaatt gtggctatta ccggacaagt tgctagaagg   8460
atgattggaa ccgatgcttt ccaagagact ccaattgtgg aagtgaccag atctatcacc   8520
aagcacaact accttgtgat ggatgttgag gatattccaa gggttgtgag agaggcattc   8580
ttcttggcta gatctggtag accaggacca gttcttattg atgtgccaaa ggatattcag   8640
cagcagcttg ttatcccaga ttgggatcaa cctatgagac ttccaggtta catgtctagg   8700
cttccaaagc ttcctaacga gatgcttctt gagcagattg tgaggcttat ttccgagtct   8760
aagaagccag ttctctacgt tggtggtgga tgctctcaat cttctgagga acttagacgt   8820
ttcgttgagc ttaccggaat tccagttgct tctactctta tgggacttgg agctttccca   8880
actggtgatg aactttctct ttccatgctt ggaatgcatg gaaccgttta tgctaactac   8940
gctgtggatt cctccgatct tcttcttgct ttcggtgtta ggttcgatga tagagttacc   9000
ggaaagcttg aggctttcgc ttctagagct aagattgtgc acatcgatat cgattccgct   9060
gagattggaa agaacaagca gccacatgtg tccatttgcg ctgatattaa gcttgcactt   9120
cagggactca actccattct tgaatccaaa gagggaaagc tcaagcttga tttctctgct   9180
tggaggcaag agcttactgt tcagaaggtt aagtaccccc tcaacttcaa gactttcgga   9240
gatgctattc caccacagta cgctattcaa gtgcttgatg agcttaccaa cggctctgct   9300
attatttcta ctggtgttgg acagcatcag atgtgggctg ctcaatatta caagtacaga   9360
aagccaaggc agtggcttac ttctggtgga cttggtgcta tgggattcgg acttccagct   9420
gctattggag ctgctgttgg tagaccagat gaagttgttg tggatatcga tggtgatggc   9480
tccttcatta tgaacgttca agagcttgcc accatcaagg ttgaaaacct tccagtgaag   9540
atcatgctcc ttaacaacca gcatcttgga atggttgtgc aacttgagga cagattctac   9600
aaggctaaca gggctcatac ctatcttgga aacccatcta acgaggctga gattttccca   9660
aacatgctta agttcgctga ggcttgcgga gttcctgctg ctagagttac tcatagagat   9720
gatctcaggg ctgctattca gaagatgctt gatactccag gaccatacct tctcgatgtt   9780
attgtgccac atcaagagca tgtgctccca atgattccat ctggtggtgc tttcaaggat   9840
gttattactg agggtgatgg aaggtcctcc tactaagtgc tagcatttg tacattgagt    9900 agggaagaga gagagatata tataaatact cacaaagcag tgagtatatg cttgctttt    9960 gtttctaaac attcctttat aaggacttga gataatttgt attgtttaaa agagccattg  10020
gttctgttgt atcaaagtaa tttaattttc agtaccgact tggctctact catatgtggt  10080
ggtgtacatt gcatctttgc atttgattcc atatctattg ggatgggacc atacatttt   10140 tgtttattat ttaagtcaaa catatcagat aaatatgtgg gaccagaaaa gtgtctagca  10200
atcaaatggg tctgtgattg catgtttgag ttcaggacat ttattaatga gtgacagaat  10260
```

```
tttaaaaagc tcgccaatag gagttgccac atctgatcga gtcttctgta aacactaact   10320
gtaacttgag tttgataatc agattccccc cgttggtagg taatatgtaa atttcactat   10380
agattcttac tgaggatgat ggtcttgact tcgaagtggt gagtgtaatt ctctaatcta   10440
aactttatat atatataaaa aaagaatgtt aaaaacttga gtgacataca gcaaatagca   10500
atgaaagcat gaccattggc cttgggggc caaatggcca tgtaccactt ttccacctac    10560
ttgagagcca ttggtcctga atgaggtcct tttgtttcat ttttttttaca ataaagaaag  10620 ttcatattct tggcaatagc aaggcaaatc atttgtggaa gtcacatgaa attcaccata   10680
ctaattagct aacggacccg atttaaatcg gtaccactag taatattcgg accccctgca   10740
ggcccggggg cgcgccctaa ttagctaacg gccaggatcg ccgcgtgagc ctttagcaac   10800
tagctagatt aattaacgca atctgttatt aagttgtcta agcgtcaatt tgtttacacc   10860
acaatatatc ctgccaccag ccagccaaca gctccccgac cggcagctcg gcacaaaatc   10920
accactcgat acaggcagcc catcagaatt aattctcatg tttgacagct tatcatcgac   10980
tgcacggtgc accaatgctt ctggcgtcag gcagccatcg gaagctgtgg tatggctgtg   11040
caggtcgtaa atcactgcat aattcgtgtc gctcaaggcg cactcccgtt ctggataatg   11100 tttttttgcgc cgacatcata acggttctgg caaatattct gaaatgagct gttgacaatt   11160
aatcatccgg ctcgtataat gtgtggaatt gtgagcggat aacaatttca cacaggaaac   11220
agaccatgag ggaagcgttg atcgccgaag tatcgactca actatcagag gtagttggcg   11280
tcatcgagcg ccatctcgaa ccgacgttgc tggccgtaca tttgtacggc tccgcagtgg   11340
atggcggcct gaagccacac agtgatattg atttgctggt tacggtgacc gtaaggcttg   11400
atgaaacaac gcggcgagct ttgatcaacg acctttggga aacttcggct tcccctggag   11460
agagcgagat tctccgcgct gtagaagtca ccattgttgt gcacgacgac atcattccgt   11520
ggcgttatcc agctaagcgc gaactgcaat ttggagaatg gcagcgcaat gacattcttg   11580
caggtatctt cgagccagcc acgatcgaca ttgatctggc tatcttgctg acaaaagcaa   11640
gagaacatag cgttgccttg gtaggtccag cggcggagga actctttgat ccggttcctg   11700
aacaggatct atttgaggcg ctaaatgaaa ccttaacgct atggaactcg ccgcccgact   11760
gggctggcga tgagcgaaat gtagtgctta cgttgtcccg catttggtac agcgcagtaa   11820
ccggcaaaat cgcgccgaag gatgtcgctg ccgactgggc aatggagcgc ctgccggccc   11880
agtatcagcc cgtcatactt gaagctaggc aggcttatct tggacaagaa gatcgcttgg   11940
cctcgcgcgc agatcagttg gaagaatttg ttcactacgt gaaaggcgag atcaccaaag   12000
tagtcggcaa ataaagctct agtggatctc cgtacccagg gatctggctc gcggcggacg   12060
cacgacgccg gggcgagacc ataggcgatc tcctaaatca atagtagctg taacctcgaa   12120
gcgtttcact tgtaacaacg attgagaatt tttgtcataa aattgaaata cttggttcgc   12180
atttttgtca tccgcggtca gccgcaattc tgacgaactg cccatttagc tggagatgat   12240
tgtacatcct tcacgtgaaa atttctcaag cgctgtgaac aagggttcag attttagatt   12300
gaaaggtgag ccgttgaaac acgttcttct tgtcgatgac gacgtcgcta tgcggcatct   12360
tattattgaa taccttacga tccacgcctt caaagtgacc gcggtagccg acagcaccca   12420
gttcacaaga gtactctctt ccgcgacggt cgatgtcgtg gttgttgatc tagatttagg   12480
tcgtgaagat gggctcgaga tcgttcgtaa tctggcggca aagtctgata ttccaatcat   12540
aattatcagt ggcgaccgcc ttgaggagac ggataaagtt gttgcactcg agctaggagc   12600
```

```
aagtgatttt atcgctaagc cgttcagtat cagagagttt ctagcacgca ttcgggttgc   12660
cttgcgcgtg cgccccaacg ttgtccgctc caaagaccga cggtctttt  gttttactga   12720 ctggacactt aatctcaggc aacgtcgctt gatgtccgaa gctggcggtg aggtgaaact   12780
tacggcaggt gagttcaatc ttctcctcgc gttttagag  aaaccccgcg acgttctatc   12840
gcgcgagcaa cttctcattg ccagtcgagt acgcgacgag gaggtttatg acaggagtat   12900
agatgttctc attttgaggc tgcgccgcaa acttgaggca gatccgtcaa gccctcaact   12960
gataaaaaca gcaagaggtg ccggttattt ctttgacgcg gacgtgcagg tttcgcacgg   13020
ggggacgatg gcagcctgag ccaattccca gatccccgag gaatcggcgt gagcggtcgc   13080
aaaccatccg gcccggtaca aatcggcgcg gcgctgggtg atgacctggt ggagaagttg   13140
aaggccgcgc aggccgccca gcggcaacgc atcgaggcag aagcacgccc cggtgaatcg   13200
tggcaagcgg ccgctgatcg aatccgcaaa gaatcccggc aaccgccggc agccggtgcg   13260
ccgtcgatta ggaagccgcc caagggcgac gagcaaccag attttttcgt tccgatgctc   13320
tatgacgtgg gcacccgcga tagtcgcagc atcatggacg tggccgtttt ccgtctgtcg   13380
aagcgtgacc gacgagctgg cgaggtgatc cgctacgagc ttccagacgg gcacgtagag   13440
gtttccgcag ggccggccgg catggccagt gtgtgggatt acgacctggt actgatggcg   13500
gtttcccatc taaccgaatc catgaaccga taccggaag  ggaagggaga caagcccggc   13560
cgcgtgttcc gtccacacgt tgcggacgta ctcaagttct gccggcgagc cgatggcgga   13620
aagcagaaag acgacctggt agaaacctgc attcggttaa acaccacgca cgttgccatg   13680
cagcgtacga agaaggccaa gaacggccgc ctggtgacgg tatccgaggg tgaagccttg   13740
attagccgct acaagatcgt aaagagcgaa accgggcggc cggagtacat cgagatcgag   13800
ctggctgatt ggatgtaccg cgagatcaca gaaggcaaga accccgacgt gctgacggtt   13860
caccccgatt acttttgat  cgatcccggc atcggccgtt ttctctaccg cctggcacgc   13920
cgcgccgcag gcaaggcaga agccagatgg ttgttcaaga cgatctacga acgcagtggc   13980
agcgccggag agttcaagaa gttctgtttc accgtgcgca agctgatcgg gtcaaatgac   14040
ctgccggagt acgatttgaa ggaggaggcg gggcaggctg gcccgatcct agtcatgcgc   14100
taccgcaacc tgatcgaggg cgaagcatcc gccggttcct aatgtacgga gcagatgcta   14160
gggcaaattg ccctagcagg ggaaaaaggt cgaaaaggtc tctttcctgt ggatagcacg   14220
tacattggga acccaaagcc gtacattggg aaccggaacc cgtacattgg gaacccaaag   14280
ccgtacattg gaaccggtc  acacatgtaa gtgactgata taaaagagaa aaaaggcgat   14340
ttttccgcct aaaactcttt aaaacttatt aaaactctta aaacccgcct ggcctgtgca   14400
taactgtctg gccagcgcac agccgaagag ctgcaaaaag cgcctaccct tcggtcgctg   14460
cgctccctac gccccgccgc ttcgcgtcgg cctatcgcgg ccgctggccg ctcaaaaatg   14520
gctggcctac ggccaggcaa tctaccaggg cgcggacaag ccgcgccgtc gccactcgac   14580
cgccggcgct gaggtctgcc tcgtgaagaa ggtgttgctg actcatacca ggcctgaatc   14640
gccccatcat ccagccagaa agtgagggag ccacggttga tgagagcttt gttgtaggtg   14700
gaccagttgg tgattttgaa cttttgcttt gccacggaac ggtctgcgtt gtcgggaaga   14760
tgcgtgatct gatccttcaa ctcagcaaaa gttcgattta ttcaacaaag ccgccgtccc   14820
gtcaagtcag cgtaatgctc tgccagtgtt acaaccaatt aaccaattct gattagaaaa   14880
actcatcgag catcaaatga aactgcaatt tattcatatc aggattatca ataccatatt   14940
tttgaaaaag ccgtttctgt aatgaaggag aaaactcacc gaggcagttc cataggatgg   15000
```

```
caagatcctg gtatcggtct gcgattccga ctcgtccaac atcaatacaa cctattaatt    15060 tccctcgtc aaaataagg ttatcaagtg agaaatcacc atgagtgacg actgaatccg     15120
gtgagaatgg caaaagctct gcattaatga atcggccaac gcgcggggag aggcggtttg    15180
cgtattgggc gctcttccgc ttcctcgctc actgactcgc tgcgctcggt cgttcggctg    15240
cggcgagcgg tatcagctca ctcaaaggcg gtaatacggt tatccacaga atcaggggat    15300
aacgcaggaa agaacatgtg agcaaaaggc cagcaaaagg ccaggaaccg taaaaaggcc    15360
gcgttgctgg cgttttttcca taggctccgc cccctgacg agcatcacaa aaatcgacgc    15420
tcaagtcaga ggtggcgaaa cccgacagga ctataaagat accaggcgtt ccccctgga    15480 agctccctcg tgcgctctcc tgttccgacc ctgccgctta ccggatacct gtccgccttt    15540
ctcccttcgg gaagcgtggc gctttctcat agctcacgct gtaggtatct cagttcggtg    15600
taggtcgttc gctccaagct gggctgtgtg cacgaacccc ccgttcagcc cgaccgctgc    15660
gccttatccg gtaactatcg tcttgagtcc aacccggtaa gacacgactt atcgccactg    15720
gcagcagcca ctggtaacag gattagcaga gcgaggtatg taggcggtgc tacagagttc    15780
ttgaagtggt ggcctaacta cggctacact agaagaacag tatttggtat ctgcgctctg    15840
ctgaagccag ttaccttcgg aaaaagagtt ggtagctctt gatccggcaa acaaaccacc    15900
gctggtagcg gtggtttttt tgtttgcaag cagcagatta cgcgcagaaa aaaggatct    15960 caagaagatc ctttgatctt ttctacgggg tctgacgctc agtggaacga aaactcacgt    16020
taagggattt tggtcatgag attatcaaaa aggatcttca cctagatcct tttgatccgg    16080
aatta                                                              16085

<210> SEQ ID NO 6
<211> LENGTH: 1998
<212> TYPE: DNA
<213> ORGANISM: Glycine max

<400> SEQUENCE: 6
attccaaaat tttcagttag tccttactaa ttattaaatt atagtattaa tccaatgtga     60
ttgcggttac atcatgtacg gaaaaataat tctaatcctt gttttaaatt tgatcttgac    120
tatttattta ttctttatt cattttgtaa atcatttat gtatctcctg caagcaatt     180 ttatccacct tgcaccaaca ccttcgggtt ccataatcaa accaccttaa cttcacacca    240
tgctgtaact cacaccgccc agcatctcca atgtgaaaga agctaaaatt taataaacaa    300
tcatacgaag cagtgacaaa ataccagatg gtattaatgc tttgataaaa ttaattggaa    360
agtataaaat ggtagaaaat aataaattat aattatttta ataagataa aaaataatta    420 aaaactaaaa tgttaaaatt ttaaaaaaat tattttaaat aatatttaaa aacattaaaa    480 atcatttaa aaaatttatt tatagaacaa ttaaataaat atttcagcta ataaaaaaca    540
aaagcttacc tagccttaga agacaacttg tccaacaatt agatgatacc cattgccctt    600
acgttttctt taacatcaat tattgttttt gtcaacaagc tatctttag ttttattta    660 ttggtaaaaa atatgtcgcc ttcaagttgc atcatttaac acatctcgtc attagaaaaa    720
taaaactctt ccctaaacga ttagtagaaa aaatcattcg ataataaata agaagaaaa    780 attagaaaaa aataacttca ttttaaaaaa atcattaagg ctatattttt taaatgacta    840
attttatata gactgtaact aaaagtatac aatttattat gctatgtatc ttaaagaatt    900
acttataaaa atctacggaa gaatatctta caaagtgaaa aacaaatgag aagaattta    960
```

```
gtgggatgat tatgatttta tttgaaaatt gaaaaaataa ttattaaaga ctttagtgga    1020
gtaagaaagc tttcctatta gtctttcctt atccataaaa aaaaaaaaaa atctagcgtg    1080
acagcttttc catagatttt aataatgtaa aatactggta gcagccgacc gttcaggtaa    1140
tggacactgt ggtcctaact tgcaacgggt gcgggcccaa tttaataacg ccgtggtaac    1200
ggataaagcc aagcgtgaag cggtgaaggt acatctctga ctccgtcaag attacgaaac    1260
cgtcaactac gaaggactcc ccgaaatatc atctgtgtca taaacaccaa gtcacaccat    1320
acatgggcac gcgtcacaat ttgattggag aacggttcca ccgcatatgc tataaattgc    1380
ccccacaccc ctcgacccta atcgcacttc aattgcaatc aaattagttc attctctttg    1440
cgcagttccc tacctctcct ttcaaggttc gtagatttct tctgtttttt tttcttcttc    1500
tttattgttt gttctacatc agcatgatgt tgatttgatt gtgttttcta tcgtttcatc    1560
gattataaat tttcataatc agaagattca gcttttatta atgcaagaac gtccttaatt    1620
gatgatttta taaccgtaaa ttaggtctaa ttagagtttt tttcataaag attttcagat    1680
ccgtttacaa caagccttaa ttgttgattc tgtagtcgta gattaaggtt ttttttcatga   1740
actacttcag atccgttaaa caacagcctt atttgttgat acttcagtcg tttttcaaga    1800
aattgttcag atccgttgat aaaagcctta ttcgttgatt ctgtatggta tttcaagaga    1860
tattgctcag gtcctttagc aactacctta tttgttgatt ctgtggccat agattaggat    1920
tttttttcac gaaattgctt cttgaaatta cgtgatggat tttgattctg atttatcttg    1980
tgattgttga ctctacag                                                  1998

<210> SEQ ID NO 7
<211> LENGTH: 1730
<212> TYPE: DNA
<213> ORGANISM: Glycine tomentella

<400> SEQUENCE: 7
taaatattta aatatatttt gatatgcaca catatttcaa aaaattgtta ttttgttgtg      60
ttctaggtag aattttcttc acattaataa tgtcttgcat gctcctttt tactttcttt     120
taaacaaagt tgatttattt tatttttattt tattttgtaa ttgtgttatc agtacaaatt    180
atttaatggt tttgttcatg attattttt gtcaaaaaat aacacctata tccacgtaat     240
aatacattct tttataatac attttaaaat taaattaatt aaatatgtta aagttatcaa    300
tatatacatt tcttaggtcc tatgttattt gggaatccgt tagacttgca aggctttgat    360
ttttattcta cagggatctc taatttaggc tatgttttgt tttgatttaa ttatattttt    420
tttagttctc actcatattt taatttatgg gaaatttat agtattttaa attttaattc    480
tttatacttt atttttatac aatttaatta ttaaaattaa gttcctcatt tcaaatttca    540
tccaataacg tatgaataaa agattgtgag gtgactttga tttatacaaa ttggtgtaag    600
aaagataaat atatattaag agaaaaaaaa taacttcttg taaggacaca ttatcacata    660
atgtattgta aggacttcaa tgtaagaaat tgtgaatcaa actatcgac cactcctatt     720
actactttat tgtcattgta taaatattta tttaaggcaa cttaatcaca tcctcaaatt    780
tgaaaaaagt atttttttc aattttatt ctccatgtcc agtatcattg cccttaaaaa     840
gctaaaaaaa aaacatatat agatgtgcaa tctaaaatac atgatttctt tattaataat    900
aatcatttaa tatcttacca aattattatc aatttgccac agcatgtcaa ttttttttttg   960
ttcatagtaa tctattactt tatttttata cactttatac gaataaataa ataaattaaa   1020
aatttgcaac aataaacaat tatatgtaaa ttattaaaac tttttttgaag gaataaatta   1080
```

```
tcataacttt aataatataa attattattt ttaattaaat ataaaaaatg atagccaaaa    1140
aattatacat gatgaagttt aaacttaata tccgtgcaag gcacaccgga ttttacgcta    1200 gtaaattta actaaaatta cacatgttaa attaaaggga tcagaagtgt aattatttta    1260 ttttatttt tttaaaaatc atcttaaaat aatacaagta ataagtaatt attctaaaaa    1320
tttgattcct ccgagagtga aactttcaac tacctaatgc aaactttgtc aaagtgaaat    1380
ttgactacac ccagcaaact ttgtaagcaa tgttgcaatg ttctaagagt taatctcata    1440
gctattcttg taaggactcc gaatcaatta aagacaaaga gtagggaatc taacttttc    1500 aacaacaaat taattacatg cacgatagtg taggccgttt aagaaagttt aagagagtaa    1560
ctgatatgtg gcatcttaga tatatactaa gcaaataata ttgcataata gaacatgaaa    1620
tcatgaatgc tgatttaaaa gcattaaaca aacgaattga ggaatgaggg aggtgtcaag    1680
ttttaggaat tcagaaaaat gtataattaa ctcttattaa gtttttttt                1730
```

<210> SEQ ID NO 8
<211> LENGTH: 1422
<212> TYPE: DNA
<213> ORGANISM: Arabidopsis

<400> SEQUENCE: 8

```
ccggttcaac attttttttg ttttgagtta ttatctgggc ttaataacgc aggcctgaaa      60
taaattcaag gcccaactgt tttttttttt aagaagttgc tgttaaaaaa aaaaaaaggg     120
aattaacaac aacaacaaaa aaagataaag aaaataataa caattacttt aattgtagac     180
taaaaaaaca tagattttat catgaaaaaa agagaaaaga aataaaaact tggatcaaaa     240
aaaaaacata cagatcttct aattattaac ttttcttaaa aattaggtcc ttttcccaa     300 caattaggtt tagagttttg gaattaaacc aaaaagattg ttctaaaaaa tactcaaatt     360
tggtagataa gtttccttat tttaattagt caatggtaga tacttttttt tcttttcttt     420
attagagtag attagaatct tttatgccaa gtattgataa attaaatcaa gaagataaac     480
tatcataatc aacatgaaat taaagaaaaa atctcatata tagtattagt attctctata     540
tatattatga ttgcttattc ttaatgggtt gggttaacca agacatagtc ttaatggaaa     600
gaatcttttt tgaactttt ccttattgat taaattcttc tatagaaaag aaagaaatta     660
tttgaggaaa agtatataca aaagaaaaa tagaaaatg tcagtgaagc agatgtaatg     720
gatgacctaa tccaaccacc accataggat gtttctactt gagtcggtct tttaaaaacg     780
cacggtggaa aatatgacac gtatcatatg attccttcct ttagtttcgt gataataatc     840
ctcaactgat atcttccttt ttttgttttg gctaaagata ttttattctc attaatagaa     900
aagacggttt tgggcttttg gtttgcgata taaagaagac cttcgtgtgg aagataataa     960
ttcatccttt cgtcttttc tgactcttca atctctccca aagcctaaag cgatctctgc    1020
aaatctctcg cgactctctc tttcaaggta tattttctga ttcttttgt tttgattcg    1080 tatctgatct ccaattttg ttatgtggat tattgaatct tttgtataaa ttgcttttga    1140
caatattgtt cgtttcgtca atccagcttc taaattttgt cctgattact aagatatcga    1200
ttcgtagtgt ttacatctgt gtaatttctt gcttgattgt gaaattagga ttttcaagga    1260
cgatctattc aatttttgtg ttttctttgt tcgattctct ctgtttaggg tttcttatgt    1320
ttagatccgt ttctctttgg tgttgttttg atttctctta cggcttttga tttggtatat    1380
gttcgctgat tggtttctac ttgttctatt gttttatttc ag                     1422
```

```
<210> SEQ ID NO 9
<211> LENGTH: 30
<212> TYPE: DNA
<213> ORGANISM: artificial
<220> FEATURE:
<223> OTHER INFORMATION: TQ2681 probe

<400> SEQUENCE: 9
agcttttgcg cagcttttta cgactatctc                                          30

<210> SEQ ID NO 10
<211> LENGTH: 27
<212> TYPE: DNA
<213> ORGANISM: artificial
<220> FEATURE:
<223> OTHER INFORMATION: TQ2681 primer

<400> SEQUENCE: 10
gtcacccttt tggatacact actagaa                                             27

<210> SEQ ID NO 11
<211> LENGTH: 22
<212> TYPE: DNA
<213> ORGANISM: artificial
<220> FEATURE:
<223> OTHER INFORMATION: TQ2681 primer

<400> SEQUENCE: 11
caagatttga gggcttgtat gg                                                  22

<210> SEQ ID NO 12
<211> LENGTH: 1237
<212> TYPE: PRT
<213> ORGANISM: Glycine tomentella

<400> SEQUENCE: 12
```

Met Ala Leu Ala Met Val Gly Glu Ala Leu Ile Ser Ala Ser Val Glu
1               5                   10                  15

Ile Leu Leu Asp Arg Ile Thr Ser Thr Glu Phe Arg Asp Phe Phe Ala
            20                  25                  30

Asn Arg Asn Leu Asn Val Ser Leu Leu Asp Glu Leu Lys Ile Lys Leu
        35                  40                  45

Leu Ala Leu Asn Ala Val Leu Asn Asp Ala Glu Glu Lys Gln Ile Thr
    50                  55                  60

Asn Ser Ala Val Lys Gly Trp Leu Asp Glu Leu Lys Asp Ala Val Leu
65                  70                  75                  80

Asp Ala Glu Asp Leu Met Asp Glu Ile Asn Thr Asp Ser Leu Arg Cys
                85                  90                  95

Lys Val Glu Gly Glu Phe Lys Thr Phe Thr Ser Gln Val Trp Ser Ser
            100                 105                 110

Leu Ser Ser Pro Phe Asn Gln Phe Tyr Arg Ser Met Asn Ser Lys Leu
        115                 120                 125

Glu Ala Ile Ser Gly Arg Leu Glu His Phe Met Lys Gln Lys Asp Ile
    130                 135                 140

Leu Gly Leu Gln Ser Val Ser Arg Lys Val Ser Tyr Lys Thr Val Thr
145                 150                 155                 160

Asp Ser Leu Val Glu Ser Val Val Ala Arg Glu Asp Asp Lys Glu
                165                 170                 175

Lys Leu Leu Ser Met Leu Leu Ser Asp Glu Asp Glu Lys Asn Asn Asn
            180                 185                 190

```
Ile Glu Val Leu Thr Ile Leu Gly Met Gly Gly Leu Gly Lys Thr Thr
            195                 200                 205
Leu Ala Gln Cys Leu Tyr Asn Asp Ser Ala Val Gln Lys His Phe Asp
        210                 215                 220
Leu Thr Thr Trp Ala Trp Val Ser Asp Phe Asp Val Phe Arg Val
225                 230                 235                 240
Thr Lys Thr Ile Val Glu Ser Val Thr Ser Lys Asn Cys Asn Ser Thr
                245                 250                 255
Asn Phe Asp Ala Leu Arg Val Glu Leu Lys Asn Ser Leu Lys Asp Lys
            260                 265                 270
Lys Phe Leu Leu Val Leu Asp Asp Leu Trp Asn Glu Lys Tyr Asn Asp
        275                 280                 285
Trp His His Leu Ile Ala Pro Phe Ser Gly Lys Lys Gly Ser Lys
    290                 295                 300
Ile Ile Val Thr Thr Arg Gln Gln Lys Val Ala Gln Met Thr His Thr
305                 310                 315                 320
Tyr Pro Val Tyr Glu Leu Lys His Leu Thr Asp Asp Asn Cys Trp Cys
                325                 330                 335
Ile Leu Ala Glu His Ala Phe Gly Asn Glu Gly Tyr Asp Glu Tyr Pro
            340                 345                 350
Ile Leu Glu Glu Ile Gly Arg Lys Ile Ala Lys Lys Cys Asn Gly Leu
        355                 360                 365
Pro Leu Ala Ala Lys Thr Leu Gly Gly Leu Leu Arg Ser Asn Val Asp
    370                 375                 380
Ala Lys Glu Trp Asn Arg Ile Leu Asn Ser Asn Leu Trp Ala His Glu
385                 390                 395                 400
Glu Val Leu Pro Ala Leu His Ile Ser Tyr Leu His Leu Pro Ala His
                405                 410                 415
Leu Lys Arg Cys Phe Ser Tyr Cys Ser Ile Phe Pro Lys Gln His Leu
            420                 425                 430
Leu Asp Arg Lys Glu Leu Ile Leu Leu Trp Met Ala Glu Gly Phe Leu
        435                 440                 445
Gln Gln Ile His Gly Glu Lys Ala Met Glu Leu Ala Gly Asp Asp Tyr
    450                 455                 460
Phe Asn Glu Leu Leu Ser Arg Ser Leu Ile Glu Lys Asp Lys Thr Glu
465                 470                 475                 480
Ala Glu Asp Lys Phe Arg Met His Asp Leu Ile Tyr Asp Leu Ala Arg
                485                 490                 495
Leu Ile Ala Gly Lys Asn Ser Cys Tyr Leu Glu Gly Asn Lys Ile Ser
            500                 505                 510
Gly Gly Val Arg Gln Leu Ala Phe Tyr Ser Arg Lys Phe Asp Val Ser
        515                 520                 525
Glu Arg Phe Glu Gly Leu His Asp Leu Lys Phe Leu Arg Thr Phe Leu
    530                 535                 540
Arg Leu Phe Lys Tyr Gly Pro Phe Ser Tyr Gly His Val Thr Lys Lys
545                 550                 555                 560
Val Ser His Asp Trp Leu Pro Lys Leu Lys Tyr Leu Arg Thr Leu Ser
                565                 570                 575
Leu Leu Gly Tyr Glu Asn Ile Thr Glu Leu Pro Asp Ser Ile Ser Asn
            580                 585                 590
Leu Val Leu Leu Arg Tyr Leu Asp Leu Ser Tyr Thr Ser Ile Lys Arg
        595                 600                 605
```

```
Leu Pro Asp Ala Thr Phe Arg Leu Tyr Asn Leu Gln Thr Leu Lys Leu
    610                 615                 620

Ser Asn Cys Lys Cys Leu Thr Gln Leu Pro Glu Gln Ile Gly Asn Leu
625                 630                 635                 640

Val Asn Leu Arg His Leu Asp Ile Arg Gly Thr Asn Leu Thr Glu Met
                645                 650                 655

Pro Ala Gln Ile Ser Lys Leu Gln Asp Leu Arg Val Leu Thr Ser Phe
        660                 665                 670

Val Val Gly Arg Glu Asp Gly Val Asn Ile Arg Glu Leu Arg Lys Phe
            675                 680                 685

Pro Tyr Leu Gln Gly Thr Leu Ser Ile Leu Gly Leu Gln Asn Val Val
    690                 695                 700

Asp Pro Lys His Ala Phe Gln Ala Asp Leu Lys Lys Lys Glu His Val
705                 710                 715                 720

Glu Glu Leu Thr Leu Glu Trp Gly Ser Glu Pro Gln Tyr Ser Gln Leu
                725                 730                 735

Glu Lys Asp Val Leu Gln Asn Leu Gln Pro Ser Thr Asn Leu Lys Lys
            740                 745                 750

Leu Thr Ile Arg Tyr Tyr Ser Gly Thr Ser Phe Pro Lys Trp Leu Gly
        755                 760                 765

Asp Ser Ser Tyr Ser Tyr Val Ile Phe Leu Cys Ile Thr Asn Cys Lys
770                 775                 780

Tyr Cys Phe Ser Leu Pro Pro Phe Gly Gln Leu Pro Ser Leu Lys Glu
785                 790                 795                 800

Leu Val Ile Lys Arg Met Lys Met Val Lys Thr Val Gly Glu Glu Phe
                805                 810                 815

Tyr Cys Asn Asn Gly Val Ser Leu Ser Phe Gln Pro Phe Pro Leu Leu
            820                 825                 830

Glu Ser Ile Gln Phe Glu Glu Met Ser Glu Trp Glu Glu Trp Leu Pro
        835                 840                 845

Phe Glu Gly Glu Gly Ser Lys Phe Pro Phe Pro Cys Leu Lys His Leu
850                 855                 860

Ser Leu Ser Lys Cys Pro Lys Leu Arg Gly Asn Leu Pro Asn His Leu
865                 870                 875                 880

Pro Ser Leu Thr His Val Arg Ile Ser Glu Cys Asn Lys Leu Glu Ala
                885                 890                 895

Lys Ser His Asp Leu His Trp Asn Thr Ser Ile Glu Glu Ile Lys Val
            900                 905                 910

Arg Glu Ala Gly Glu Asp Leu Leu Ser Leu Leu Asp Asn Phe Ser Tyr
        915                 920                 925

Arg Asn Leu Arg Ile Lys Lys Cys Asp Ser Leu Ser Ser Leu Pro Arg
930                 935                 940

Met Ile Leu Ala Ala Asn Cys Leu Gln Arg Leu Thr Leu Lys Asp Ile
945                 950                 955                 960

Pro Asn Leu Ile Ser Phe Pro Ala Asp Gly Leu Pro Thr Ser Leu Gln
                965                 970                 975

Ser Leu Ser Ile Phe Asp Cys Gly Asn Leu Glu Phe Leu Ser Pro Glu
            980                 985                 990

Ser Cys His Lys Tyr Thr Ser Leu  Glu Tyr Leu Ser Ile  Val Asn Ser
        995                 1000                 1005

Cys His  Ser Leu Ala Ser Leu  Pro Leu Asp Gly Phe  Ser Ser Leu
    1010                 1015                 1020
```

| Gln | Arg | Leu | Gln | Ile | Gln | Lys | Cys | Pro | Asn | Met | Glu | Ala | Ile | Thr |
|     | 1025 |     |     |     | 1030 |     |     |     |     | 1035 |     |     |     |     |

| Thr | Gln | Gly | Gly | Thr | Asn | Ala | Leu | Lys | Leu | Thr | His | Leu | Tyr | Val |
|     | 1040 |     |     |     |     | 1045 |     |     |     |     | 1050 |     |     |     |

| Arg | Asp | Cys | Lys | Lys | Leu | Arg | Ser | Leu | Pro | Glu | Gln | Ile | His | Leu |
|     | 1055 |     |     |     |     | 1060 |     |     |     |     | 1065 |     |     |     |

| Pro | Ala | Leu | Arg | Trp | Leu | Glu | Leu | Ser | Lys | Leu | Pro | Glu | Leu | Ile |
|     | 1070 |     |     |     |     | 1075 |     |     |     |     | 1080 |     |     |     |

| Ser | Leu | Pro | Pro | Arg | Cys | Leu | Pro | Ser | Ser | Leu | Gln | Val | Leu | Glu |
|     | 1085 |     |     |     |     | 1090 |     |     |     |     | 1095 |     |     |     |

| Val | Glu | Val | Gly | Met | Leu | Ser | Ser | Met | Ser | Lys | His | Glu | Leu | Gly |
|     | 1100 |     |     |     |     | 1105 |     |     |     |     | 1110 |     |     |     |

| Phe | Leu | Phe | Gln | Arg | Leu | Thr | Ser | Leu | Ser | Ser | Leu | Glu | Ile | Ser |
|     | 1115 |     |     |     |     | 1120 |     |     |     |     | 1125 |     |     |     |

| Gly | Tyr | Gly | Glu | Glu | Asp | Val | Val | Asn | Thr | Leu | Leu | Lys | Glu | Cys |
|     | 1130 |     |     |     |     | 1135 |     |     |     |     | 1140 |     |     |     |

| Leu | Leu | Pro | Thr | Ser | Leu | Gln | Tyr | Leu | Cys | Leu | Val | Lys | Phe | Asp |
|     | 1145 |     |     |     |     | 1150 |     |     |     |     | 1155 |     |     |     |

| Asp | Leu | Lys | Leu | Leu | Glu | Gly | Lys | Gly | Leu | Gln | Gln | Leu | Thr | Ser |
|     | 1160 |     |     |     |     | 1165 |     |     |     |     | 1170 |     |     |     |

| Leu | Arg | Gly | Phe | Gly | Ile | Arg | Asn | Cys | Lys | Ser | Leu | Glu | Ser | Leu |
|     | 1175 |     |     |     |     | 1180 |     |     |     |     | 1185 |     |     |     |

| Pro | Glu | Asp | Gln | Leu | Pro | Ser | Ser | Leu | Glu | Leu | Leu | Glu | Ile | His |
|     | 1190 |     |     |     |     | 1195 |     |     |     |     | 1200 |     |     |     |

| Gly | Cys | Pro | Leu | Leu | Glu | Ala | Arg | Tyr | Gln | Ser | Arg | Lys | Gly | Lys |
|     | 1205 |     |     |     |     | 1210 |     |     |     |     | 1215 |     |     |     |

| His | Trp | Ser | Lys | Ile | Ala | His | Ile | Pro | Ala | Ile | Glu | Ile | Asn | Asp |
|     | 1220 |     |     |     |     | 1225 |     |     |     |     | 1230 |     |     |     |

| Glu | Val | Ile | Ile |
|     | 1235 |     |     |

<210> SEQ ID NO 13
<211> LENGTH: 3714
<212> TYPE: DNA
<213> ORGANISM: Glycine tomentella

<400> SEQUENCE: 13

```
atggccttag ctatggtggg agaggcactt atctctgctt ctgtggagat cttgctggat      60
aggataactt ctacagagtt tcgcgatttc tttgccaaca gaaacctcaa tgtttctctc     120
ttggatgagc tgaagataaa gctgttggca ctcaatgctg tgctcaatga tgctgaggag     180
aaacagatca ctaattcagc agtgaaggga tggcttgatg agttgaaaga tgctgtttta     240
gacgcagagg atttgatgga cgaaatcaac acagattctc tgaggtgcaa ggtggaggga     300
gaatttaaaa cctttactag ccaggtgtgg tcatcacttt cttctccctt taatcaattc     360
tataggagca tgaattccaa gcttgaagca atatctggaa ggctagaaca ttttatgaaa     420
caaaaagata ttcttggttt gcaaagtgtt tctaggaaag tctcctacaa aacagttaca     480
gattcattgg ttgaatctgt tgttgttgca agggaggatg acaaagagaa gctactgagc     540
atgcttctct ctgatgaaga tgagaagaat aataacatag aagtgctaac aatattgggc     600
atgggaggtc ttggaaaaac aaccttagct caatgccttt ataatgatag tgcagtgcag     660
aaacattttg atttgaccac ttgggcatgg gtatctgatg attttgatgt gtttagggtg     720
acaaagacaa ttgttgaatc tgtcacttct aaaaattgta atagtactaa ttttgatgct     780
```

```
cttcgtgttg agttgaagaa cagcttgaaa gataaaaagt ttttgcttgt cctcgatgac    840
ctttggaacg aaaagtataa tgattggcat cacctaatag cacctttag cggtggaaaa     900
aagggaagta agattattgt gacaactcga aacagaaag ttgcacaaat gacacataca    960
tatcccgttt atgagctgaa acatctaaca gatgacaatt gttggtgtat acttgctgaa   1020
catgcatttg gcaatgaagg ttatgatgaa tatccaatcc tagaagaaat tggtaggaaa   1080
attgcaaaaa aatgcaatgg cctacccttta gctgctaaaa cattgggagg tcttttgcga  1140
tcaaatgtgg atgcaaaaga atggaataga attctgaaca gcaacttatg ggcacatgaa   1200
gaggtgttac cagctttaca cataagttat cttcatctcc cagcacattt gaaaagatgt   1260
ttttcttatt gctcaatttt tccaaaacaa catttgttgg ataggaagga gttgattctg   1320
ttatggatgc ctgaaggctt tcttcaacaa attcacggag agaaagcaat ggaattagca   1380
ggtgatgact actttaatga attattatca agatctttaa ttgaaaaaga caaaactgaa   1440
gcagaggata agtttcgaat gcatgacctc atctatgatt tggctagact aatagctgga   1500
aaaaactctt gctacttgga aggtaataaa atctcaggag gtgttcgcca attagcatt   1560
tattcaagaa aatttgatgt ctctgaaaga tttgagggct tgcatgacct aaagttttg   1620
cgcactttt tacgactctt taaatatgga cctttcagtt atgggcatgt aaccaaaaag   1680
gtgtcacatg attggttgcc aaaactaaaa tatttgcgaa cattgtcctt gcttggctat   1740
gaaaatatca ctgagttgcc tgattcaata agcaatttgg tgcttttgag gtatcttgac   1800
cttttcctata cttccatcaa aaggttgccc gatgcaacct ttaggcttta caatttgcag   1860
actttgaaat tgtcaaattg taaatgcctt actcagttgc ctgaacagat aggaaatttg   1920
gtcaatctac gccaccttga tattagaggc acaaatttga cggagatgcc agcacaaata   1980
agcaagctac aagatctccg tgtgttgact tcttttgttg taggcagaga agatgggagta  2040
aatatcagag aattaagaaa gtttccttac ttgcaaggta ctctttctat tttggggcta   2100
caaaatgttg ttgatcccaa gcatgctttt caagctgact aaagaagaa agagcatgtt   2160
gaggagctta cgctagagtg gggtagtgag ccacaatatt cacaacttga gaaagatgta   2220
cttcagaacc tgcaaccatc aacaaattta aagaaactca ccataagata ctacagtggc   2280
acaagctttc ctaaatggtt gggtgactct tcatattctt atgttatatt cctttgcatc   2340
actaattgca aatattgctt ttcacttcca ccatttggac aactaccttc tctcaaggag   2400
cttgtgataa aaaggatgaa aatggtgaag acagttggtg aagaattcta ctgcaacaat   2460
ggggtttccc tttcatttca accatttcca ttgttggaga gtatccagtt cgaagagatg   2520
tcagagtggg aagagtggct accatttgaa ggtgaaggca gcaagtttcc ttttccttgc   2580
cttaaacatt tgagtttatc aaaatgcccc aagttgagag gaaacttgcc caaccatcta   2640
ccttcgttga cacatgttcg tatatcagag tgcaacaagc tagaggcaaa atcacatgat   2700
ctacattgga acacatcaat tgaagaaata aaggttagag aagcaggaga agatttgttg   2760
tccttgcttg acaacttttc ttataggaat ctacggatta aaaagtgtga cagcttgtca   2820
tctttgccaa gaatgatact agctgccaat tgtctccaaa ggttgactct taaggatatc   2880
cccaatttga tttccttccc agccgatggc ttgccaacgt cattgcaatc acttagcatt   2940
ttcgactgtg agaacttaga atttctgtct cccgaatcat gccacaaata cacatcactt   3000
gaatatctgt caattgtcaa tagctgccat tccctggcgt ccttaccatt agatggtttc   3060
tcttccctac aaagacttca aatccagaaa tgtcccaaca tggaagcaat tactactcaa   3120
```

| | |
|---|---:|
| ggtggaacga atgctctcaa attaactcat ctgtatgttc gggattgtaa gaaacttagg | 3180 |
| tcacttccag aacagattca tctccctgcc cttcgatggt tagagctttc taagcttcca | 3240 |
| gagctaatat cattgccccc aaggtgtttg ccttccagtt tacaagtact cgaagttgaa | 3300 |
| gttggaatgc tatcatcaat gtctaaacac gagttaggtt tcctattcca acgcctcact | 3360 |
| tctctgtcta gtcttgagat tagtggttat ggggaggaag atgttgttaa caccctgttg | 3420 |
| aaggagtgct tactgcccac ttcgctgcaa tatctgtgcc tagtgaagtt tgatgattta | 3480 |
| aagttgttgg aaggaaaagg gcttcaacag ctcacttccc tcagagggtt tggcatcagg | 3540 |
| aattgtaaaa gcctcgagtc cttgcccgaa gatcagcttc catcctctct tgaattactg | 3600 |
| gagatacatg gttgtccttt actagaagca aggtatcaaa gtcggaaagg gaaacactgg | 3660 |
| tctaagattg ctcacattcc tgcgatcgag ataaatgatg aagtgataat atga | 3714 |

<210> SEQ ID NO 14
<211> LENGTH: 15445
<212> TYPE: DNA
<213> ORGANISM: artificial
<220> FEATURE:
<223> OTHER INFORMATION: Vector 25190

<400> SEQUENCE: 14

| | |
|---|---:|
| attcctgtgg ttggcatgca catacaaatg gacgaacgga taaaccttt cacgcccttt | 60 |
| taaatatccg attattctaa taaacgctct tttctcttag gtttacccgc caatatatcc | 120 |
| tgtcaaacac tgatagttta aactggcact agcctaacgg tgttgactaa ctaggccgct | 180 |
| tccctaatta gctaacccgg gggcgcgccg ggacccgtga ttgcggttac atcatgtacg | 240 |
| gaaaaataat tctaatcctt gatttaaatt tgatcttgac tatttattta ttctttattt | 300 |
| cattttgtaa atcattttat gtatcccctg gcaaggcaat tttatccacc ttgcacccaa | 360 |
| cacttcgggt tcccataaat caaaccacct taacttcaca caatgctgta actcacaccg | 420 |
| cccagcatct ccaatgtgaa agaagctaaa atttaataaa caatcatacg aagcagtgac | 480 |
| aaaataccag atggtattaa tgctttgata aaattaattg gaaagtataa atggtagga | 540 |
| ataattaat tataattaat ttaaataaga ttaaaaataa tttaaaacta aaatgttaaa | 600 |
| attttaagaa aattatttta aataatattt aaaaacattt aaaatcattt taaaaaattt | 660 |
| atttatagga caattaaatg aatatttcag ctaattaaaa acaaaagctt acctagcctt | 720 |
| agaagacaac ttgtccaaca attagatgat acccattgcc cttacgtttt ctttaacatc | 780 |
| aattattgtt tttgtcaaca agctatcttt tagtttatt ttattggtaa aaaatattgt | 840 |
| cgccttcaag ttgcatcatt taacacatct cgtcattaga aaaataaaac tcttccctaa | 900 |
| acgattagta gaaaaaatca ttcgataata aataagcaag caaaattagg aaaaaataac | 960 |
| ttcatttaa aaaaatcatt aaggctatat tttttaaatg actaatttta tatagactgt | 1020 |
| aactaaaagt atacaattta ttatgctatg tatcttaaag aattacttat aaaaatctac | 1080 |
| ggaagaatat cttacaaagt gaaaaacaaa tgagaaagaa tttagtggga tgattatgat | 1140 |
| tttatttgaa aattgaaaaa ataattatta aagactttag tggagtaaga aagctttcct | 1200 |
| attagtcttt tcttatccat aaaaaaaaaa aaaaaatct agcgtgacag cttttccata | 1260 |
| gatttaata atgtaaaata ctggtagcag ccgaccgttc aggtaatgga cactgtggtc | 1320 |
| ctaacttgca acgggtgcgg gcccaattta ataacgccgt ggtaacggat aaagccaagc | 1380 |
| gtgaagggt gaaggtacat ctctgactcc gtcaagatta cgaaaccgtc aactacgaag | 1440 |
| gactcccga aatatcatct gtgtcataaa caccaagtca caccatacat gggcacgcgt | 1500 |

```
cacaatatga ttggagaacg gttccaccgc atatgctata aattgccccc acacccctcg    1560
accctaatcg cacttgaatt gcaatcaaat tagttcattc tctttgcgca gttccctacc    1620
tcccccttcc aaggtccgta gattcctcct gttttttttt cttcttcttt attgtttgtt    1680
ctacatcagc atgatgttga tttgattgtg ttttctatcg tttcatcgat tataaattt    1740 cataatcaga agattcagct tttattaatg caagaacgtc cttaattgat gattttataa    1800
ccgtaaatta ggtctaatta gagttttttt cataaagatt ttcagatccg tttacaacaa    1860
gccttaattg ttgattctgt agtcgtagat taaggttttt ttcatgaact acttcagatc    1920
cgttaaacaa cagccttatt tgttgatact tcagtcgttt ttcaagaaat tgttcagatc    1980
cgttgataaa agccttattc gttgattctg tatggtattt caagagatat tgctcaggtc    2040
ctttagcaac taccttattt gttgattctg tggccataga ttaggatttt ttttcacgaa    2100
attgcttctt gaaattacgt gatggatttt gattctgatt tatcttgtga ttgttgactc    2160
tacaggatcc aaaaaatggc cttagctatg gtgggagagg cacttatctc tgcttctgtg    2220
gagatcttgc tggataggat aacttctaca gagtttcgcg atttctttgc caacagaaac    2280
ctcaatgttt ctctcttgga tgagctgaag ataaagctgt tggcactcaa tgctgtgctc    2340
aatgatgctg aggagaaaca gatcactaat tcagcagtga agggatggct tgatgagttg    2400
aaagatgctg ttttagacgc agaggatttg atggacgaaa tcaacacaga ttctctgagg    2460
tgcaaggtgg agggagaatt taaaaccttt actagccagg tgtggtcatc actttcttct    2520
ccctttaatc aattctatag gagcatgaat tccaagcttg aagcaatatc tggaaggcta    2580
gaacatttta tgaaacaaaa agatattctt ggtttgcaaa gtgtttctag gaaagtctcc    2640
tacaaaacag ttacagattc attggttgaa tctgttgttg ttgcaaggga ggatgacaaa    2700
gagaagctac tgagcatgct tctctctgat gaagatgaga agaataataa catagaagtg    2760
ctaacaatat tgggcatggg aggtcttgga aaaacaacct tagctcaatg cctttataat    2820
gatagtgcag tgcagaaaca ttttgatttg accacttggg catgggtatc tgatgatttt    2880
gatgtgttta gggtgacaaa gacaattgtt gaatctgtca cttctaaaaa ttgtaatagt    2940
actaattttg atgctcttcg tgttgagttg aagaacagct tgaaagataa aaagttttg    3000 cttgtcctcg atgacctttg gaacgaaaag tataatgatt ggcatcacct aatagcacct    3060
tttagcggtg gaaaaaaggg aagtaagatt attgtgacaa ctcgacaaca gaaagttgca    3120
caaatgacac atacatatcc cgtttatgag ctgaaacatc taacagatga caattgttgg    3180
tgtatacttg ctgaacatgc atttggcaat gaaggttatg atgaatatcc aatcctagaa    3240
gaaattggta ggaaaattgc aaaaaaatgc aatggcctac ctttagctgc taaaacattg    3300 ggaggtctt tgcgatcaaa tgtggatgca aagaatgga atagaattct gaacagcaac    3360
ttatgggcac atgaagaggt gttaccagct ttacacataa gttatcttca tctcccagca    3420
catttgaaaa gatgttttc ttattgctca attttccaa aacaacattt gttggatagg    3480
aaggagttga ttctgttatg gatggctgaa ggctttcttc aacaaattca cggagagaaa    3540
gcaatggaat tagcaggtga tgactacttt aatgaattat tatcaagatc tttaattgaa    3600
aaagacaaaa ctgaagcaga ggataagttt cgaatgcatg acctcatcta tgatttggct    3660
agactaatag ctggaaaaaa ctcttgctac ttggaaggta ataaaatctc aggaggtgtt    3720
cgccaattag catttattc aagaaaattt gatgtctctg aaagatttga gggcttgcat    3780
gacctaaagt ttttgcgcac ttttttacga ctctttaaat atggacctt cagttatggg    3840
```

-continued

```
catgtaacca aaaaggtgtc acatgattgg ttgccaaaac taaaatattt gcgaacattg    3900
tccttgcttg gctatgaaaa tatcactgag ttgcctgatt caataagcaa tttggtgctt    3960
ttgaggtatc ttgacctttc ctatacttcc atcaaaaggt tgcccgatgc aacctttagg    4020
ctttacaatt tgcagacttt gaaattgtca aattgtaaat gccttactca gttgcctgaa    4080
cagataggaa atttggtcaa tctacgccac cttgatatta gaggcacaaa tttgacggag    4140
atgccagcac aaataagcaa gctacaagat ctccgtgtgt tgacttcttt tgttgtaggc    4200
agagaagatg gagtaaatat cagagaatta agaaagtttc cttacttgca aggtactctt    4260
tctattttgg ggctacaaaa tgttgttgat cccaagcatg cttttcaagc tgacttaaag    4320
aagaaagagc atgttgagga gcttacgcta gagtggggta gtgagccaca atattcacaa    4380
cttgagaaag atgtacttca gaacctgcaa ccatcaacaa atttaaagaa actcaccata    4440
agatactaca gtggcacaag ctttcctaaa tggttgggtg actcttcata ttcttatgtt    4500
atattccttt gcatcactaa ttgcaaatat tgcttttcac ttccaccatt tggacaacta    4560
ccttctctca aggagcttgt gataaaaagg atgaaaatgg tgaagacagt tggtgaagaa    4620
ttctactgca acaatggggt ttccctttca tttcaaccat ttccattgtt ggagagtatc    4680
cagttcgaag agatgtcaga gtgggaagag tggctaccat ttgaaggtga aggcagcaag    4740
tttccttttc cttgccttaa acatttgagt ttatcaaaat gccccaagtt gagaggaaac    4800
ttgcccaacc atctaccttc gttgacacat gttcgtatat cagagtgcaa caagctagag    4860
gcaaaatcac atgatctaca ttggaacaca tcaattgaag aaataaaggt tagagaagca    4920
ggagaagatt tgttgtcctt gcttgacaac ttttcttata ggaatctacg gattaaaaag    4980
tgtgacagct tgtcatcttt gccaagaatg atactagctg ccaattgtct ccaaaggttg    5040
actcttaagg atatcccaa tttgatttcc ttcccagccg atggcttgcc aacgtcattg    5100
caatcactta gcattttcga ctgtgagaac ttagaatttc tgtctcccga atcatgccac    5160
aaatacacat cacttgaata tctgtcaatt gtcaatagct gccattccct ggcgtcctta    5220
ccattagatg gtttctcttc cctacaaaga cttcaaatcc agaaatgtcc caacatggaa    5280
gcaattacta ctcaaggtgg aacgaatgct ctcaaattaa ctcatctgta tgttcgggat    5340
tgtaagaaac ttaggtcact tccagaacag attcatctcc ctgcccttcg atggttagag    5400
ctttctaagc ttccagagct aatatcattg cccccaaggt gtttgccttc cagtttacaa    5460
gtactcgaag ttgaagttgg aatgctatca tcaatgtcta aacacgagtt aggtttccta    5520
ttccaacgcc tcacttctct gtctagtctt gagattagtg gttatgggga ggaagatgtt    5580
gttaacaccc tgttgaagga gtgcttactg cccacttcgc tgcaatatct gtgcctagtg    5640
aagtttgatg atttaaagtt gttggaagga aaagggcttc aacagctcac ttccctcaga    5700
gggtttggca tcaggaattg taaaagcctc gagtccttgc ccgaagatca gcttccatcc    5760
tctcttgaat tactgagat acatggttgt ccttttactag aagcaaggta tcaaagtcgg    5820
aaagggaaac actggtctaa gattgctcac attcctgcga tcgagataaa tgatgaagtg    5880
ataatatgac tgagctcagc tttttgtgat ctgatgataa gtggttggtt cgtgtctcat    5940
gcacttggga ggtgatctat ttcacctggt gtagtttgtg tttccgtcag ttggaaaaac    6000
ttatccctat cgatttcgtt ttcatttttct gcttttcttt tatgtacctt cgtttgggct    6060
tgtaacgggc ctttgtattt caactctcaa taataatcca agtgcatgtt aaacaatttg    6120
tcatctgttt cggctttgat atactactgg tgaagatggg ccgtactact gcatcacaac    6180
gaaaaataat aataagatga aaaacttgaa gtggaaaaaa aaacttgaa tgttcactac    6240
```

```
tacctagcta gttagcggac cgctaattag ctaagagaca cttgtgtgat tgagagaaac   6300
actaatcttg tgaggactga agtttggtga ttatttcttg tgatctgtcg acaaaaatat   6360
caaatggggt ttcttttaca aattatttac ctaaatgaat ctgttttgaa aatatttact   6420
ccattgggtc tattttttta ttacaaagcg tctccctgaa gggcgcgttc cccgtgaaag   6480
tgacacgtgg caggacttgg gacgtgccct gcgtacaggc gcgatagtta gtgttgttac   6540
agcaggcgca tcgggtcgtg ttggggacca aggtacgaca ggtcgcgctg ggtgacccag   6600
acacgaccca attgggtcgc actttattta atatttttta tattttgtat attgttttta   6660
tttaatatat ttttatatta ttttatttaa tttttttata ttttatataa tagttttctat  6720 attaaataaa ttcttagcat tatgtatgat tttaaagtca taaataattt tttatattgt   6780
ttttatttac tatattttt  atatttatt  taatatttat atattaaata aatccttcat   6840
attagaaaaa ataagaaaa  tattaaataa aatataaaat ataaaaagt  aaaaaatatt   6900 aaataaaata atataaaaaa tattataaaa acaatataaa aatataaaa  atatttaata   6960 aaataataaa aaaatatta  ttttaaataa aattatttat gactttaaac tctaaagttg   7020 aatttttaaaa aaatataatt tttttacgat tttagtaaaa aaaaaataca agccgcacaa   7080
tacaagtcgc cttctcaaac ccttcctcac gacattctcg gaccttatga caccgtcacc   7140
aaaacaatga tccacgcgat attaggcgcg tgcaaatcac tctaatccga aactagtaga   7200
catgggaagc acgagctata cgcgagcgtt tcaattgccg ccacgaaagc agagaaggcc   7260
agaaacggaa ccacggtaaa atggtaaggg tattttcgta aacagaagaa aagagttgta   7320
gctataaata aaccctctaa cccacggcgc actatttctc ttcactcctt cgttcactct   7380
tcttctcttg cggctagggt tttagcgcag cttcttctag gttcgttctc ttccgccgct   7440
ctatggattt taaaccttcg aatcatgttt attccattga attatgttgc ttgcagttta   7500
tattttctga atctgtagtt gttgtcttca atttatccta tgctttatag atcaatcttt   7560
tgtgtgtgta gtacgtaatt tttgttcttt ttgcttttcg ttcaagttgt tgggaataat   7620
cggggtatca tgttttgata ttgtttgttt tcttttttga ctgcttaata attttttaagt  7680 tggttttggt tttgggtttt tatgtgcttg ttatattcaa atctttgtga tccagatctt   7740
acaaaagttt tgggtttaag gatgttttg  gctgatgatg aatagatcta taaactgttc   7800
cttttaatcg attcaagctt aggattttac taggcttttg cgaataaata cgtgacagta   7860
agctaattat gtccttttt  tgtctcaatc atatctgtct gggtgtgcca taatttgtga   7920
tatgtctatc tggtagaatc ttgtgtttta tgctttacga tttggtatac ctgttttga   7980 acttgttgta tgatgggtat ttagatcacc ctatcttttt tatgcttctg gaagttttat   8040
gtaaatgtcg aatatcttaa tgttgttgaa cttataatgt tgtgttgatg tatgtatgat   8100
ggttttgaca acttttttca ctggttctga agttttatg  taaattgcaa atatgttaat   8160
gttgttgaac ttatttttt  tccttcgatg ttgttttgat gtatgtatga tggttttcac   8220
cgtagtttct atggctaata tcttaatgtt gttgagctta ttttttcct  tatatgttgt   8280 gttgatgtat tgtatgatgg ttttgacaac ttttttagtt tctttgcaga tttaaggaag   8340
aaaaaaaaaa tggctcttgt tgctagacca gtgcttctg  ctagagttgc tgcttctaga   8400
ccaagagttg ctgcaagaaa ggctgttaga gtgtctgcta tgtctcatgg tgcttcatct   8460
agaccagcta ctgctagaaa gtcctctgga cttctggaa  ctgttaggat tccaggcgat   8520
aagtctattt cccaccgttc tttcatgttc ggaggacttg cttctggtga gactagaatt   8580
```

| | |
|---|---|
| actggacttc ttgagggcga ggatgttatt aacactggaa aggctatgca ggctatggga | 8640 |
| gctagaatta gaaaagaggg cgatacctgg attattgatg gtgttggaaa cggtggactt | 8700 |
| cttgctccag aagctccact tgatttcgga aacgctgcta ctggatgcag acttactatg | 8760 |
| ggacttgttg gagtgtacga tttcgattcc accttcattg gagatgcttc tcttactaag | 8820 |
| aggccaatgg gaagagtgct taacccactt agagagatgg gagttcaggt taagtctgag | 8880 |
| gatggtgata ggcttccagt tactcttaga ggaccaaaga ctccaacccc aattacttac | 8940 |
| agagtgccaa tggcttctgc tcaagttaag tctgctgttc ttcttgctgg acttaacact | 9000 |
| ccaggtatta ccactgtgat cgagccaatt atgaccagag atcataccga gaagatgctt | 9060 |
| caaggattcg gagctaacct taccgttgaa actgatgctg atggtgttag gaccattaga | 9120 |
| cttgagggaa gaggaaagct taccggacaa gttattgatg ttccaggtga tccatcttct | 9180 |
| accgctttcc ctcttgttgc tgctcttttg gttccaggat ctgatgtgac cattcttaac | 9240 |
| gtgctcatga acccatctag gaccggactt attcttaccc ttcaagaaat gggcgctgat | 9300 |
| attgaggtta tcaacccaag acttgctggt ggtgaagatg ttgctgatct tagggttagg | 9360 |
| tcctctactc ttaagggtgt tactgttcca gaagataggg ctccatccat gattgatgag | 9420 |
| tacccaattc ttgctgtggc tgctgctttc gctgaaggtg ctactgttat gaacggactt | 9480 |
| gaggaactta gggtgaaaga gtctgatagg cttttctgctg ttgctaacgg acttaagctt | 9540 |
| aacggtgtgg attgtgatga gggtgagact tctcttgttg ttagaggtag accagatgga | 9600 |
| aagggacttg gaaacgcttc tggtgcagca gttgcaactc atcttgatca taggatcgct | 9660 |
| atgtccttcc ttgttatggg tcttgtttct gagaacccag ttaccgttga tgatgctact | 9720 |
| atgattgcta ccagcttccc agagttcatg gatcttatgg ctggacttgg agctaagatt | 9780 |
| gagctttctg ataccaaggc tgcctgacta attagctaag agcttgatcc gtcgacctgc | 9840 |
| agatcgttca acatttggc aataaagttt cttaagattg aatcctgttg ccggtcttgc | 9900 |
| gatgattatc atataatttc tgttgaatta cgttaagcat gtaataatta acatgtaatg | 9960 |
| catgacgtta tttatgagat gggtttttat gattagagtc ccgcaattat acatttaata | 10020 |
| cgcgatagaa aacaaaatat agcgcgcaaa ctaggataaa ttatcgcgcg cggtgtcatc | 10080 |
| tatgttacta gatccctgca ggcccggggg cgcgccctaa ttagctaacg gccaggatcg | 10140 |
| ccgcgtgagc ctttagcaac tagctagatt aattaacgca atctgttatt aagttgtcta | 10200 |
| agcgtcaatt tgtttacacc acaatatatc ctgccaccag ccagccaaca gctccccgac | 10260 |
| cggcagctcg gcacaaaatc accactcgat acaggcagcc catcagaatt aattctcatg | 10320 |
| tttgacagct tatcatcgac tgcacggtgc accaatgctt ctggcgtcag cagccatcg | 10380 |
| gaagctgtgg tatggctgtg caggtcgtaa atcactgcat aattcgtgtc gctcaaggcg | 10440 |
| cactcccgtt ctggataatg ttttttgcgc cgacatcata acggttctgg caaatattct | 10500 |
| gaaatgagct gttgacaatt aatcatccgg ctcgtataat gtgtggaatt gtgagcggat | 10560 |
| aacaatttca cacaggaaac agaccatgag ggaagcgttg atcgccgaag tatcgactca | 10620 |
| actatcagag gtagttggcg tcatcgagcg ccatctcgaa ccgacgttgc tggccgtaca | 10680 |
| tttgtacggc tccgcagtgg atggcggcct gaagccacac agtgatattg atttgctggt | 10740 |
| tacggtgacc gtaaggcttg atgaaacaac gcggcgagct ttgatcaacg accttttgga | 10800 |
| aacttcggct tcccctggag agagcgagat tctccgcgct gtagaagtca ccattgttgt | 10860 |
| gcacgacgac atcattccgt ggcgttatcc agctaagcgc gaactgcaat ttggagaatg | 10920 |
| gcagcgcaat gacattcttg caggtatctt cgagccagcc acgatcgaca ttgatctggc | 10980 |

```
tatcttgctg acaaaagcaa gagaacatag cgttgccttg gtaggtccag cggcggagga   11040
actctttgat ccggttcctg aacaggatct atttgaggcg ctaaatgaaa ccttaacgct   11100
atggaactcg ccgcccgact gggctggcga tgagcgaaat gtagtgctta cgttgtcccg   11160
catttggtac agcgcagtaa ccggcaaaat cgcgccgaag gatgtcgctg ccgactgggc   11220
aatggagcgc ctgccggccc agtatcagcc cgtcatactt gaagctaggc aggcttatct   11280
tggacaagaa gatcgcttgg cctcgcgcgc agatcagttg gaagaatttg ttcactacgt   11340
gaaaggcgag atcaccaaag tagtcggcaa ataaagctct agtggatctc cgtacccagg   11400
gatctggctc gcggcggacg cacgacgccg gggcgagacc ataggcgatc tcctaaatca   11460
atagtagctg taacctcgaa gcgtttcact tgtaacaacg attgagaatt tttgtcataa   11520
aattgaaata cttggttcgc attttttgtca tccgcggtca gccgcaattc tgacgaactg   11580
cccatttagc tggagatgat tgtacatcct tcacgtgaaa atttctcaag cgctgtgaac   11640
aagggttcag atttttagatt gaaaggtgag ccgttgaaac acgttcttct tgtcgatgac   11700
gacgtcgcta tgcggcatct tattattgaa taccttacga tccacgcctt caaagtgacc   11760
gcggtagccg acagcaccca gttcacaaga gtactctctt ccgcgacggt cgatgtcgtg   11820
gttgttgatc tagatttagg tcgtgaagat gggctcgaga tcgttcgtaa tctggcggca   11880
aagtctgata ttccaatcat aattatcagt ggcgaccgcc ttgaggagac ggataaagtt   11940
gttgcactcg agctaggagc aagtgatttt atcgctaagc cgttcagtat cagagagttt   12000
ctagcacgca ttcgggttgc cttgcgcgtg cgccccaacg ttgtccgctc caaagaccga   12060
cggtcttttt gttttactga ctggacactt aatctcaggc aacgtcgctt gatgtccgaa   12120
gctggcggtg aggtgaaact tacggcaggt gagttcaatc ttctcctcgc gttttttagag   12180 aaaccccgcg acgttctatc gcgcgagcaa cttctcattg ccagtcgagt acgcgacgag   12240
gaggtttatg acaggagtat agatgttctc attttgaggc tgcgccgcaa acttgaggca   12300
gatccgtcaa gccctcaact gataaaaaca gcaagaggtg ccggttattt ctttgacgcg   12360
gacgtgcagg tttcgcacgg ggggacgatg gcagcctgag ccaattccca gatccccgag   12420
gaatcggcgt gagcggtcgc aaaccatccg gcccggtaca aatcggcgcg cgctgggtg    12480 atgacctggt ggagaagttg aaggccgcgc aggccgccca gcggcaacgc atcgaggcag   12540
aagcacgccc cggtgaatcg tggcaagcgg ccgctgatcg aatccgcaaa gaatcccggc   12600
aaccgccggc agccggtgcg ccgtcgatta ggaagccgcc caagggcgac gagcaaccag   12660
attttttcgt tccgatgctc tatgacgtgg gcacccgcga tagtcgcagc atcatggacg   12720
tggccgtttt ccgtctgtcg aagcgtgacc gacgagctgg cgaggtgatc cgctacgagc   12780
ttccagacgg gcacgtagag gtttccgcag ggccggccgg catggccagt gtgtgggatt   12840
acgacctggt actgatggcg gtttcccatc taaccgaatc catgaaccga taccgggaag   12900
ggaagggaga caagcccggc cgcgtgttcc gtccacacgt tgcggacgta ctcaagttct   12960
gccggcgagc cgatggcgga aagcagaaag acgacctggt agaaacctgc attcggttaa   13020
acaccacgca cgttgccatg cagcgtacga agaaggccaa gaacggccgc ctggtgacgg   13080
tatccgaggg tgaagccttg attagccgct acaagatcgt aaagagcgaa accgggcggc   13140
cggagtacat cgagatcgag ctggctgatt ggatgtaccg cgagatcaca gaaggcaaga   13200
acccggacgt gctgacggtt cacccccgatt actttttgat cgatcccggc atcggccgtt   13260
ttctctaccg cctggcacgc cgcgccgcag gcaaggcaga agccagatgg ttgttcaaga   13320
```

```
cgatctacga acgcagtggc agcgccggag agttcaagaa gttctgtttc accgtgcgca    13380
agctgatcgg gtcaaatgac ctgccggagt acgatttgaa ggaggaggcg gggcaggctg    13440
gcccgatcct agtcatgcgc taccgcaacc tgatcgaggg cgaagcatcc gccggttcct    13500
aatgtacgga gcagatgcta gggcaaattg ccctagcagg ggaaaaaggt cgaaaaggtc    13560
tctttcctgt ggatagcacg tacattggga acccaaagcc gtacattggg aaccggaacc    13620
cgtacattgg gaacccaaag ccgtacattg ggaaccggtc acacatgtaa gtgactgata    13680
taaaagagaa aaaaggcgat ttttccgcct aaaactcttt aaaacttatt aaaactctta    13740
aaacccgcct ggcctgtgca taactgtctg gccagcgcac agccgaagag ctgcaaaaag    13800
cgcctaccct tcggtcgctg cgctccctac gccccgccgc ttcgcgtcgg cctatcgcgg    13860
ccgctggccg ctcaaaaatg gctggcctac ggccaggcaa tctaccaggg cgcggacaag    13920
ccgcgccgtc gccactcgac cgccggcgct gaggtctgcc tcgtgaagaa ggtgttgctg    13980
actcatacca ggcctgaatc gccccatcat ccagccagaa agtgagggag ccacggttga    14040
tgagagcttt gttgtaggtg gaccagttgg tgattttgaa cttttgcttt gccacggaac    14100
ggtctgcgtt gtcgggaaga tgcgtgatct gatccttcaa ctcagcaaaa gttcgattta    14160
ttcaacaaag ccgccgtccc gtcaagtcag cgtaatgctc tgccagtgtt acaaccaatt    14220
aaccaattct gattagaaaa actcatcgag catcaaatga aactgcaatt tattcatatc    14280
aggattatca ataccatatt tttgaaaaag ccgtttctgt aatgaaggag aaaactcacc    14340
gaggcagttc cataggatgg caagatcctg gtatcggtct gcgattccga ctcgtccaac    14400
atcaatacaa cctattaatt tcccctcgtc aaaataagg ttatcaagtg agaaatcacc    14460
atgagtgacg actgaatccg gtgagaatgg caaaagctct gcattaatga atcggccaac    14520
gcgcggggag aggcggtttg cgtattgggc gctcttccgc ttcctcgctc actgactcgc    14580
tgcgctcggt cgttcggctg cggcgagcgg tatcagctca ctcaaaggcg gtaatacggt    14640
tatccacaga atcaggggat aacgcaggaa agaacatgtg agcaaaaggc cagcaaaagg    14700
ccaggaaccg taaaaaggcc gcgttgctgg cgttttccca taggctccgc cccctgacg    14760 agcatcacaa aaatcgacgc tcaagtcaga ggtggcgaaa cccgacagga ctataaagat    14820
accaggcgtt tccccctgga agctccctcg tgcgctctcc tgttccgacc ctgccgctta    14880
ccggatacct gtccgccttt ctcccttcgg gaagcgtggc gctttctcat agctcacgct    14940
gtaggtatct cagttcggtg taggtcgttc gctccaagct gggctgtgtg cacgaacccc    15000
ccgttcagcc cgaccgctgc gccttatccg gtaactatcg tcttgagtcc aacccggtaa    15060
gacacgactt atcgccactg gcagcagcca ctggtaacag gattagcaga gcgaggtatg    15120
taggcggtgc tacagagttc ttgaagtggt ggcctaacta cggctacact agaagaacag    15180
tatttggtat ctgcgctctg ctgaagccag ttaccttcgg aaaaagagtt ggtagctctt    15240
gatccggcaa acaaaccacc gctggtagcg gtggtttttt tgtttgcaag cagcagatta    15300
cgcgcagaaa aaaggatct caagaagatc ctttgatctt ttctacgggg tctgacgctc    15360
agtggaacga aaactcacgt taagggattt tggtcatgag attatcaaaa aggatcttca    15420
cctagatcct tttgatccgg aatta                                          15445
```